(12) United States Patent
Laing et al.

(10) Patent No.: US 11,793,436 B2
(45) Date of Patent: Oct. 24, 2023

(54) URINARY EVENT DETECTION, TRACKING, AND ANALYSIS

(71) Applicant: ClearTrac Technologies, LLC, Elizabethton, TN (US)

(72) Inventors: Brent Laing, Greenwood Village, CO (US); John Green, Elizabethton, TN (US); Paul R. Johnson, Boulder, CO (US); Robert John Smith, Louisville, CO (US); Robert Edwin Schneider, Erie, CO (US); Magnus Hargis, Hudson, CO (US); Elise Geolat Edson, Boulder, CO (US); Elizabeth A. O'Brien, Louisville, CO (US)

(73) Assignee: ClearTrac Technologies, LLC, Elizabethton, TN (US)

( * ) Notice: Subject to any disclaimer, the term of this patent is extended or adjusted under 35 U.S.C. 154(b) by 251 days.

(21) Appl. No.: 16/297,417

(22) Filed: Mar. 8, 2019

(65) Prior Publication Data

US 2019/0365308 A1    Dec. 5, 2019

Related U.S. Application Data

(60) Provisional application No. 62/679,582, filed on Jun. 1, 2018.

(51) Int. Cl.
*A61B 5/20* (2006.01)
*G01D 21/00* (2006.01)
(Continued)

(52) U.S. Cl.
CPC .............. *A61B 5/208* (2013.01); *A61B 5/205* (2013.01); *A61B 10/007* (2013.01);
(Continued)

(58) Field of Classification Search
CPC .............. G01N 1/10; G01N 2001/205; G01N 2001/007; G01N 33/4925; A61B 5/208;
(Continued)

(56) References Cited

U.S. PATENT DOCUMENTS 2,648,981 A    8/1953  Drake
3,859,854 A    1/1975  Dye et al.
(Continued)

FOREIGN PATENT DOCUMENTS

CN    2221776 Y    3/1996
CN    105769223 A    7/2016
(Continued)

OTHER PUBLICATIONS

PCT, "International Search Report and Written Opinion", Application No. PCT/US2019/021454, dated Aug. 21, 2019, 13 pages.
(Continued)

*Primary Examiner* — Brandi N Hopkins
(74) *Attorney, Agent, or Firm* — Dorsey & Whitney LLP

(57) ABSTRACT

The present disclosure generally relates to methods and systems for generating a void profile for user void events. The method includes receiving by a processing element a plurality of outputs from a fluid level sensor corresponding to a plurality of levels of fluid flowing through a voiding device during a flow event; determining by the processing element a beginning and an end time of the fluid flow into the voiding device during the flow event; analyzing the plurality of outputs of the fluid level sensor over a time interval defined by the beginning and end time of the fluid flow to determine at least one of a fluid flow rate data and an accumulated volume data for the fluid flowing through the voiding device; and storing the fluid flow rate data and the accumulated flow volume data in a memory.

13 Claims, 39 Drawing Sheets

(51) Int. Cl.
*G01F 23/26* (2022.01)
*A61B 10/00* (2006.01)
*G06F 9/54* (2006.01)
*B23Q 1/54* (2006.01)
*G01M 99/00* (2011.01)
*A61B 5/00* (2006.01)

(52) U.S. Cl.
CPC ........... *B23Q 1/5475* (2013.01); *G01D 21/00* (2013.01); *G01F 23/26* (2013.01); *G01M 99/00* (2013.01); *G06F 9/542* (2013.01); *A61B 5/0059* (2013.01); *A61B 5/204* (2013.01); *A61B 5/7275* (2013.01); *A61B 2562/0223* (2013.01)

(58) Field of Classification Search
CPC ... A61B 5/14507; A61B 10/007; G01F 1/007; G01F 23/266; G01F 23/263; A61M 2205/3592; H04N 5/2257; G01G 21/28; G01G 17/04; G01G 19/52
See application file for complete search history.

(56) References Cited

U.S. PATENT DOCUMENTS

| | | |
|---|---|---|
| 3,871,230 A | 3/1975 | Dye et al. |
| 3,884,072 A | 5/1975 | Cheng |
| 3,929,412 A | 12/1975 | Villari |
| 4,051,431 A | 9/1977 | Wurster |
| 4,085,616 A | 4/1978 | Patel et al. |
| 4,131,016 A | 12/1978 | Layton |
| 4,238,448 A | 12/1980 | Layton et al. |
| 4,343,316 A | 8/1982 | Jespersen |
| 4,554,687 A | 11/1985 | Carter et al. |
| 4,619,273 A | 10/1986 | Iosif |
| 4,891,993 A | 1/1990 | Barker |
| 5,062,304 A | 11/1991 | Van et al. |
| 5,176,148 A | 1/1993 | Wiest et al. |
| 5,377,101 A | 12/1994 | Rollema |
| 6,904,809 B1 | 6/2005 | Aundal |
| 6,931,943 B1 | 8/2005 | Aundal |
| 7,416,542 B2 | 8/2008 | Aundal |
| 7,606,617 B2 | 10/2009 | Wariar |
| 7,739,907 B2 | 6/2010 | Boiarski |
| 7,819,020 B2 | 10/2010 | Jacobi et al. |
| 7,892,217 B2 | 2/2011 | Boiarski |
| 8,141,420 B2 | 3/2012 | Hirao |
| 8,231,552 B2 | 7/2012 | Shahar et al. |
| 8,424,376 B2 | 4/2013 | Boiarski |
| 8,500,705 B2 | 8/2013 | Kim |
| 8,544,341 B2 | 10/2013 | Grumbles et al. |
| 8,813,551 B2 | 8/2014 | Boiarski |
| 8,986,613 B2 * | 3/2015 | Cohen .................. A61B 10/007 205/792 |
| 9,021,878 B2 | 5/2015 | Grinstein et al. |
| 9,642,737 B2 | 5/2017 | Seres et al. |
| 9,775,556 B2 | 10/2017 | Dimino et al. |
| 10,219,733 B2 | 3/2019 | Shimokawa et al. |
| 2005/0261605 A1 | 11/2005 | Shemer et al. |
| 2008/0300649 A1 | 12/2008 | Gerber et al. |
| 2008/0312556 A1 | 12/2008 | Dijkman |
| 2008/0312557 A1 | 12/2008 | Cho et al. |
| 2011/0000309 A1 | 1/2011 | Griffiths et al. |
| 2011/0174067 A1 | 7/2011 | Boiarski |
| 2012/0109008 A1 | 5/2012 | Charlez et al. |
| 2012/0226196 A1 | 9/2012 | Dimino et al. |
| 2015/0362351 A1 | 12/2015 | Joshi et al. |
| 2016/0029942 A1 | 2/2016 | Paulsen et al. |
| 2016/0051176 A1 | 2/2016 | Ramos et al. |
| 2016/0113562 A1 | 4/2016 | Belotserkovsky |
| 2016/0331282 A1 | 11/2016 | Satish et al. |
| 2017/0020433 A1 | 1/2017 | Hotaling et al. |
| 2017/0086728 A1 * | 3/2017 | Hidas ..................... A61B 5/743 |
| 2017/0105670 A1 | 4/2017 | Holt et al. |
| 2017/0135622 A1 * | 5/2017 | Shimokawa ........... A61B 5/208 |
| 2017/0307423 A1 | 10/2017 | Pahwa et al. |
| 2018/0085008 A1 | 3/2018 | Hall et al. |
| 2019/0365307 A1 | 12/2019 | Laing et al. |
| 2020/0015735 A1 | 1/2020 | Burns et al. |
| 2021/0275073 A1 | 9/2021 | Korkor et al. |

FOREIGN PATENT DOCUMENTS

| | | |
|---|---|---|
| CN | 106037766 A | 10/2016 |
| DE | 3007855 A1 | 9/1981 |
| DE | 19751111 A1 | 6/1999 |
| DE | 102014008760 A1 | 1/2015 |
| EP | 2303124 B1 | 8/2012 |
| EP | 2741671 B1 | 1/2016 |
| EP | 2716219 B1 | 3/2017 |
| EP | 2564778 B1 | 4/2018 |
| JP | 2000313240 A | 11/2000 |
| JP | 3729732 B2 | 10/2005 |
| JP | 2006038873 A | 2/2006 |
| KR | 20110030826 A | 3/2011 |
| RU | 2034516 C1 | 5/1995 |
| RU | 2071724 C1 | 1/1997 |
| RU | 2643110 C1 | 1/2018 |
| WO | 2009035599 A1 | 3/2009 |
| WO | 2009142508 A1 | 11/2009 |
| WO | 2014141234 A1 | 9/2014 |
| WO | 2016056571 A1 | 4/2016 |
| WO | 2017036952 A1 | 3/2017 |
| WO | 2017149272 A1 | 9/2017 |
| WO | 2018036664 A1 | 3/2018 |
| WO | 2018051244 A1 | 3/2018 |
| WO | 2018217818 A1 | 11/2018 |

OTHER PUBLICATIONS

Extended European Search Report dated Mar. 16, 2022 in connection with European patent application No. 19810595.9, 10 pages., dated Mar. 16, 2022.

* cited by examiner

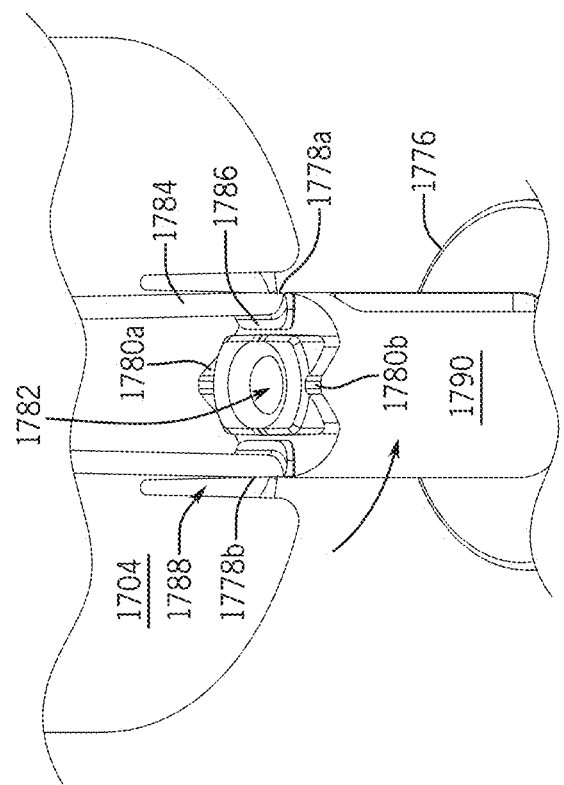
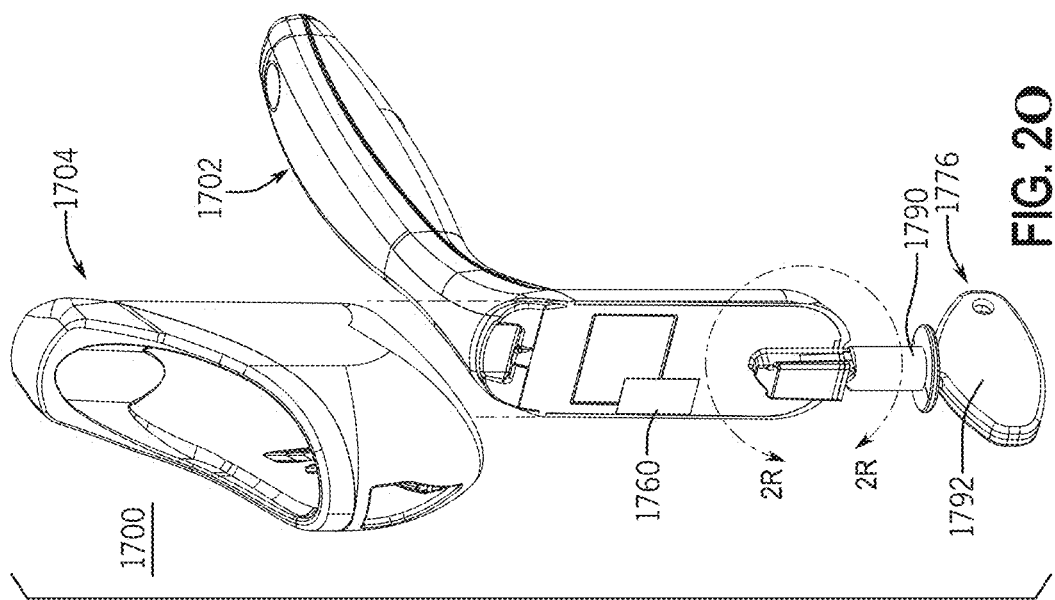

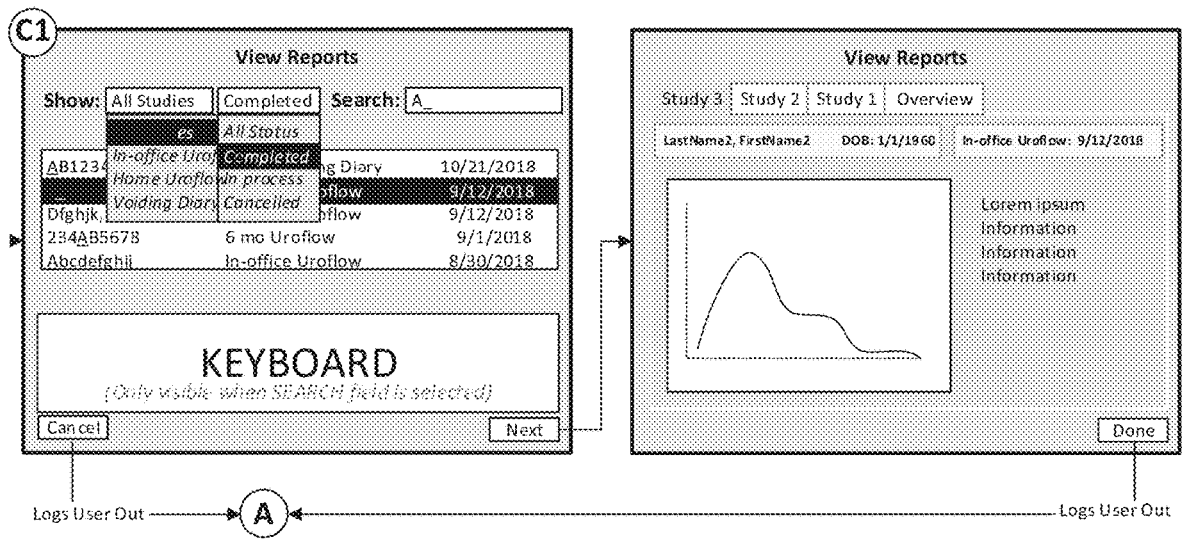
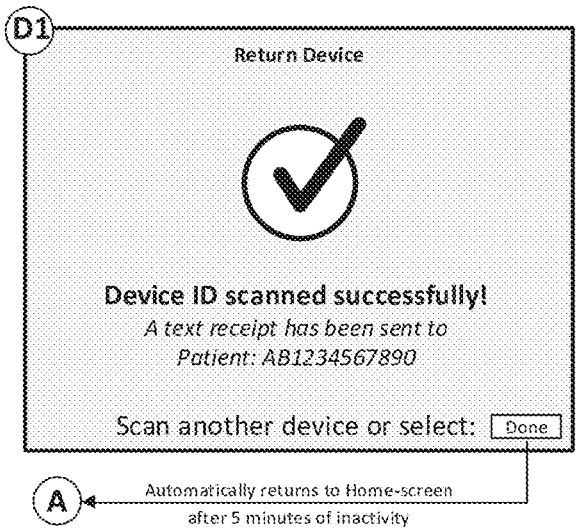
Fig. 17E

URINARY EVENT DETECTION, TRACKING, AND ANALYSIS

CROSS-REFERENCE TO RELATED APPLICATIONS

The present application claims priority from U.S. provisional patent application No. 62/679,582 filed 1 Jun. 2018 and titled, "UROFLOWMETER" the entirety of which is incorporated herein by reference for all purposes.

This application is related to the U.S. patent application Ser. No. 16/296,647, now U.S. Pat. No. 11,534,093, filed 8 Mar. 2019 and titled, "TESTING DEVICE FOR A UROFLOMETER"; and U.S. patent application Ser. No. 6/297,192 filed 8 Mar. 2019 and titled "UROFLOWMETER" the entireties of which are incorporated herein by reference for all purposes.

TECHNICAL FIELD

The technology described herein relates generally to systems and methods for processing and managing data generated from uroflowmeters.

BACKGROUND

Uroflowmeters are used to monitor and diagnose the urinary tract health of patients. Uroflowmeters measure data regarding the flow of urine during a urination event, or void. Healthcare providers can use data to diagnose obstructions in the urinary tract and other conditions before treatment, and to track treatment progress and effectiveness.

Traditionally, uroflowmeters are bulky, expensive, nonportable devices that remain in doctor's offices. These devices are inconvenient and cannot accurately capture a complete record of patient voids, because patients are put in an un-natural setting, cannot remain in a doctor's office in proximity to the uroflowmeter for a prescribed period more than a few hours, and may produce errant results as patients modify their behavior to use the uroflowmeter.

Related to traditional in-office uroflowmeters, patients may be asked to keep a manual paper or written log of fluid intake and void information, such as urgency, frequency, or volume of urine, in a record, or void (or urinary) diary, of void events over a prescribed period of time. Patients may record voiding volume by voiding into a voiding measurement bowl placed over a toilet. Patients are reluctant to carry the voiding measurement bowl and paper diary with them because the bowl is large, indiscrete, and inconvenient. Due to the lack of portability, there are often voids missing from the diary. Additionally, often there is a delay between a patient completing a void and filling out the diary, which results in erroneous information being recorded or missing information. Finally, there is potential for delay in submitting a paper void diary back to the doctor's office for transcription into an electronic form. Handwriting may be illegible, or worse, the entire diary could be lost. These shortcomings result in delays and reduction in the quality of patient care.

SUMMARY

The present disclosure generally relates to systems and methods for processing and managing data generated from uroflowmeters.

A method for generating a urine flow void profile for a user flow event is disclosed. The method includes: receiving by a processing element a plurality of outputs from a fluid level sensor corresponding to a plurality of levels of fluid flowing through a voiding device during a flow event; determining by the processing element a beginning and an end time of the fluid flow into the voiding device during the flow event; analyzing the plurality of outputs of the fluid level sensor over a time interval defined by the beginning and end time of the fluid flow to determine at least one of a fluid flow rate data and an accumulated volume data for the fluid flowing through the voiding device; and storing the fluid flow rate data and the accumulated flow volume data in a memory.

A method for validating a flow event detected by a voiding device as corresponding to a urinary event is disclosed. The method includes: validating a flow event detected by a voiding device as corresponding to a urinary event, including: receiving from a fluid sensor and a validation sensor flow characteristics of the fluid flow through the voiding device during the flow event; determining that the flow event corresponds to a urinary event; for the urinary event transmitting unanalyzed data to a server; and outputting a void profile corresponding to the flow event.

A method for generating a urinary diary for display on a user device is disclosed. The method includes: determining by a processing element that a urinary event occurred; accessing void profile characteristics corresponding to the urinary event, the void profile characteristics being detected by a voiding device in electronic communication with a server; receiving user input void data via the user device; determining a diary time slot corresponding to the urinary event and the user void data; and associating the urinary event and void profile characteristics to generate a correspondence between the user input void data and the void profile characteristics.

A method of correlating a voiding device with a patient is disclosed. The method includes: receiving by a processing element patient data corresponding to the patient; generating by the processing element a patient identifier corresponding to the patient data; generating by the processing element a first device identifier corresponding to a first portion of the voiding device; generating by the processing element a second device identifier corresponding to a second portion of the voiding device; associating the first portion of the voiding device with the second portion of the voiding device; generating by the processing element a linkage between the patient identifier and the first device identifier to associate the patient data with the voiding device; and outputting to a display by the processing element a confirmation display confirming a linkage between the patient identifier and the device identifier.

A method of assessing urinary treatment effectiveness is disclosed. The method includes: receiving by a processing element pre-treatment void diary data corresponding to a patient urinary history during a first time interval, the pre-treatment void diary data including void characteristics detected by a voiding device during void events by the patient during the first time interval; receiving by the processing element a treatment plan prescribed to the patient by a healthcare provider; receiving by the processing element post-treatment void diary data corresponding to the patient urinary history during a second time interval, the post-treatment void diary data including void characteristics detected by a voiding device during void events by the patient during the second time interval; analyzing by the processing element the pre-treatment void diary data and the post-treatment void diary data to determine treatment effectiveness; and outputting by the processing element to a display an effectiveness assessment.

A system for assessing the urinary health of the patient is disclosed. The system includes: a handheld voiding device which includes: a flow sensor; a device processing element; and a flow chamber wherein the handheld voiding device receives patient urine and receives by the device processing element a plurality of outputs of the flow sensor corresponding to a plurality of levels of a fluid flowing through the handheld voiding device during a flow event; a server in communication with the handheld voiding device, wherein the server receives flow event data from the voiding device and by a server processing element analyzes the flow event data to validate a void event, and determines a parameter associated with the valid void event data, and associates the parameter with a void diary stored in a memory, and outputs a urinary health report; and a healthcare provider device in communication with the server, wherein the healthcare provider device receives the urinary health report from the server.

A method of processing data from a uroflowmeter is disclosed. The method includes: providing a uroflowmeter in communication with a voiding diary system; detecting flow event data by the uroflowmeter; transmitting the flow event data to the voiding diary system; analyzing by the voiding diary system the flow event to determine a void event; analyzing urine fluid level and duration data to determine void characteristics; and generating a graphical output of the urine flow rate, duration, volume and timestamp data to develop a treatment plan.

BRIEF DESCRIPTION OF THE DRAWINGS

FIG. 2O is a partially exploded view of the uroflowmeter of FIG. 2M illustrating a method of decoupling a flow chamber and a handle of the uroflowmeter in accordance with various examples of the present disclosure.

FIG. 2P is a partial detailed perspective view of an example of an attachment of a flow chamber and a handle of the uroflowmeter of FIG. 2M.

FIG. 17E is a flow diagram exhibiting a specific implementation of portions of the method of FIG. 9.

DETAILED DESCRIPTION

Figure 1:
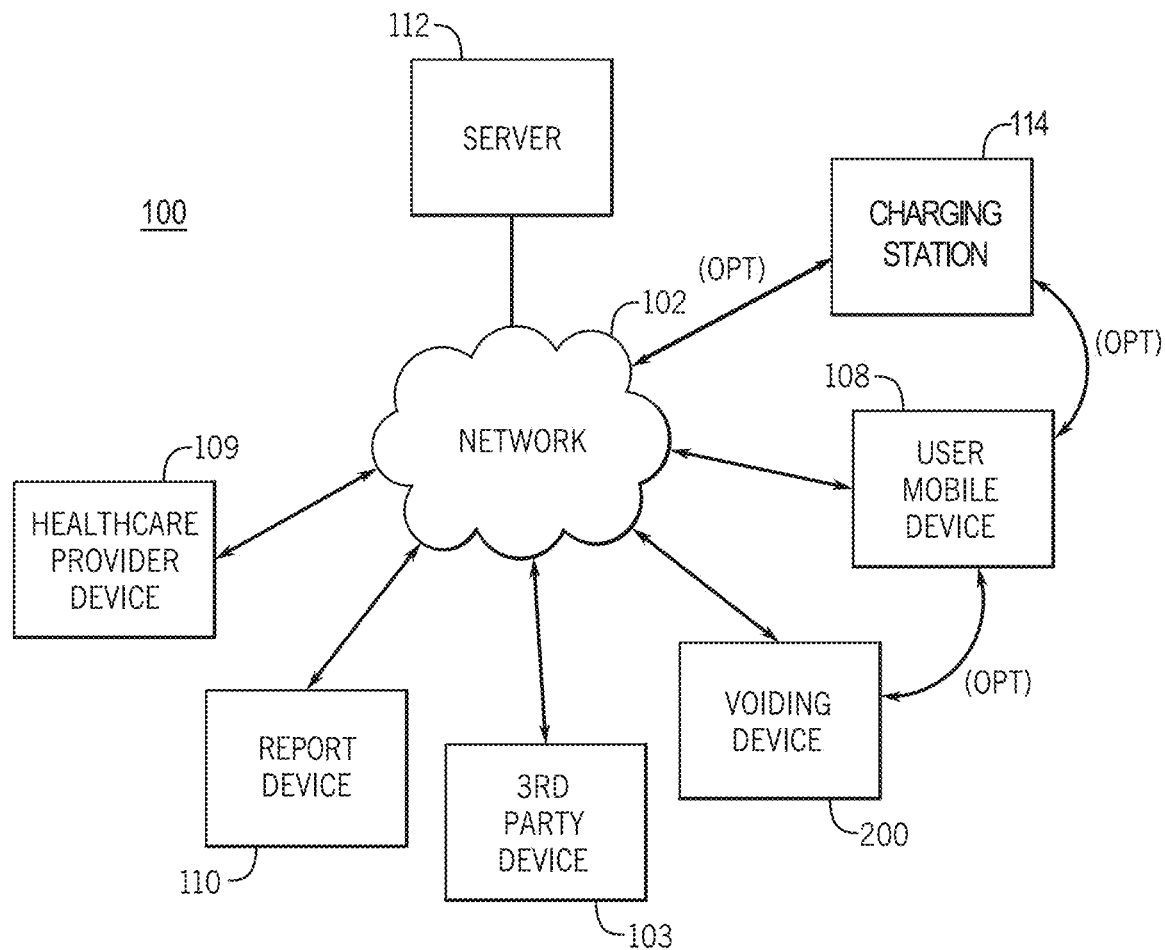
FIG. 1 is a simplified schematic diagram of an information management system for a voiding device.

The present disclosure generally relates to systems and methods for analyzing and managing data generated from uroflowmeters or voiding devices to assist and increase accuracy in patient diagnostics and treatment. In one example a voiding device is disclosed that communicates with one more electronic devices (e.g., user smart phone, tablet computer, laptop, server, cloud network, or the like). The voiding device includes positioning and flow sensors that detect void data corresponding to a urinary or use event, such as flow rate, time metadata, and the like. Examples of sensors of the voiding device may include: a buoyant float coupled to a displacement sensor, a temperature sensor, conductivity sensor, opacity sensor, a clock or timer, and the like. The void data detected by the sensors is then verified to determine if it corresponds to a likely void event or whether it corresponds to another non-urinary/void event, such as a patient washing the voiding device after use. This validation helps to prevent irrelevant data from being stored in a patient's void profile information, as well as reduce data transfer within the system, increasing the accuracy of the recorded void profiles to increase treatment effectiveness.

In one example, the system compares sensor data with validity criteria to determine whether data are associated with a void event, or some other type of event, for instance rinsing the voiding device. As a specific example, the system uses the data to determine whether a float orientation is correct, e.g., whether the float is inverted, sideways, or at some other orientation inconsistent with a void. In instances where the float orientation is consistent with a user washing the voiding device versus voiding into the device (e.g., the float is sideways or the like), the detected data, such as flow rate, may be discarded as corresponding to a non-voiding event.

As another example, the system may also use detected flow characteristics, such as peak flow rate, duration of flow, or total flow volume, to determine if collected data are consistent with a void. Specifically, in instances where a peak flow is too high, a duration of flow is too long, or that a flow volume is too large, the system may determine that such data corresponds to some other event or otherwise includes errors and discards the data or otherwise associates the data with a non-void event. In another example, the system may determine that a fluid temperature flowing through the voiding device is within an expected range to be consistent with a void. The system may validate the data using one or multiple sensors to validate detected data as corresponding to a void event. Using multiple sensors introduces redundancy into the system to help prevent inadvertent discarding of real void data, while reducing the number of sensors can increase the processing speed at which data can be validated. As such, the number and types of flow information used to validate a particular user flow event may be varied as desired.

In the event that the void data corresponds to an actual urinary user flow event by the patient, the system uses the detected flow information to determine voided urine volume, average urine flow rate, maximum flow rate, voiding duration, voiding flow time, time to maximum urine flow, as well as other detected void profile characteristics. The void profile characteristics may be generated in real time or after a series of voids have been collected. The void characteristics or data may be transmitted to a patient's personal electronic device or another electronic device, directly from the voiding device (e.g., Bluetooth®) or via a network, e.g., from a cloud server to the user's device. Similarly, the void characteristics can be transmitted, directly or indirectly, to a healthcare provider and/or third party insurer to assist in treatment and payment decisions. Because the void profile characteristic may be automatically transferred to a user device and/or a third party or healthcare provider device and the void profile characteristics are captured in real-time as a user is voiding, the data are accurate and can more effectively be used to assess treatment.

Additionally, the disclosure includes methods to correspond detected void characteristics with user activity, fluid consumption, urinary input, or the like, to generate a more complete and holistic urinary diary, which was previously not possible with conventional devices. In one example, an application or other program executing on the user device may receive user input related to the user's fluid consumption, urinary events, leakage, and the like, where the user is presented with questions or other interfaces tailored to the detected void profile characteristics. A urinary event is any event involving the flow of urine from a user's urinary tract. Using the user input and the void characteristics, the system may generate a void profile for the user for the select use period. Due to the dual-input (user input and detected data), 1:1 correspondence between a void and a user activity can be determined that may increase diagnostic accuracy by a healthcare provider.

Relatedly, the voiding device and user information may be transmitted to a healthcare provider device. For example, the voiding device may be assigned to a particular patient or user from a healthcare provider, and the voiding device may be given a device identifier that corresponds to a patient identifier, associating or linking the two together. From there, the user inputs information into his or her mobile device, and the void data collected by the voiding device then is received, processed, and may be transmitted directly to the healthcare provider device, such that the healthcare provider can receive void profile data, user consumption data, and the like, with the data being tied to the particular patient. After a period of use, e.g., observation or testing period, or when treatment is complete, the user may return the voiding device back to the healthcare provider. At this point, the healthcare provider may dissociate the device from the current user, disconnect the disposable portion of the voiding device (discarding the disposable portion and cleaning/disinfecting the durable portion), recharge the device, and return the durable portion of the voiding device back into service to be assigned or coupled to another user. Disassociating the voiding device 200 may also include recharging the battery 272, purging stored information, and/or testing the device for readiness. In another example, a healthcare provider's office may have one or more voiding devices in a charging unit, enabling their use for patients while in the provider's office. The charging unit may be coupled to the voiding device, either wirelessly or via a wire (e.g., universal serial bus "USB") to transmit and receive data from the voiding devices. The charging device can then transmit received data to a server for storage, processing, analysis and reporting or optionally may analyze the data itself.

The voiding device and methods herein may also be used to assess treatment effectiveness, which can then be used to vary treatment, as well as generate payment frameworks for insurers or other third parties. In one example, the system may receive user pre-treatment void diary data including void characteristics detected by the voiding device as well as user input information and compare the pre-treatment void diary data to post-treatment void diary data conducted after the user has completed a prescribed treatment plan. Comparing the results and void characteristics an experienced professional can then help to determine the effectiveness of the treatment, or thresholds (e.g., time to urinary max flow, number of void events, and the like), that may be used to score or otherwise rank the effectiveness of various treatment plans. This scoring can be used to provide feedback to healthcare providers, generate improved treatment plans, and provide payment schedules based on effectiveness. Additionally, if a treatment plan is not effective for particular patients, a healthcare provider or insurer may use the pre-treatment void dairy data and the post-treatment void diary data to determine the need to prescribe different treatment plans for those patients.

Referring to FIG. 1, a system 100 for analyzing and managing data generated from uroflowmeters to assist and increase accuracy in patient diagnostics and treatment is disclosed. The system may include a network 102, one or more voiding devices 200 for measuring data related to void or urinary events, a user mobile device 108, a healthcare provider device 109, a report device 110, a charging station 114, and/or a third party device 103. Any combination of the voiding device 200, user mobile device 108, healthcare provider device 109, a report device 110, charging station 114, and/or a third party device 103 may be in electronic communication with one another via network 102 or in some instances directly (e.g., wired connection). The voiding device 200 may be in communication with server 112 directly via the network 102. For example, the user mobile device 108 may be in communication with network 102 and/or the voiding device 200 via network 102 or directly without the use of network 102. The voiding devices 200 may be in direct communication with the charging station 114.

In one method of using the system, a healthcare provider, such as a doctor, nurse, or other assistant, associates a handheld voiding device 200 with a patient whose urinary health is being studied. The patient may be seeking treatment, undergoing treatment, or assessing changes in urinary health post-treatment. The patient empties his or her bladder of urine (i.e., voids), into or on the handheld voiding device 200. The voiding device 200 collects data regarding various characteristics, e.g., liquid level, flow rate, and accumulated volume of during the flow events in which a liquid flows through it. The voiding device 200 then determines whether the flow event is a void, and validates the data as void data. In instances where the flow event is determined to not correspond to a void event, e.g., corresponds to a rinse event, or if the movement or other characteristics during the flow event would render unusable data, the voiding device 200 discards the detected flow data. Because the voiding device 200 may do an initial void/not a void validation process and discard incorrect or unusable data, the memory on-board of the device 200 can be limited since only actual data for analysis may be stored.

In instances where the voiding device 200 has validated the flow event data as being a potential void event, the voiding device 200 transmits the collected, un-analyzed data to the server 112 via the network 102, such as via a cellular telephone network. A server processing element 152 then analyzes the potential void event data to validate whether the data are associated with a void event and then determines various characteristics of the void, e.g., peak flow, void volume, average flow, time to maximum flow, the flow time, the void time, or other characteristics as desired. The server processing element 152 may be associated with the server 112, the healthcare provider device 109, the report device 110, the third party device 103, the user mobile device 108, or another device. The server 112 may then record the void profile characteristics in a patient's void diary or record of urinary events. The patient may also keep a void diary by inputting information into a user device hosting a diary application. In particular, the void diary may be on a user mobile device 108 such as a mobile phone, but may also be recorded using manual methods. The server 112 may combine voiding device 200 data with user-input data, as well as any other reports or studies inputted by a healthcare provider, insurer, caretaker, or the patient. A healthcare provider may then access the combined data to manage and monitor the patient's urinary health. When the patient has completed the urinary health study, the voiding device 200 may be returned to the healthcare provide for re-use, in whole or in part, and association with a new user.

In examples where the server processing element 152 analyzes the void data, the device processing element 252 on the voiding device 200 can be made less expensive (possibly disposable) and include more modest power requirements, thus extending the battery life as compared to examples where the voiding device analyzes the data on-board. Further, the server processing element(s) 152 are generally more powerful than on-board microprocessors, and therefore can provide more robust analysis and analyze the data more quickly than a device processing element 252 in the voiding device 200. The server or servers 112 (e.g., distributed cloud network or cloud computing) may be able to process the data from multiple voiding devices 200 further reducing costs. Additionally, the server 112 may be more easily updated with new software and hardware, relative to trying to push an update through to a number of voiding devices 200 in various locations, such a people's home, doctor's offices and the like. Moreover, utilizing the server 112 for analysis can assist in scalability, enabling an operator of the system to buy server time or processing power on a virtual server when increased demand warrants it, and scale back the server in other times of less demand. A virtual server 112 may be used, rather than, or in addition to, physical servers 112. Because security is a concern when handling patient medical data, a server 112 analyzing void data is also beneficial because it may provide for more robust security, securing a few servers 112 as compared to many voiding devices 200.

The network 102 may be any system where two or more processing elements are in communication with one another. For example, network 102 may be a private cellular telephone network, a local area network, radio wave transmission, a public network, or the internet. Communication on network 102 may be by any suitable means, e.g., wired, wireless, optical, or the like. For example, network 102 may include communications via, Ethernet, Wi-Fi®, Bluetooth®, near field communication, radio frequency identification, infrared, or the like, as well as other communication components such as universal serial bus ("USB") cables or receptacles, or similar physical connections using conductive wires or fiber optic cables. It should be understood that the network 102 may have multiple networks. The voiding device 200 may communicate directly with the network 102. For example, the voiding device 200 may communicate via a cellular telephone network. Alternately, the voiding device may communicate with the user mobile device 108 via Bluetooth® and the user mobile device 108 may then communicate with the server via the Internet.

The user mobile device 108 may be substantially any type of electronic or computer device, and may be connected to one or more computer networks 102. In one example, the user mobile device 108 may be a smart phone, tablet, laptop, or other held-held computing device. A connection between a user mobile device 108 and a computer network 102 may be continuous, or it may be intermittent.

The healthcare provider device 109 may be substantially any type of electronic or computer device used by a healthcare provider in conjunction with a voiding device 200. In one example, healthcare provider device 109 may be a smart phone, tablet or other held-held computer. In another example, healthcare provider device 109 may be a desktop computer, laptop, or server.

The report device 110 may be similar to the healthcare provider device 109, but used by an insurance provider in conjunction with a voiding device 200. In one example, the report device 110 may be a smart phone, tablet or other held-held computer. In another example, the report device 110 may be a desktop computer, laptop, or server.

The third party device 103 is similar to the healthcare provider device 109 and/or report device 110 and is typically tied to parties other than the patient or healthcare provider, e.g., people or organizations who are involved in the care of a user of a voiding device 200. For example, a third party may be a caregiver who is not a healthcare professional, such as a family member. In one example, third party device 103 may be a smart phone, tablet or other held-held computer. In another example, third party device 103 may be a desktop computer, laptop, or server.

The charging station 114 stores and charges the voiding devices 200 so they are charged and ready for use. The charging station 114 interacts with the voiding devices to charge them, such as through the use of cooperating inductive coils in the charging station 114 and the voiding devices 200 or via a wired connection to the voiding devices 200. The charging station 114 also interacts with the voiding devices 200 by analyzing and/or transmitting radio frequency data between the voiding devices 200 and the charging station 114. The transmitted data includes information about a particular voiding device 200, such as a device identifier, device status, patient association information, battery state of charge, and the like. The transmitted data may also include other information such as patient flow data or void data and can be transmitted in both directions between the charging station 114 and the voiding devices 200. The transmitted data may further include software or firmware updates for the device processing elements 252 of the voiding devices 200, stored in memory 254. In various examples, the radio frequency data are transmitted by near-field communication ("NFC"); Wi-Fi®; Bluetooth®; cellular telephone network technologies; or other wireless technologies.

The voiding device 200 captures data corresponding to a user's urine flow events or void events, and determines void data corresponding to these events. In one example, the voiding device 200 is handheld, such that a user can hold the voiding device 200 over a toilet or other receptacle during a void to capture urine flow. In another example, the voiding device 200 may attach to a toilet seat in order to receive a user's urine during a void event. The voiding device 200 may have one or more apertures of predetermined size and shape allowing urine to flow out of the voiding device 200. Examples of the voiding device 200 are disclosed in U.S. patent application Nos. 62/679,582 filed 1 Jun. 2018 and titled, "UROFLOWMETER"; Ser. No. 29/649,761 filed 1 Jun. 2018 and titled, "UROFLOWMETER".

Figure 18:
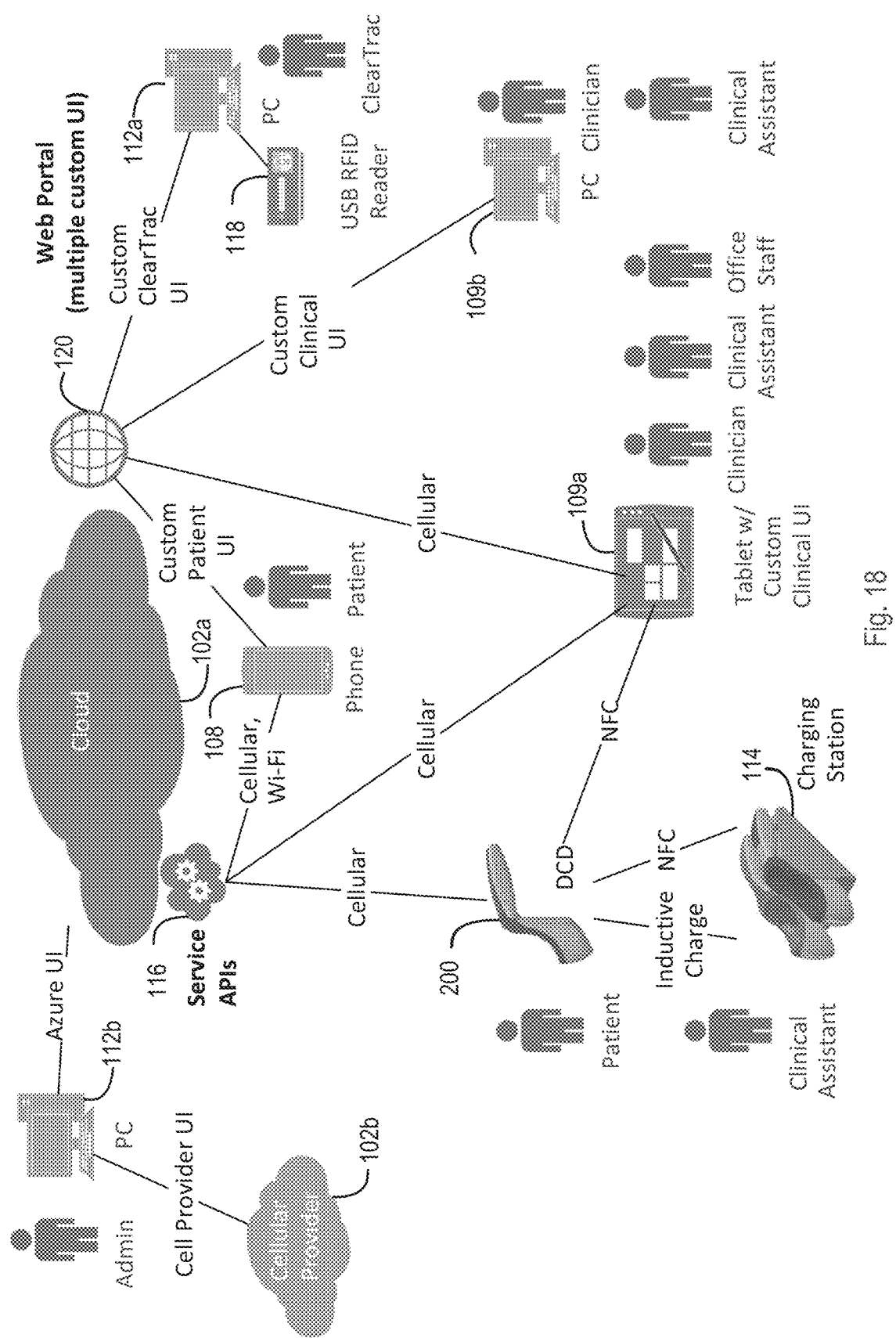
FIG. 18 is a schematic diagram of an illustrative implementation of portions the information management system of FIG. 1.

In various instances data can be transferred between the voiding devices 200, server 112, and associated user devices (e.g., user mobile device 108, healthcare provider device 109, report device 110, third party device 103, etc.) in multiple manners. FIG. 18 illustrates a specific implementation of the information management system 100 of FIG. 1. The implementation has one or more patients who may have user mobile devices 108. The implementation has two networks 102*a* and 102*b*. The network 102*a* is the internet, or cloud. The network 102*b* is a private cellular provider network. There are two servers 112*a* and 112*b*. The server 112*a* is a server provided by the implementer of the information management system 100. The server 112*a* may run a web application for staff of the implementer to manage clinic set up, inventory, and distribution functions. The server 112*b* may run a web application for staff of the implementer to manage SIM card allocation, billing, system access, and higher level corporate administrative functions. There is a USB-based radio frequency identification ("RFID") reader 118. There is a web portal 120 with multiple custom user interfaces ("UI"). There are multiple service application program interfaces ("APIs") 116. In its simplest form, an API is a set of computer executable instructions that allow two devices or two software programs to communicate with one another. There are multiple voiding devices 200. Some voiding devices 200 are placed in an inductive charging station 114 when not in use. In this implementation, there are two healthcare provider devices 109*a* and 109*b*. The healthcare provider device 109*a* is a tablet computer, accessible by a clinician, such as a doctor, a clinical assistant, and/or office staff. Healthcare provider device 109*b* is a desktop personal computer, accessible by a clinician and/or clinical assistant.

The voiding devices 200 communicate with a service API 116 via the cellular network 102*b*. The service API 116 enables communication between the cloud 102*a* and the voiding device 200. The voiding devices 200 also communicate via NFC with the healthcare provider device 109*a*. The NFC data transmitted between the voiding devices 200 and the healthcare provider device 109*a* may include the same data transmitted between the charging station 114 and the voiding devices 200. The healthcare provider device 109*a* may use NFC to associate or dissociate a voiding device 200 with a patient. The healthcare provider device 109*a* communicates with a service API 116 via cellular network 102*b*. The healthcare provider device 109*a* may use cellular communications instead of, or in addition to, NFC to communicate with the voiding devices 200. The healthcare provide device 109*a* may also contain an RFID communications device to communicate with the voiding devices 200. The server 112*a* serves the web portal 120 with multiple custom UIs. The server 112*a* communicates with a USB-based RFID reader 118 that can add new voiding devices 200; manage existing voiding devices 200; and/or remove damaged, lost, used, or expired voiding devices 200 from the information management system 100. The healthcare provider device 109*a* communicates via the cellular network 102*b* with the web portal UI 120, and to the server 112*a*, and the other devices within the information management system 100. The healthcare provider device 109*b* communicates with the web portal UI 120 via wired or wireless communications technologies, such as Wi-Fi®, or Ethernet to the server 112*a*, and the other devices within the information management system 100. The user mobile devices 108 communicate with the service APIs 116 via cellular network 102*b*, or through Wi-Fi®. The user mobile devices 108 also communicate with the web portal 120. The 112*b* communicates with the cloud 102*a*, and with cellular network 102*b*, providing user interfaces between the networks 102*a* and 102*b*.

In an exemplary use case of the implementation of the information management system 100 of FIG. 18, a patient seeks medical treatment from a clinician. The clinician, or staff, associates a voiding device 200 to the patient using the healthcare provider device 109*a* or 109*b*. The patient uses the voiding device 200 to record flow information from voiding events. The voiding device 200 transmits the flow data to the server 112*a* for analysis and validation, via the service API 116. The patient records information related to void events using the user mobile device 108 that accesses a custom UI served by the web portal 120, or has a custom application installed on the user mobile device 108. The server 112*a* combines the user mobile device 108 data with voiding device 200 data to develop a comprehensive voiding diary that the clinician can access via healthcare provider device 109*a* or 109*b*, and use to diagnose, treat, and assess the patient's condition.

Figure 2A:
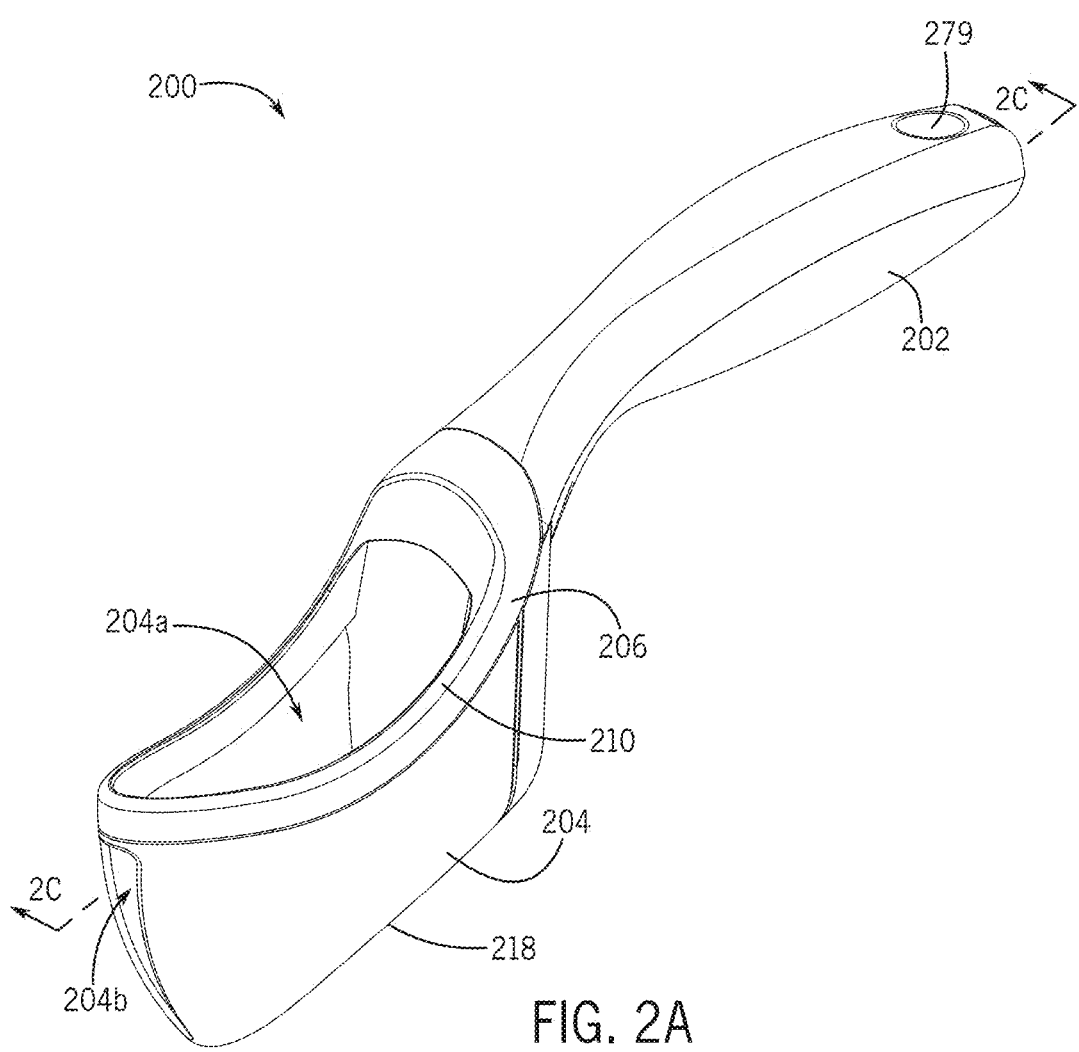
FIG. 2A is a perspective view of an example of a voiding device.
Figure 2B:
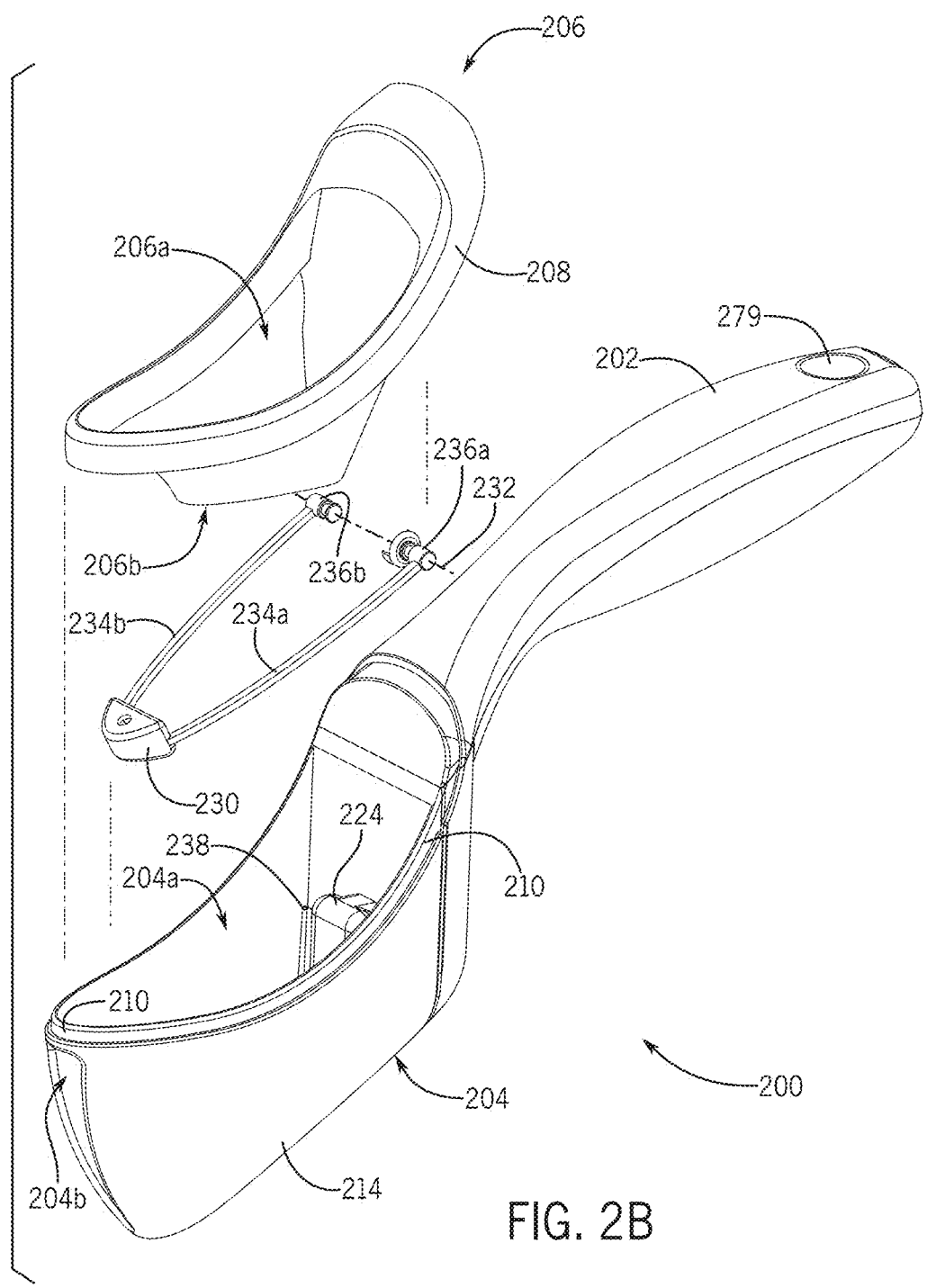
FIG. 2B is a partially exploded perspective view of an example of a voiding device.

FIG. 2A illustrates a perspective view of an illustrative voiding device 200. FIG. 2B illustrates an exploded view of the voiding device 200 of FIG. 2A. The voiding device 200 includes a flow chamber 204 that momentarily collects and measures urine or other fluid flow while a user is voiding. The flow chamber 204 includes an inlet 204*a* and an outlet 204*b*. The flow chamber 204 optionally includes a funnel 206 to produce a smooth flow of urine into the flow chamber. The funnel 206 may define a contour that directs or guides a flow of urine into the flow chamber 204. The contour of the funnel 206 may facilitate reducing turbulent flow of the urine within the flow chamber 204. This may produce a smooth or settled flow of the patient's urine within the flow chamber 204. In some cases, the funnel 206 may form a consistent, laminar flow of the urine. The funnel 206 may include features that orientate or align anatomy of a male patient relative to the voiding device 200 in order to facilitate directing or guiding the male patient's urine into the inlet 204*a* of the flow chamber 204. The inlet 204*a* receives urine from the user during use and the outlet 204*b* allows the collected urine to exit the voiding device 200, such as into a toilet, for disposal. The inlet 204*a* may be defined along a top of the voiding device 200 to facilitate urine collection. The outlet 204*b* may be defined along a side (such as a front sidewall as illustrated in FIG. 2A, 2B) of the voiding device 200 to facilitate urine disposal and allow a user to more easily direct the outflow into the proper receptacle. The voiding device 200 typically includes a handle 202 for grasping by a patient. The handle 202 extends from a rearward direction from the flow chamber 204 and may be elongated and relatively slender to provide an ergonomic grip for a patient's hand. In some aspects, a light emitting diode ("LED") is integrated with the elongated handle. The LED may indicate an orientation value of the voiding device 200 corresponding to a target condition, such as a target orientation value.

The voiding device 200 may include various sensors that detect void data corresponding to a void event. The voiding device 200 may include various types of sensors to determine urine flow rate and urine void volume. In many examples, the voiding device 200 includes one or more flow sensors or fluid level sensors 262. The one or more fluid level sensors 262 may be substantially any type of electronic device, or multiple devices, capable of detecting the fluid level in the flow chamber 204 of the voiding device 200. The fluid level sensor 262 may output an electrical or optical signal corresponding to the level of the fluid in the flow chamber 204. The outputs of the fluid level sensor 262 may correspond to positions of the fluid level sensor 262 during a time interval. The fluid level sensor 262 may include one or more image or optical sensors (e.g., time of flight sensor systems), inductive sensors, magnetic sensors, and/or other sensors. In various examples, the fluid level sensor 262 uses magnetic Hall effect sensing to determine the fluid level in the flow chamber 204. For example, the fluid level sensor 262 may include a magnetic displacement sensor 222, such as a rotary Hall effect sensor, that measures the rotary angle of a nearby magnet 226.

It should be noted that the displacement sensor 222 may measure either a linear or an angular displacement of the float. In another example, the fluid level sensor 262 is an accelerometer connected to a flexible float. As the float rises or falls, such as in response to fluid levels, the accelerometer registers a change in its position and thus the fluid level. In another example, the fluid level sensor 262 is a plurality of corresponding pairs wetted electrodes placed at various locations within flow chamber 204. As fluid rises within the flow chamber 204 the fluid may bridge across corresponding pairs of electrodes, enabling a current to flow between them, thereby detecting the fluid level. In another example, the fluid level sensor 262 is a plurality of temperature sensors, such as thermistors, thermocouples, or resistance temperature devices placed at various locations within flow chamber 204. As fluid rises within the flow chamber 204 it may cause a temperature change in various of the plurality of temperature sensors, thereby detecting the fluid level. In another example, the fluid level sensor 262 is a resistive strip that encounters a change in electrical resistance when exposed to an electrically conductive fluid, such as urine. In another example, the fluid level sensor 262 is an optical detector, such as a camera, or light emitter and receiver, that measures liquid level in flow chamber 204 relative to graduation marks (e.g., lines showing the volume of fluid at a given point) within flow chamber 204. In another example, the fluid level sensor 262 is a light emitter and receiver that measure changes in optical transmissive power through a fiber-optic element at that element is exposed to varying levels of fluid within flow chamber 204. In another example, the fluid level sensor 262 is a strain gauge, such as a Wheatstone bridge coupled to a buoyant element. The strain gauge measures the strain on the float as it moves, such as in response to various levels of fluid within flow chamber 204.

The voiding device 200 may have one or more validation sensors 260 that enable the device processing element 252 of the voiding device 200 to analyze one or more validation characteristics to validate whether collected data corresponds to a valid void event. These validation sensors 260 may measure validation characteristics of the voiding device 200 and/or the validation characteristics of the voiding device 200 environment, which can then be compared against typical voiding validation characteristics and/or voiding environments to determine if the event is a void event and if it is a void whether the data is usable (e.g., not too noisy or error prone). In one example, a validation sensor 260 includes one or more of the orientation sensors. In one example, the orientation sensor is an accelerometer. In another example, the orientation sensor is a gyroscope. In one example, the validation sensor 260 detects the grip of a user. In one example, a grip sensor is a capacitive or resistive sensor with an output corresponding to a user's grip. In another example, a validation sensor 260 is a button, switch or the like that the user activates indicating that the voiding device 200 is about to receive a void. In another example, the validation sensor 260 is a proximity sensor, detecting the proximity of the voiding device 200 to the user's hand, body, or genitals, indicating the voiding device 200 as about to receive a void.

The fluid level sensor 262 determines the fluid level in the flow chamber 204. In one example, the fluid level sensor 262 includes a buoyant float 230 coupled with a displacement sensor 222, such that the displacement sensor 222, in combination with the float 230, can be used to determine a level of liquid, or changes to a level of liquid over time within the voiding device 200. The displacement sensor 222 is coupled to the flow chamber 204 and is fluidly sealed from the annular space 216. For example, the flow chamber 204 defines a housing 224 in which the displacement sensor 222 is seated. The housing 224 fluidly seals the displacement sensor 222 from fluid in the flow chamber 204, while permitting the displacement sensor 222 to detect fluid levels in the flow chamber 204.

Figure 2C:
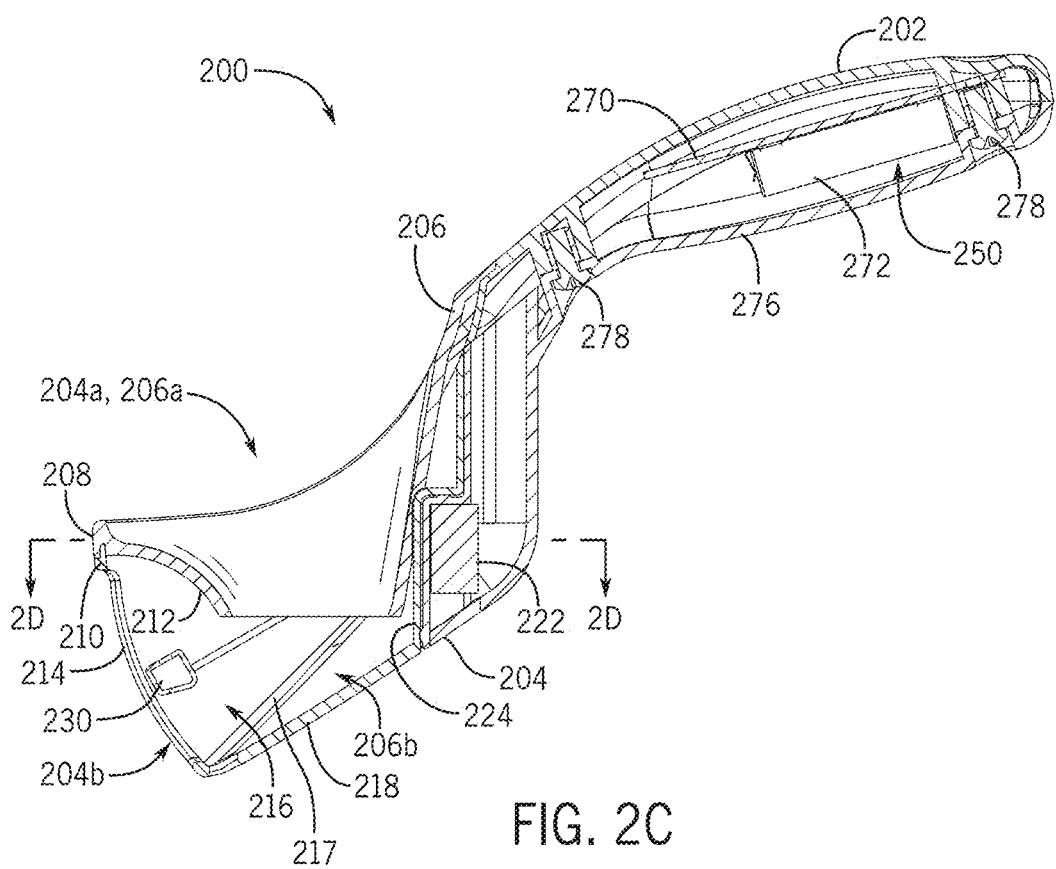
FIG. 2C is a section view of an example of a voiding device, taken along line 2C-2C of FIG. 2A.
Figure 2D:
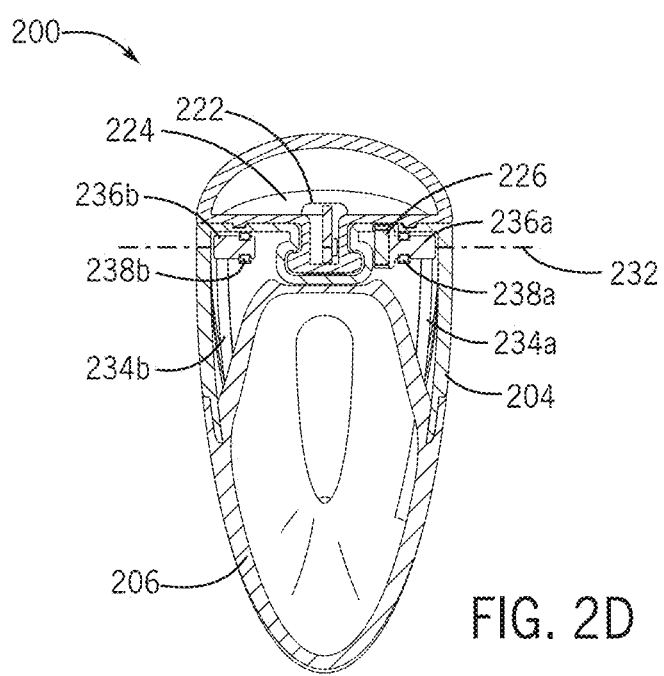
FIG. 2D is a section view of an example of a voiding device, taken along line 2D-2D of FIG. 2C.
Figure 2E:
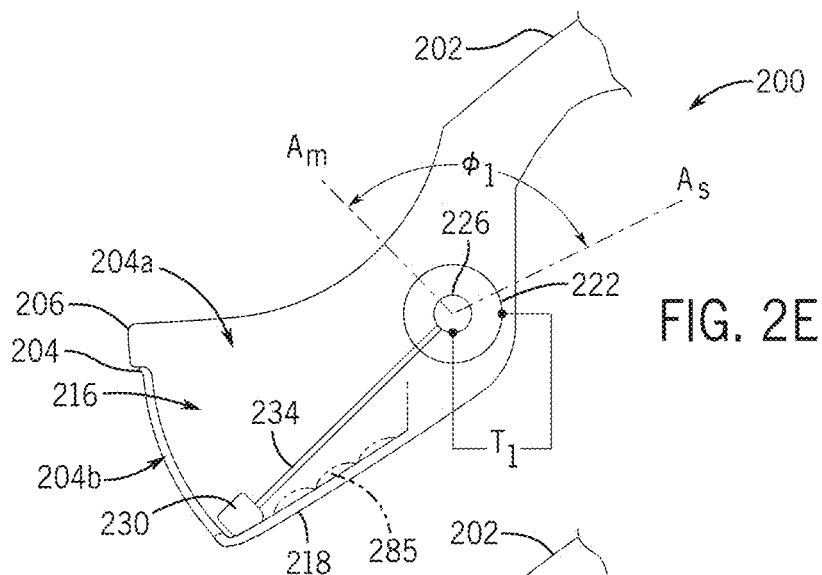
FIG. 2E depicts the voiding device of FIG. 2A in first configuration.
Figure 2F:
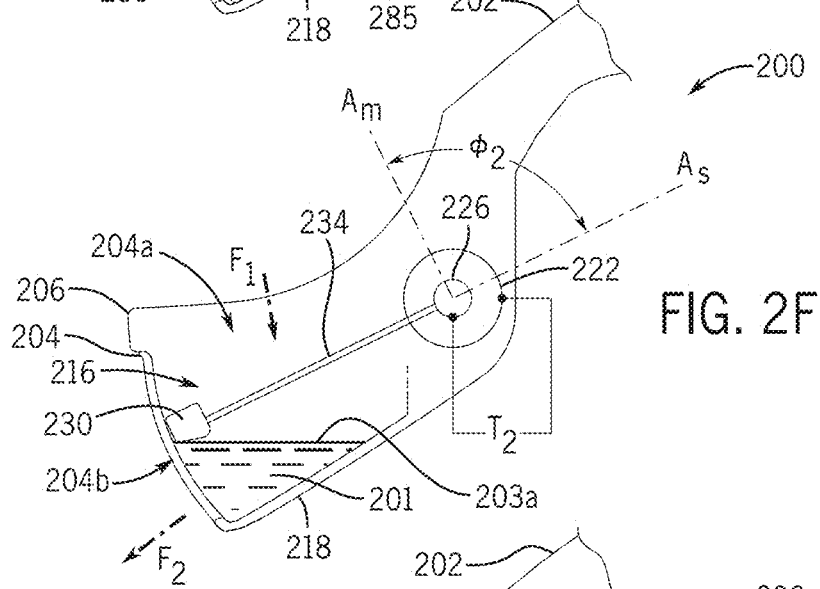
FIG. 2F depicts the voiding device of FIG. 2A in a second configuration.
Figure 2G:
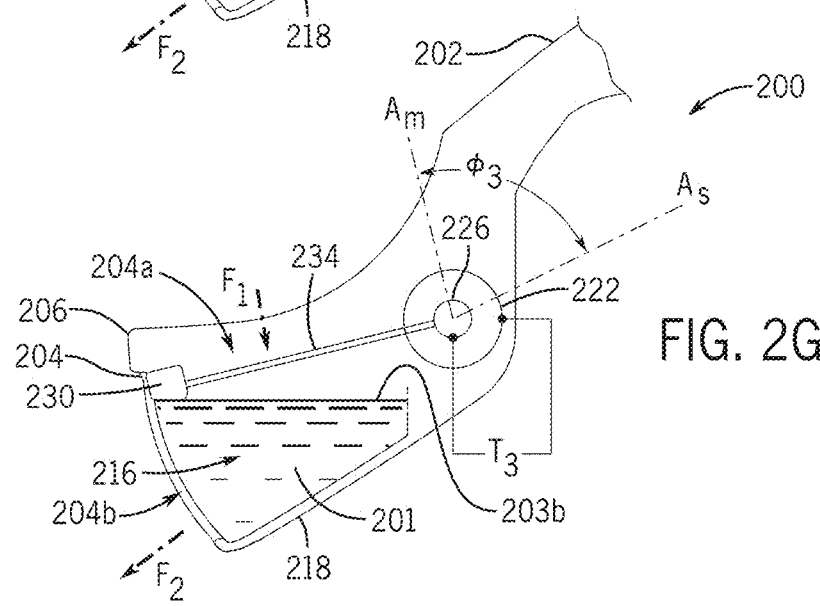
FIG. 2G depicts the voiding device of FIG. 2A in a third configuration.

As illustrated in FIG. 2A-2D, and particularly in FIGS. 2E-2G, for example, as the level of urine or other fluid increases in the flow chamber 204, the float 230 rises within the flow chamber 204. Similarly, as the level of urine decreases in the flow chamber 204, the float 230 falls within the flow chamber 204. As the float 230 rises and falls, the magnet 226 is rotated relative to the displacement sensor 222 via the first and second arms 234a, 234b about a pivot axis 232. The displacement sensor 222 detects an angular position $\phi$ of the magnet 226 using its magnetic flux, and the fluid level in the flow chamber 204 can be determined from the angular position data of the magnet 226, e.g., by using a look-up table that correlates the angular position of the magnet 226 to the position of the float 230, and thus the fluid level in the flow chamber 204.

To illustrate the foregoing, FIGS. 2E-2G show the displacement sensor 222 having a reference direction $A_s$ and the magnet 226 having a reference direction $A_m$. For purposes of illustration, the angular position $\phi$ of the magnet 226 may be defined as an angle bounded by the reference direction $A_s$ and the reference direction $A_m$. As the fill level in the flow chamber 204 increases, the magnet 226 rotates, and as such, the reference direction $A_m$ moves relative to the reference direction $A_s$, thereby indicating a change in the angular position $\phi$ of the magnet 226.

FIGS. 2E-2G show the displacement sensor 222 detecting a distinct magnetic characteristic T for different angular positions of the magnet 226. For example, in the first configuration of FIG. 2E, the displacement sensor 222 may detect a magnetic characteristic $T_1$, which may correspond to the magnetic flux exhibited by the magnet 226 when arranged at an angular position $\phi_1$. The angular position $\phi_1$ may correspond to a position of the float 230 at a bottom-most portion of the flow chamber 204, such as when the flow chamber 204 is empty.

As the flow chamber 204 fills with a fluid (e.g., urine), such as generally from the flow path $F_1$, the float 230 rises, thereby rotating the magnet 226 and allowing the magnet 226 to exhibit a different magnetic characteristic detectable by the displacement sensor 222. To illustrate and with reference to FIG. 2F, the voiding device 200 is shown in a second configuration in which the flow chamber 204 includes urine 201 at a fill level 203a. The float 230 is shown in FIG. 2F in an elevated position from that of FIG. 2E, which corresponds to the fill level 203a of the urine 201. The elevated position of the float 230 at the fill level 203a causes the magnet 226 to rotate for arrangement at an angular position $\phi_2$. At the angular position $\phi_2$ the magnet 226 may exhibit a magnetic characteristic $T_2$ detectable by the displacement sensor 222. In this regard, the displacement sensor 222 detects the magnetic characteristic $T_2$, which may in turn be used by the voiding device 200 (or server, or associated system or device) to determine a fill level of the flow chamber 204 being the fill level 203a shown in FIG. 2F.

As the flow chamber 204 continues to fill with fluid, such as generally from the flow path $F_1$, the float 230 may continue to rise, thereby further rotating the magnet 226 and allowing the magnet 226 to exhibit a different magnetic characteristic detectable by the displacement sensor 222. To illustrate and with reference to FIG. 2G, the voiding device 200 is shown in a third configuration in which the flow chamber 204 includes urine 201 at a subsequent fill level 203b. The float 230 is shown in FIG. 2G in an elevated position from that of FIG. 2F, which corresponds to the subsequent fill level 203b of the urine 201. The elevated position of the float 230 at the subsequent fill level 203b causes the magnet 226 to rotate for arrangement at an angular position $\phi_3$. At the angular position $\phi_3$ the magnet 226 may exhibit a magnetic characteristic-$T_3$ detectable by the displacement sensor 222. In this regard, the displacement sensor 222 may detect the magnetic characteristic $T_3$, which may in turn be used by the voiding device 200 (or associated system or device) to determine a fill level of the flow chamber 204 being the subsequent fill level 203b shown in FIG. 2G.

The urinary flow rate of the patient can be determined using the fluid level information (e.g., by calculating changes in the fluid level based on a given outflow rate out of the flow chamber 204, such as the outflow rate of flow along the flow path F2). The fluid level also can be converted to a total volume collected by the voiding device 200 (e.g., by integrating the flow rate curve over the total time period of patient use), or in other words the total volume of urine evacuated or voided by the patient. The fluid level, in addition to pitch and/or roll values, detected by validation sensor 260 are used as inputs to a multi-dimensional lookup table to determine retained volume and outflow rate. For example, the calculation/process may be: (pitch, roll (optional), fluid level)=>[lookup table]=>(retained volume, outflow rate).

Figure 2H:
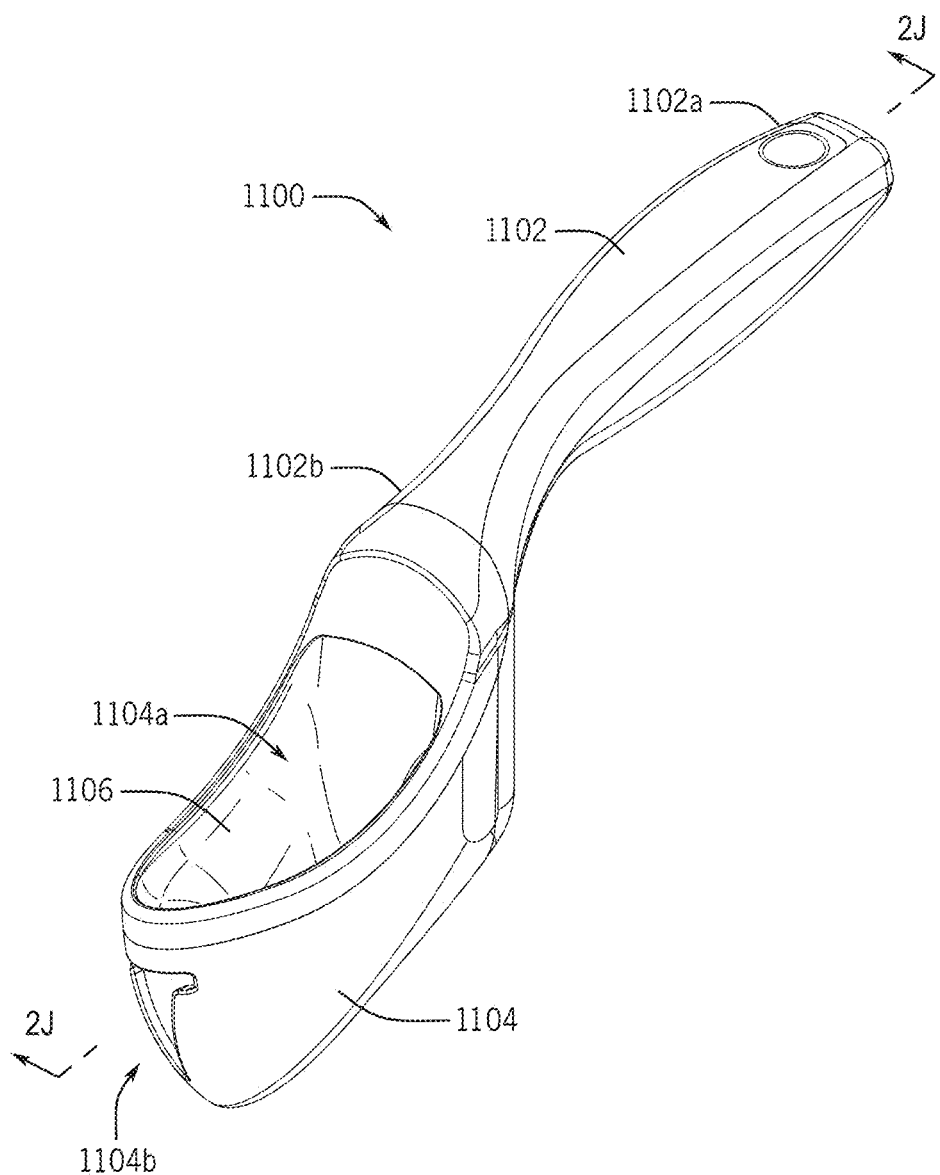
FIG. 2H is a perspective view of another example of a voiding device.
Figure 2I:
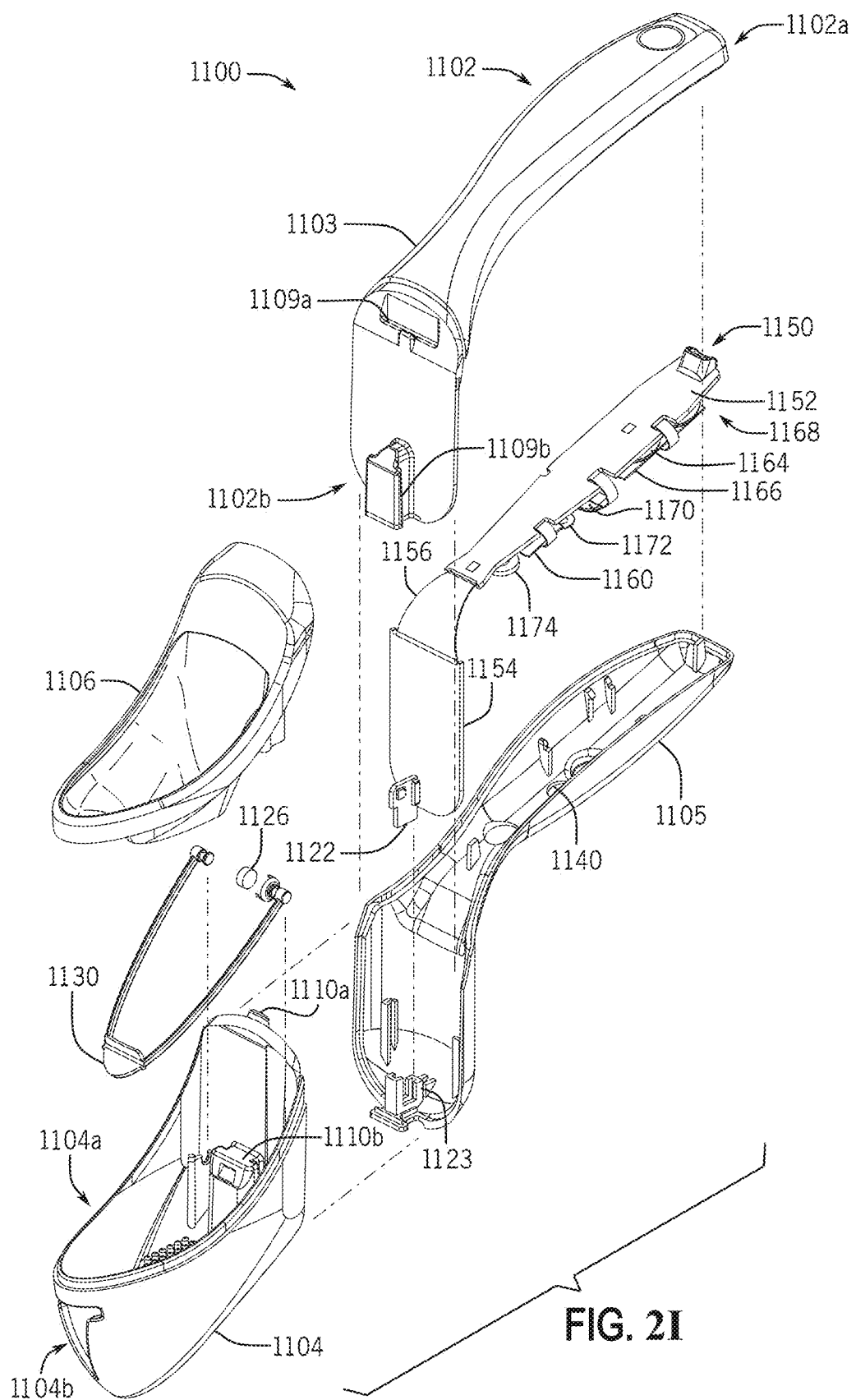
FIG. 2I is a partially exploded perspective view of an example of the voiding device of FIG. 2H.
Figure 2J:
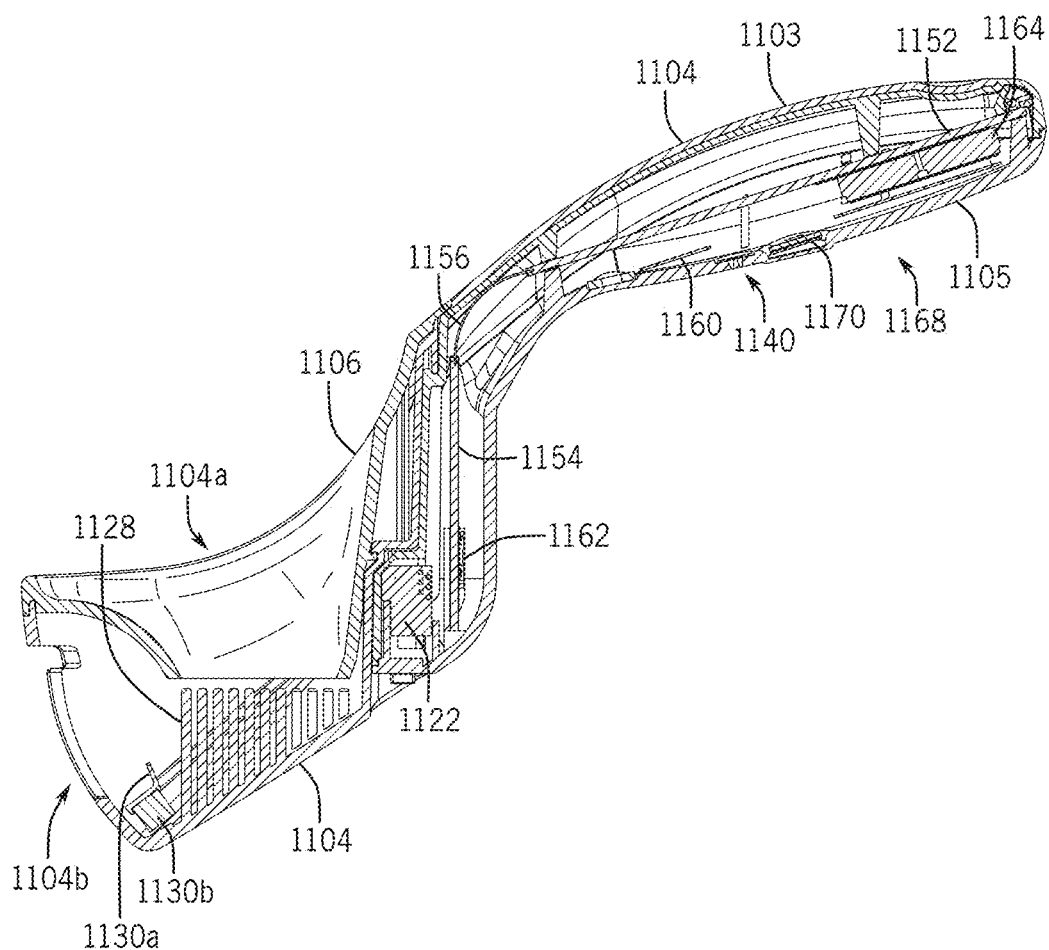
FIG. 2J is a section view of an example of a voiding device, taken along line 2J-2J of FIG. 2H.

FIGS. 2H-2J illustrate another example of a voiding device 1100 including energy dissipation features 1128. The energy dissipation features 1128 are shown positioned substantially within the flow chamber 1104. At least a portion of the energy dissipation features 1128 may be concealed by the funnel 1106 and at least another portion of the energy dissipation features 1128 may be visible and/or along or within the inlet 1104a. Broadly, the energy dissipation features 1128 may define a physical obstacle or obstruction for a flow of urine entering the flow chamber 1104 through the inlet 1104a. The energy dissipation features 1128 may have a size, shape, and contour that dissipates energy, e.g., kinetic energy, from the flow of urine. While many shapes are possible, in the example of FIGS. 2H-2J, the energy dissipation features are shown as a collection of elongated cylinders. The elongated cylinders may generally extend from a bottom of the flow chamber 1104 toward the inlet 1104a. At the bottom of the flow chamber 1104, the elongated cylinders may generally be fixed, whereas near to the inlet 1104a each of the elongated cylinders may have a free end, allowed to deform, flex, sway, and so on. The elongated cylinders are separated from one another, thereby allowing flow among the collection of cylinders. In some cases, the elongated cylinders may have a taper or other contour that changes along a height of the cylinder.

The energy dissipation feature 1128 may facilitate urine level and flow detection. For example, the energy dissipation features 1128 may help reduce turbulent flow within the flow chamber 1104, for example, such as that which may be caused by a fluid flow impacting a stationary volume of fluid. In some cases, the energy dissipation features 1128 may also help mitigate fluid exit through the inlet 1104a. For example, the energy dissipation features 1128 may reduce kinetic energy of a flow of urine in a manner that arrests stray flow from exiting the voiding device 1100 through the inlet 1104a, thereby facilitating smooth or uninterrupted operation of float 1130 and associated components.

Figure 2K:
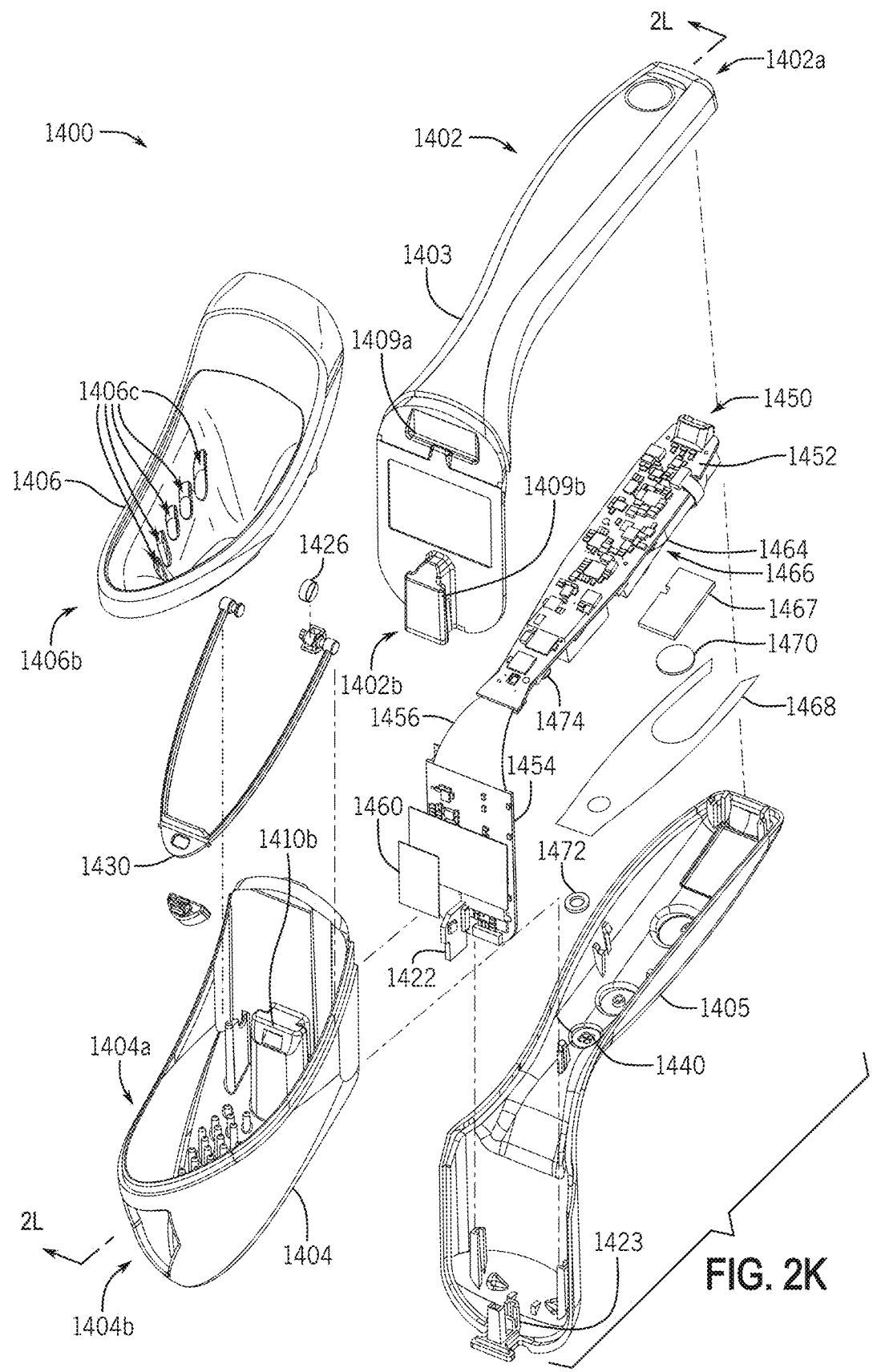
FIG. 2K is a partially exploded perspective view of an example of a voiding device.
Figure 2L:
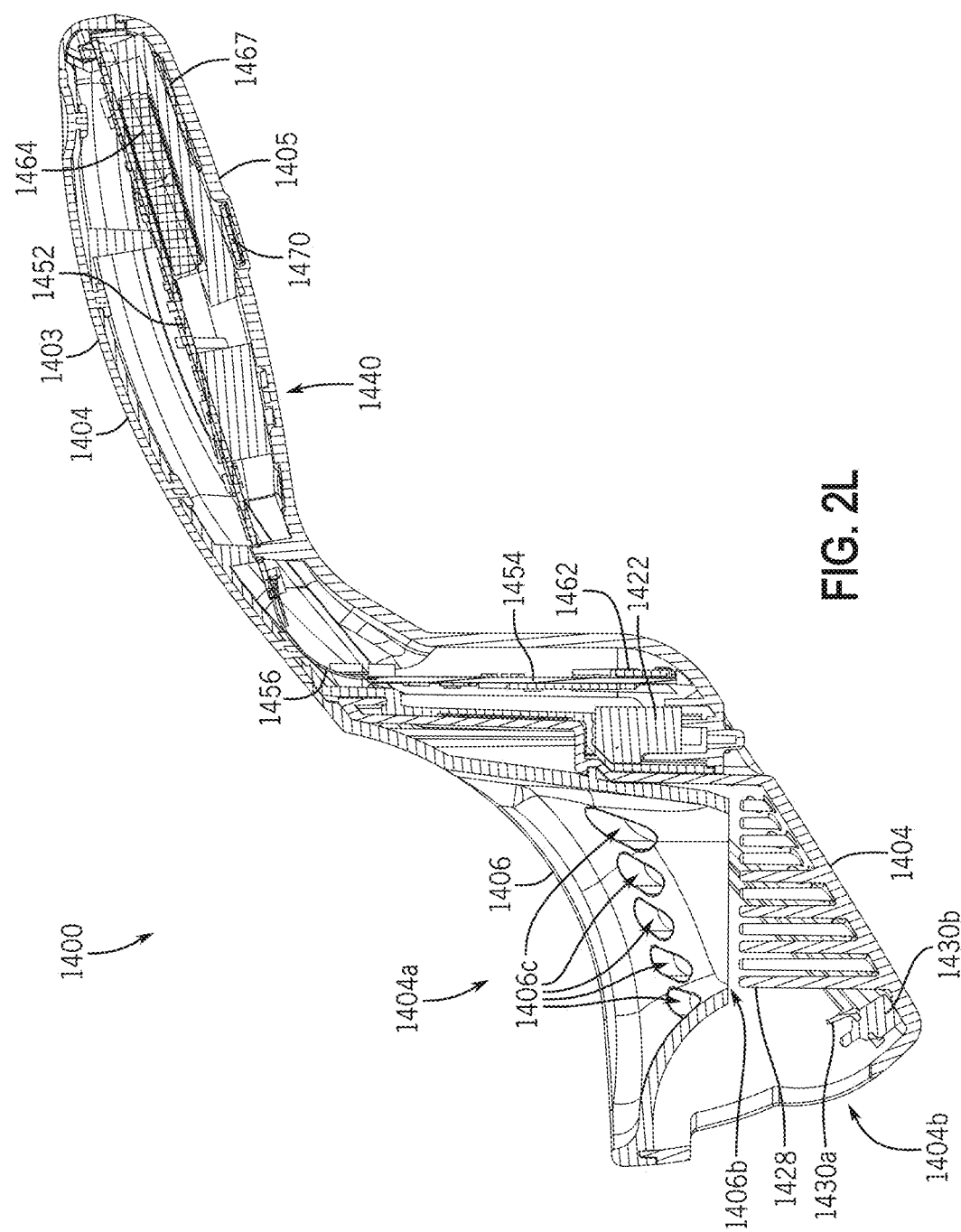
FIG. 2L is a section view of an example of a voiding device, taken along line 2L-2L of FIG. 2K.

With reference to FIGS. 2K-2L, another voiding device 1400 is shown. FIG. 2K is an exploded view of the voiding device 1400, and FIG. 2L is a cross-sectional view of the voiding device 1400, taken along line 2L-2L of FIG. 2K.

As illustrated in FIGS. 2K-2L the voiding device 1400 includes a handle 1402, a bowl or flow chamber 1404, and a funnel 1406. The funnel 1406 includes one or more funnel inlets to allow fluid to pass from the funnel 1406 into the flow chamber 1404. The funnel inlets may be of any suitable shape and number to allow a smooth flow of fluid from the funnel 1406 into the flow chamber 1404. The funnel inlets may be in one configuration for male patients, and in a different configuration for female patients. In one example, the funnel 1406 has a primary funnel inlet 1406b. In another example, the funnel 1406 includes one or more secondary inlets 1406c.

The voiding device 1400 generally includes the same or similar components and operates in the same or similar manner as the voiding device 200 and 1100 and thus the descriptions of the voiding device 200, and/or the voiding device 1100 are applicable to the voiding device 1400. In this regard, substantially analogous to the examples of the voiding device 1100 described above, the voiding device 1400 of FIGS. 2K-2L further includes: a proximal portion 1402a, a distal portion 1402b, a top shell 1403, an inlet 1404a, an outlet 1404b, a bottom shell 1405, a handle groove 1409a, a handle tongue 1409b, a flow chamber tongue, a flow chamber groove 1410b, a sensor 1422, a sensor receiving feature 1423, energy dissipation features 1428, a magnet 1426, a float 1430, a structural member 1430a, a buoyant member 1430b, a vent 1440, electronics 1450, a first printed circuit board 1452, a second printed circuit board 1454, flex connectors 1456, an RFID feature 1460, a SIM feature 1462, a battery 1464, an antenna 1466, an NFC feature 1467, a proximity sensor 1468, a charging coil 1470, a vent disc 1472, other electrical/mechanical components 1474; redundant explanation of which is omitted here for clarity. The structural member 1430a may be adapted to maintain accurate readings from the sensor 1422 during high periods of fluid flow.

Figure 2M:
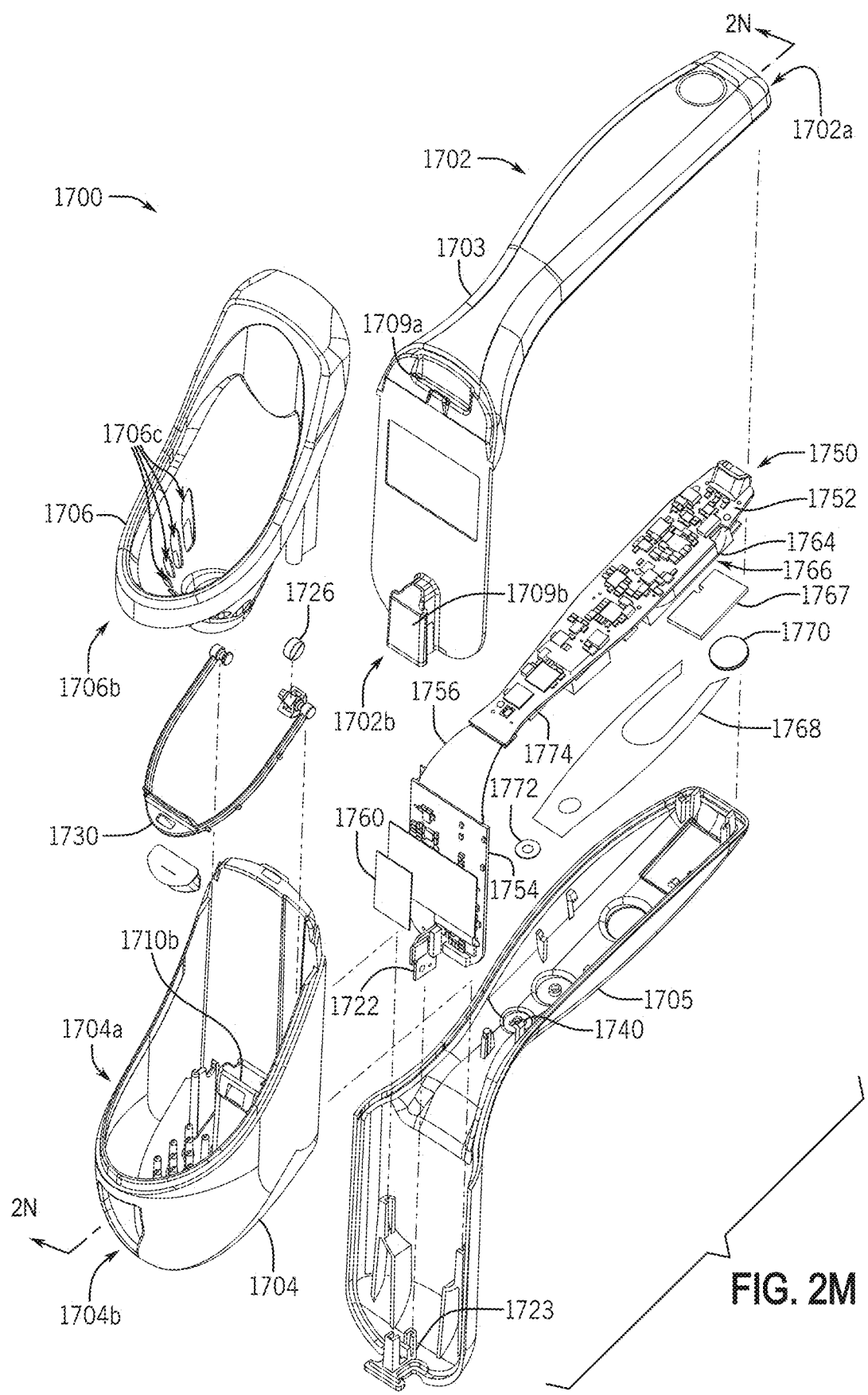
FIG. 2M is an exploded view of an alternative uroflowmeter in accordance with various examples of the present disclosure.
Figure 2N:
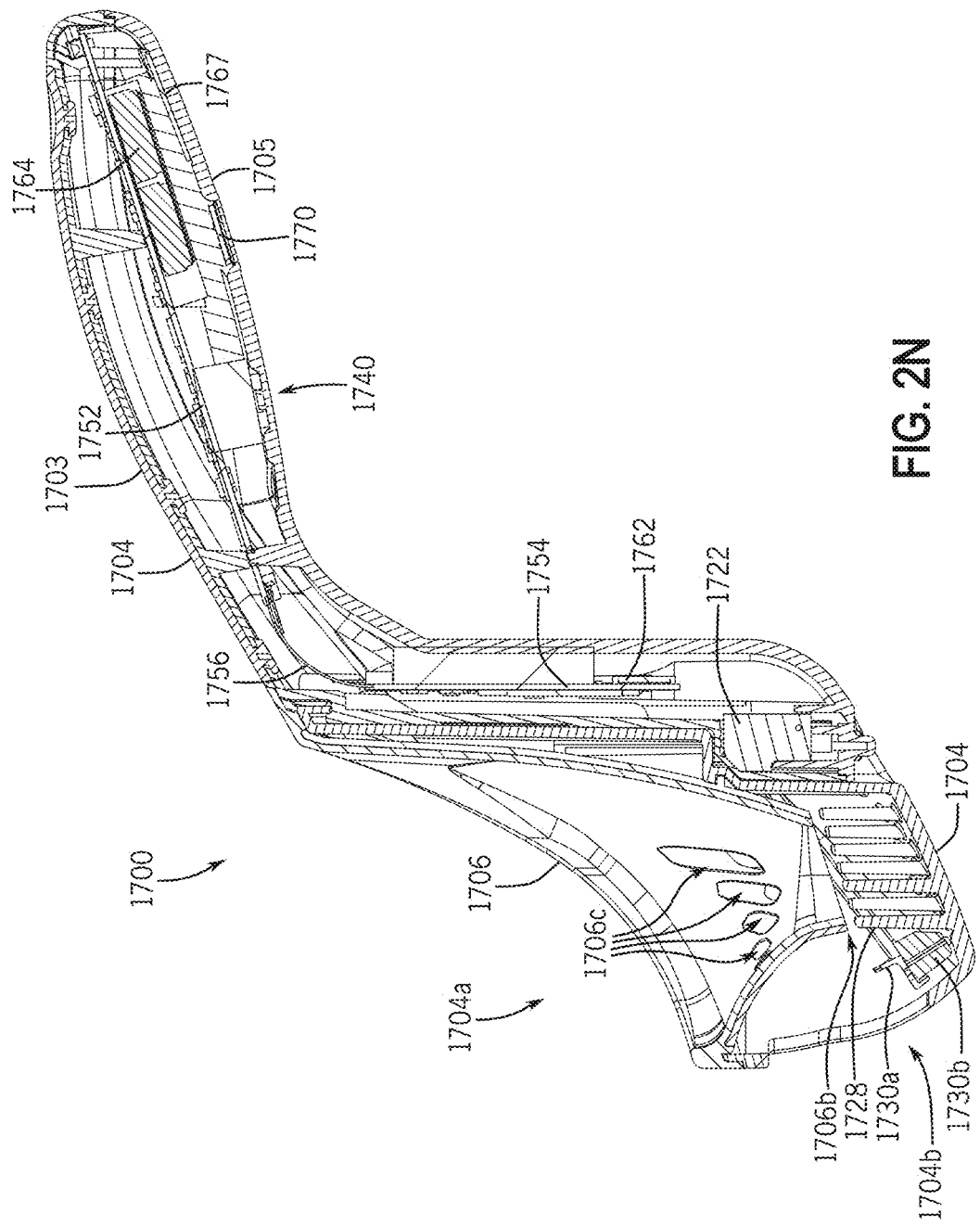
FIG. 2N is a cross-sectional view of the uroflowmeter of FIG. 2M taken along line 2N-2N in accordance with various examples of the present disclosure.

With reference to FIGS. 2M-2P, a uroflowmeter 1700 is shown. FIG. 2M is an exploded view of the uroflowmeter 1700, and FIG. 2N is a cross-sectional view of the uroflowmeter 1700, taken along line 37-37 of FIG. 2M. FIG. 2O is a partial exploded view of the uroflowmeter 1700 of FIG. 2M. FIG. 2P is a partial detailed view of the attachment between the flow chamber 1704 and the handle 1702 of the uroflowmeter 1700.

As illustrated in FIGS. 2M-2P, the uroflowmeter 1700 includes a handle 1702, a bowl or flow chamber 1704, and a funnel 1706. The funnel 1706 includes one or more funnel outlets to allow fluid to pass from the funnel 1706 into the flow chamber 1704. The funnel outlets may be of any suitable shape and number to allow a smooth flow of fluid from the funnel 1706 into the flow chamber 1704. The funnel outlets may be in one configuration for male patients, and in a different configuration for female patients. In one example, the funnel 1706 has a primary funnel outlet 1706b. In another example, the funnel 1706 includes one or more secondary outlets 1706c. In one example, the funnel includes five secondary outlets.

The uroflowmeter 1700 generally includes the same or similar components and operates in the same or similar manner as the uroflowmeter 200, 1100, and 1400, and thus the descriptions of the uroflowmeter 200, the uroflowmeter 1100, and/or the uroflowmeter 1400, are applicable to the uroflowmeter 1700. In this regard, substantially analogous to the examples of the uroflowmeter 200, 1100, and/or 1400 described above, the uroflowmeter 1700 of FIGS. 2M-2P further includes: a proximal portion 1702a, a distal portion 1702b, a top shell 1703, an inlet 1704a, an outlet 1704b, a bottom shell 1705, a handle groove 1709a, a handle tongue 1709b, a flow chamber tongue, a flow chamber groove 1710b, a sensor 1722, a sensor receiving feature 1723, energy dissipation features 1728, a magnet 1726, a float 1730, a structural member 1730a, a buoyant member 1730b, a vent 1740, electronics 1750, a first printed circuit board 1752, a second printed circuit board 1754, flex connectors 1756, an RFID feature 1760, a SIM feature 1762, a battery 1764, an antenna 1766, an NFC feature 1767, a proximity sensor 1768, a charging coil 1770, a vent disc 1772, other electrical/mechanical components 1774; redundant explanation of which is omitted here for clarity. The structural member 1730a may be adapted to maintain accurate readings from the sensor 1722 during high periods of fluid flow.

FIG. 2O illustrates the voiding device of FIG. 2M, where the flow chamber 1704 of the uroflowmeter 1700 is removably attached to the handle 1702, thereby allowing the flow chamber 1704 to be disposed of after patient use. In various examples, the uroflowmeter 1700 does not include a disposable funnel. As illustrated in FIGS. 2O-2P, the flow chamber 1704 may have one or more grasping features 1778a and 1778b that grasp cooperating features of the handle 1702. In one example, the grasping features 1778a, 1778b are springs including a cantilevered section 1784 separated from the body of the flow chamber 1704 by a clearance 1788. In the example, the grasping features 1778a, 1778b include a tang 1786. When the grasping features 1778a, 1778b are in a relaxed position, the tangs 1786 grasp corresponding features of the handle, preventing a user from decoupling the flow chamber 1704 and the handle 1702. The flow chamber 1704 and the handle 1702 may be decoupled with the use of a key 1776. The key may be available to medical professionals, and not available to users. The key 1776 may include a handle 1792 connected to a shaft 1790, a pivot recess 1782 defined at one of the shaft 1790, and one or more decouplers 1780a, 1780b disposed radially about the pivot recess 1782. The one or more decouplers 1780a, 1780b cooperate with the one or more grasping features 1778a, 1778b to allow a medical professional to decouple the flow chamber 1704 and the handle 1702 of the uroflowmeter 1700. In one example, a medical professional inserts the key 1776 into the uroflowmeter 1700 such that the pivot recess 1782 cooperates with a pin in the uroflowmeter 1700. The medical professional may rotate, or twist the key 1776, causing the one or more decouplers 1780a, 1780b to press against the one or more grasping features 1778a, 1778b, flexing the cantilevered section 1784 and causing the tang 1786 to disengage from the handle 1702. The medical professional may then slide the flow chamber 1704 away from the handle 1702. The medical professional may then dispose of, or disinfect and process for reuse, the flow chamber 1704. The medical professional may then reprocess the handle 1702 for reuse as previously described. The key 1776 and associated features of the handle 1702 that prevent user decoupling of the handle 1702 and the flow chamber 1704 are shown with respect to the example of the voiding device 1700, in FIGS. 2M-2O for example and illustration purposes. The key and these or similar features are equally applicable to, and may be included in, any voiding device disclosed herein, including the voiding device 200, 1100, 1400, and/or 1700.

Figure 3A:
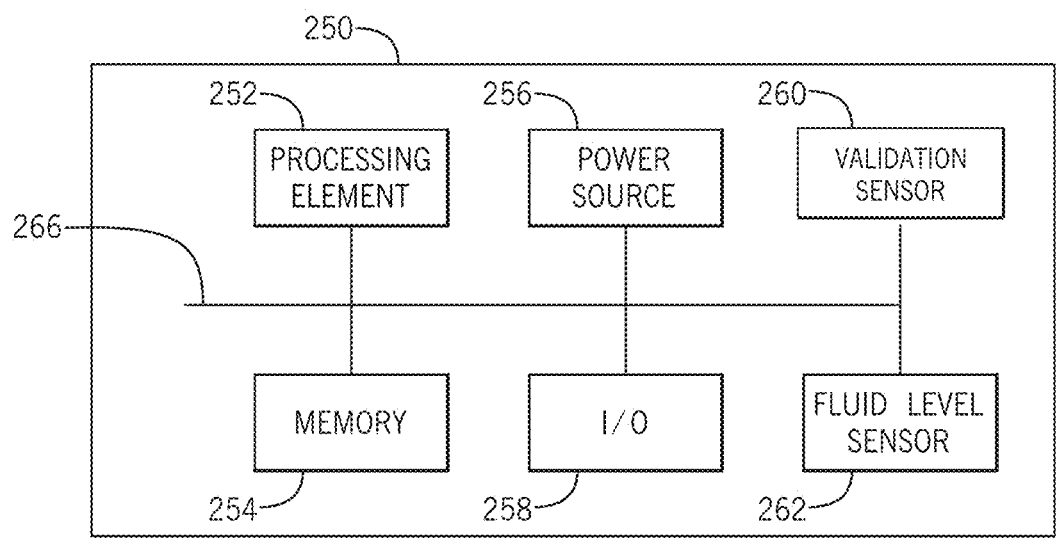
FIG. 3A is a simplified block diagram of the electronics in an example of a voiding device.

FIG. 3A is a simplified block diagram of additional components embedded with or otherwise coupled to the voiding device 200. These components may be enclosed within the handle 202 or in another location within the housing of the device. Referring to FIG. 3A, the voiding device 200 may include one or more device processing elements 252, one or more memory components 254, a power source 256, an input/output (I/O) interface 258, one or more validation sensors 260, one or more fluid level sensors 262. The device processing element 252 may contain a clock. The voiding device 200 may include other components typically found in computing systems, such as communication interfaces and other sensors, among others. For example, the voiding device 200 may contain a cellular telephone network modem capable of communicating directly with a cellular network. Each element of the voiding device 200 may be in communication with each of the other elements of the voiding device 200 via one or more system buses 266, wirelessly, or the like. The voiding device 200 can transfer data to various computing devices (e.g., the user mobile device 108, the healthcare provider device 109, the report device 110, the third party device 103, and/or server 112).

At least some of the components or elements of the voiding device 200 may be housed in the voiding device 200. For example, one or more of the device processing elements 252, memory components 254, power source 256, input/output (I/O) interface 258, validation sensors 260, and fluid level sensors 262 may be positioned in or received in the voiding device 200. For example, one or more of the device processing elements 252, memory components 254, power source 256, input/output (I/O) interface 258, the fluid level sensors 262, and validation sensors 260 are housed or received in the handle 202, and the magnet 226 is received in the flow chamber 204. The device processing elements 252 may be associated with a printed circuit board 270 and the printed circuit board 270 may be received in the handle 202 of the voiding device 200 as illustrated in FIG. 2C, for example.

Another example of a voiding device 1100 is illustrated in FIGS. 2H-2J. The voiding device 1100 may include electronics 1150. While many different components may be used to implement the operations of the voiding device, as described herein, FIGS. 2I and 2J present a sample arrangement of components that define or are associated with the electronics 1150. Broadly, the electronics 1150 may include a first printed circuit board 1152 and a second printed circuit board 1154. The first printed circuit board 1152 and the second printed circuit board 1154 may be connected to one another by flex connectors 1156. In the example of FIGS. 2I and 2J, the first printed circuit board 1152 may be positioned within the handle 1102 near a proximal portion 1102a and the second printed circuit board 1154 may be positioned within the handle 1102 near a distal portion 1102b.

This dual circuit board arrangement may facilitate arranging components at different locations of the handle 1102 based on a target function. For example, the first printed circuit board 1152 may be positioned away from the flow chamber 1104 and be associated with battery operation, charging, and so on, whereas the second circuit board 1154 may be positioned closer to the flow chamber 1104 and be associated with sensors and operations of the flow chamber 1104. While the example of FIGS. 2H-2J shows the first printed circuit board 1152 and the second printed circuit board 1154 as separate circuit boards that are connected by the flexible connectors 1156, in other examples, other configurations are possible. For example, the first print circuit board 1152 and the second printed circuit board 1154 may be portions of a single circuit board, such as a hybrid rigid/flexible circuit assembly having rigid portions and flexible portions. This single component or single assembly approach may facilitate reliability by reducing connections, and/or also reduce manufacturing costs.

In the example of FIGS. 2H-2J, the first printed circuit board 1152 may be associated with at least an RFID element 1160, a battery 1164, an antenna 1166, a proximity sensor 1168, a charging coil 1170, a vent disc 1172, and/or other electrical mechanical components 1174. Further, the second printed circuit board 1154 may be associated with at least the sensor 1122 and a SIM ("Subscriber Identity Module") feature 1162. In other examples, other arrangements of components are contemplated to execute the functions of the uroflowmeter described herein.

In some examples, the RFID element 1160 or other near field radio wave transmission device, identification beacon, or the like, may facilitate reprocessing and tracking of the handle 1102. For example, the RFID element 1160 may include identifying information for the handle 1102, e.g., an identification number or data or the like. The identifying information may be used to associate the handle 1102 with a particular patient or a particular use of the voiding device 1100. The identifying information may also be used to track the handle 1102 throughout reprocessing, including tracking the handle 1102 throughout a sanitization process. The identifying information may also facilitate real-time updates of inventory, such as being used to determine which units are in a condition for new patient-use, e.g., the units that have been reset to factory standards, sterilized, or otherwise processed as desired. Dynamic adjustments can therefore be made to facilitate inventory level maintenance, including initiating a resupply of handles, or other components, when the inventory drops below a threshold. The resupply of handles may happen automatically. For example, by periodically or randomly polling a supply of handles, such as with an RFID scanner, responses from the RFID or other element can be used to easily determine supply levels and categories of handles (e.g., awaiting processing, processed, etc.).

Reprocessing may be facilitated by Global Positioning System ("GPS") localization of the handle 1102. In some examples, the handle 1102 may include a GPS assembly or other location sensor or element to facilitate determining a coordinate and/or relative position of the handle 1102. As described herein, the handle 1102 may be communicatively coupled with various remote computing systems. The GPS assembly of the handle 1102 may therefore determine information corresponding to a position of the handle 1102, which is in turn transmitted wirelessly to the remote computing system. The remote computing system may track the location of the handle 1102 and determine the handle 1102 being at one or more reprocessing, patient, healthcare provider, or other locations. The GPS assembly may be used to dynamically and automatically provide location information to the server, both during patient use and post processing.

This may allow data to be automatically input into a patient use diary or other associated application that may provide additional metadata to be stored with patient voids. The GPS assembly may communicate with the U.S. Global Positioning System, the Russian GLONASS system, or other satellite-based positioning systems. The handle may also determine a coordinate and/or relative position using cellular network triangulation methods.

Referring to FIG. 3A, the one or more device processing elements 252 are substantially any type of electronic device capable of processing, receiving, and/or transmitting instructions. For example, the device processing elements 252 may be a microprocessor or a microcontroller. Additionally, it should be noted that select components of the voiding device 200 may be controlled by a first device processing element 252 and other components may be controlled by a second device processing element 252, where the first and second device processing elements 252 may or may not be in communication with each other. Additionally or alternatively, select data processing steps or processes may be performed by one device processing element 252 with other data processing steps performed by different device processing elements 252, where the different device processing elements 252 may or may not be in communication with each other.

The one or more memory components 254 may store electronic data used by the voiding device 200 to store instructions for the device processing element 252, as well as to store data collected by the fluid level sensor 262, for example. In some examples, the one or more memory components 254 may be one or more magnetic hard disk drives, solid state drives, magneto optical memory, flash memory, electrically erasable programmable read-only memory ("EEPROM"), erasable programmable read-only memory ("EPROM"), ferromagnetic RAM, holographic memory, printed ferromagnetic memory, or non-volatile memory. In other examples, memory 254 may be any volatile computer readable media device that requires power to maintain its memory state. In one example, memory 254 is random access memory ("RAM"). Other examples may include dynamic RAM, and static RAM, or a combination of one or more types of memory components.

The power source 256 provides power to select components of the voiding device 200. Depending on the particular application, the power source 256 may be a battery (for example, battery 272 received in the handle 202 of the voiding device 200 as illustrated in FIG. 2C), a power cord, or any other element that transmits electrical power to the components 250 of the voiding device 200. As illustrated in FIG. 2C, the battery 272 may be accessible via a removable cover 276, which may be located on an underside of the handle 202. The cover 276 may be attached to the handle 202 via one or more fasteners 278. Alternately, as illustrated for example in FIGS. 2I-2J, the handle 1102 of an example of a voiding device 1100 may include an upper 1103 and lower 1105 unitary shell, housing an inaccessible battery 1164. The battery 272 or 1164 may be rechargeable by power cord or inductive charging station 114 shown for example in FIG. 18. The device processing element 252 may determine a status of the handheld voiding device, receive information from the charging station via the I/O interface 258; and indicate readiness for continued use through an indicator, for example, an LED.

The clock is any device capable of keeping time or otherwise measuring time or date data. In one example, clock is a piezoelectric crystal oscillator. In other examples, clock is an atomic clock, radio receiver in communication with a time standard, or any other electrical or mechanical device, and outputting time or date data. In another example, the clock is integrated into the device processing element 252.

The voiding device 200 has a determinable outflow rate. For example, based on the level of urine within the flow chamber 204, the outflow rate of the voiding device 200 can be determined at a given point in time. As illustrated in FIG. 2A, in one example, the outlet 204b is formed as a vertically-oriented slot. In various examples, the width of the outlet 204b increases as the outlet 204b progresses upwardly from the bottom wall 218 toward the rim 210 of the flow chamber 204 (e.g., forming a triangularly-shaped opening). The slot allows an increasing outflow rate of the voiding device 200 as the fluid level increases within the flow chamber 204 to ensure urine does not overflow out of the flow chamber 204. The outlet 204b restricts urine flow out at low flow rates to improve "low-flow" sensitivity of the system, and increases flow out for higher flow rates (i.e., where less sensitivity is required) to prevent overflow or backflow conditions).

FIGS. 2H-2J illustrate another example of a voiding device 1100. The outlet of the voiding device 1100 can be defined by a T-shaped slot. Further, the examples of a voiding device 1100 FIGS. 2H-2J shows the voiding device 1100 having the outlet 1104b. The outlet 1104b is generally defined by a T-shaped slot extending through an exterior wall of the flow chamber 1104. The outlet 1104b generally increases a volumetric range of the flow chamber 1104, across which high accuracy flow measurements may be obtained. For example, the outlet 1104b generally restricts flow from exiting the flow chamber 1104 when the flow chamber 1104 includes relatively little fluid. The structural member 1130a may be adapted to maintain accurate readings from the sensor 1122 during high periods of fluid flow. In another example, the float 1130b generally restricts flow from exiting the flow chamber 1104 when the flow chamber 1104 includes relatively little fluid. This may correspond to a lower flow rate of urine, and therefore the restriction of fluid exiting the flow chamber 1104 helps facilitate or increase the sensitivity of associated flow measurements in this configuration. As the volume of fluid in the flow chamber 1104 increases, the outlet 1104b reduces its fluid restriction, allowing an increasingly greater amount of fluid to exit. Alternately, as the volume of fluid in the flow chamber 1104 increases, the float 1130b rises, thereby allowing increased fluid to exit through the outlet 1104b. This may correspond to a higher flow rate of urine, at which less sensitivity in flow rate measurement may be required. The outlet 1104b also includes an elongated opening positioned above and connected to the triangular-shaped opening. This elongated opening may mitigate overflow or backflow conditions, for example, by allowing for additional fluid release when the flow chamber 1104 approaches capacity. It will be appreciated that the shape and arrangement of the outlet 1104b is depicted for purposes of illustration. In other examples, other shapes and arrangements of outlets are possible to facilitate the various functions of the voiding device 1100 described herein.

The voiding device 200 measures one or more parameters of a patient's urinary voiding. For example, the flow chamber 204 can collect urine and measure urine parameters by one or more sensors. In one example, the voiding device 200 determines the date and time of a void, voided volume, average void flow rate, voiding time, flow time, maximum flow rate, and the time to maximum flow rate.

The I/O interface 258 provides communication to and from the voiding device 200 to exterior devices and/or the user. The I/O interface 258 may include one or more input buttons, a communication interface (such as Wi-Fi®, Ethernet, Bluetooth®, NFC, RFID, cellular, infrared or other optical communications, or the like), communication components (such as universal serial bus (USB) ports/cables), or the like. In various examples, the I/O interface 258 transmits sensor data from the voiding device 200 to a remote computing device, such as a remote server 112. The I/O interface may also transmit data to a healthcare provider device 109, a report device 110, a third party device 103, a user mobile device 108, or a charging station 114.

The one or more validation sensors 260 may be substantially any type of electronic device capable of measuring the orientation value of the voiding device 200. For example, the one or more validation sensors 260 may be an orientation sensor such as a gyroscope or an accelerometer for measuring the orientation of the voiding device 200. Additionally or alternatively, the one or more validation sensors 260 may be a capacitive (or capacitance), or resistive sensor for proximity detection. For example, a capacitance sensor in the handle may determine that the handle is held in the user's hand and may measure the device proximity to the human body. In another example, the device processing element 252 may detect the user's grip through a validation sensor 260, such as a capacitance sensor, and infer the orientation of the voiding device 200 from the user's grip.

The validation sensors 260 may cooperate to automatically power the device on/off. In various examples, both an accelerometer and a capacitive sensor are used to activate the voiding device 200 automatically (e.g., the device is activated when the accelerometer detects motion and the user's grasp is detected by the capacitive sensor.). For example, the voiding device 200 may provide power to an accelerometer when the voiding device 200 is in an otherwise idle state. When the accelerometer detects motion, it may cause the proximity sensor to receive power, enabling the proximity sensor to detect the presence of a user's touch. If both the accelerometer and the proximity sensor detect conditions consistent with an impending void, such as a user's grasp on the handle and motion consistent with orienting a device into a particular position, the voiding device 200 may then power the device processing element 252, preparing the voiding device 200 to receive flow data. In other instances, detection of a value over a particular threshold or within a selected range by either the accelerometer or the proximity sensor may be sufficient to activate the voiding device 200.

The one or more validation sensors 260 may measure the orientation of the voiding device 200, and the orientation data may be stored in the memory 254. In various examples, the voiding device 200 automatically turns on depending on the orientation of the voiding device 200, e.g., with a capacitive sensor. For example, when the voiding device 200 is positioned in a proper orientation for use as detected by the one or more validation sensors 260, the one or more device processing elements 252 may supply power to the voiding device 200 via the battery 272, thereby turning on the voiding device 200 for use. Powering on the device when it is in the correct orientation may happen automatically or may be facilitated via a power button. For example, the voiding device 200 may include a power button 279 (see, e.g., FIGS. 2A and 2B) to permit the user to manually turn the voiding device 200 on or off.

In other examples of the voiding device 200, an LED light may illuminate when the device is in the correct, desired, or optimal position relative to the patient's body. Additionally or alternatively, the voiding device 200 may include a display, such as an LED display. The LED display may be integrated with the handle of the voiding device 200 and coupled with the one or more validation sensors 260 and/or other sensors. The display may indicate a current or instantaneous orientation of the voiding device 200, including a pitch and/or roll condition or value. As described herein, the voiding device 200 may have a target condition or target orientation that is associated with an optimal operation of one or more components of the voiding device 200, such as the displacement sensor 222. In this regard, the display may indicate the current orientation of the voiding device 200 relative to the target condition or orientation. When the current orientation matches and/or is within an acceptable range of the target, the voiding device 200 may be in a state in which it receives a flow of a patient's urine.

Figure 3B:
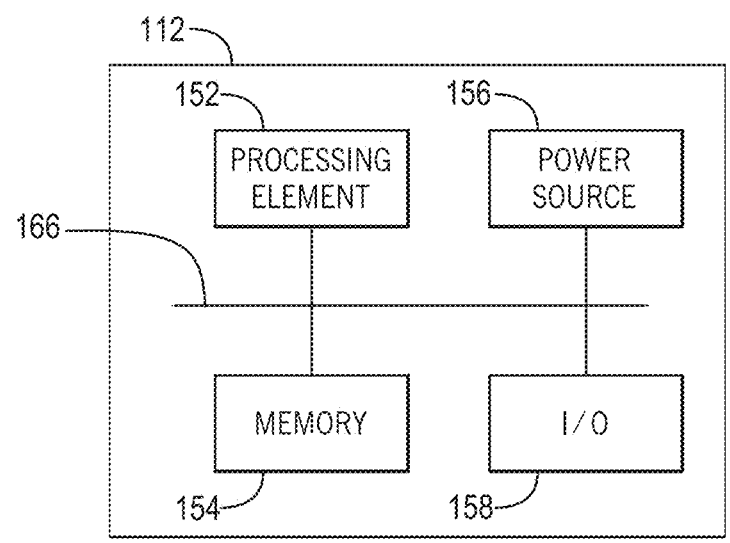
FIG. 3B is a simplified block diagram of the electronics in an example of a server.

FIG. 3B is a simplified block diagram of additional components within or associated with a server 112. The server 112 may contain one or more server processing elements 152, a power source 156, memory 154, and one or more I/O interfaces 158. Each element of the server 112 may be connected via one or more system buses 166.

Referring to FIG. 3B, the one or more server processing elements 152 are substantially any type of electronic device capable of processing, receiving, and/or transmitting instructions. For example, the server processing elements 152 may be a microprocessor or a microcontroller. Additionally, it should be noted that select components of the server 112 may be controlled by a first server processing element 152 and other components may be controlled by a second or subsequent server processing element 152, where the first and second server processing elements 152 may or may not be in communication with each other. Additionally or alternatively, select data processing steps or processes may be performed by one server processing element 152 with other data processing steps performed by different server processing elements 152, where the different server processing elements 152 may or may not be in communication with each other. Additionally, some data processing steps or processes may be performed by one or more device processing elements 252 and others performed by one or more server processing elements 152, where the respective processing elements may or may not be in communication with one another.

The one or more memory components 154 may store electronic data used by the server processing element 152, as well as to store data collected by the voiding devices 200, the user mobile devices 108, the healthcare provider devices 109, the report devices 110, and/or the third party devices 103, for example. The example memory devices 254 described for the voiding devices 200 may also serve as example memory devices 154. The memory devices 154 may be the same types of devices as memory 254 of the voiding device 200, or they may be different.

The power source 156 provides power to select components of the server 112. Depending on the particular application, the power source 156 may be a power cord, alternating current to direct current rectifier, transformer, or any other element transmitting electrical power to the server 112. The power source 156 may include a backup battery to keep the server powered in the event of a power grid failure.

The I/O interface 158 provides communication to and from the server 112 to exterior devices, and the network 102. The I/O interface 158 may include a communication interface (such as Wi-Fi®, Ethernet, Bluetooth®, NFC, RFID, fiber optics, cellular, infrared or other optical communications, or the like), communication components (such as universal serial bus (USB) ports/cables), human interface components (such as a keyboard, mouse, stylus, monitor, touch screen, microphone, speakers), or the like. In various examples, the I/O interface 158 receives sensor data from the voiding device 200, recording it in memory 154 for further processing by the server processing element 152. For example, the server processing element 152, may validate whether the data are associated with a void, process the sensor data to calculate urine flow rate and total volume voided for each urinary event, reprocess the data, store the data, retrieve analyzed data, and/or generating reports. In other examples, summary flow rate calculations are transmitted to the server. In another example, the I/O interface 158 transmits raw data to a server 112, or another device. In another example, the I/O interface transmits filtered data to a server 112, or other device.

Additionally, it should be noted that although various methods and operations are described as being executed by the device processing element 252 on the voiding device 200, some operations may be executed in full or in part on an external processing element, such as on the server 112 with the server processing element 152, or other processing elements associated with the healthcare provider device 109, third party device 103, user mobile device 108, report device 110, or other devices. Discussions of a particular processing element are meant as illustrative only.

Figure 4:
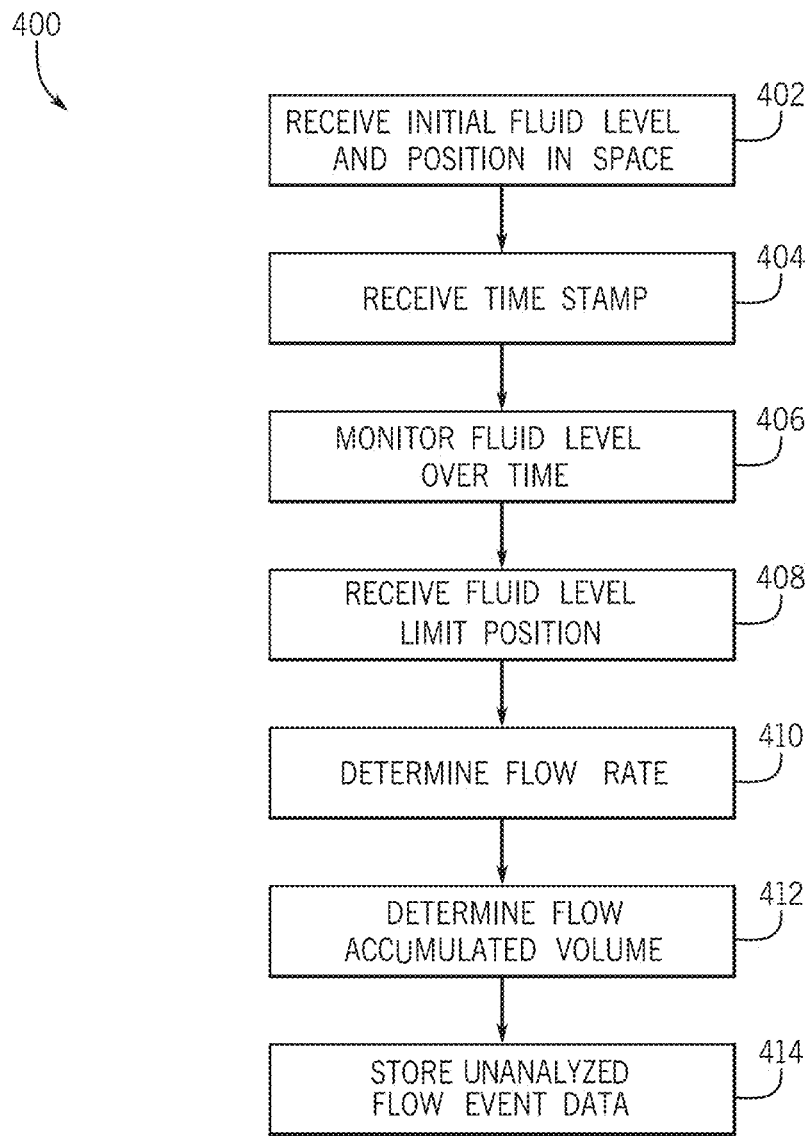
FIG. 4 is a flow chart illustrating a method for capturing flow event data with the voiding device of FIG. 2A.

FIG. 4 discloses a flow chart for a method 400 for determining parameters associated with a flow event detected by the voiding device 200. The method may be executed while a flow event is occurring or after the voiding device 200 has detected that a flow event has occurred and transmits the unanalyzed data to the server 112 or other device via the network for processing. In some instances, the device processing element 252 may perform some analysis on the data, while the server processing element 152 performs other analysis on the data. In some instances, the activation of the method 400 may be determined based on the voiding device 200 being "activated" or otherwise detecting a flow event is about to occur, such as through a user turning the voiding device 200 to an active state, the proximity sensor detecting the grip of the user, and/or the fluid level sensor 262 detecting an increase in the fluid level of the voiding device 200.

The method may begin with operation 402 and the device processing element 252 or server processing element 152 receives or records an initial fluid level in flow chamber 204. In one example, the fluid level corresponds to an angular position $\phi$ of the float 230 of the voiding device 200. For example, the respective processing element receives the float 230 position as indicated by the angular position $\phi_1$ when the flow chamber 204 is substantially empty of fluid, as illustrated in FIG. 2E. The float 230 may be at a lower limit position indicating that the flow chamber 204 is empty and this position is provided to the respective processing element. In another example, the float 230 position is detected at an initial value before use, or is retrieved from the memory 254 as a default initial value. In one example, the position of the float 230 is an angular displacement or position value $\phi$ received from a displacement sensor 222, such a Hall effect sensor. In another example, the position of the float 230 is a linear displacement or position value received from a displacement sensor 222. In another example, the fluid level corresponds to a capacitance value of a capacitive sensor.

Also in operation 402, the device processing element 252 or server processing element 152 receives or records the initial position or orientation of the voiding device 200 in 3D space as detected by the validation sensor 260 indicating the initial pitch value, and optionally the initial roll value, of voiding device 200. In one example, the validation sensor 260 indicates the voiding device 200 is pitched within the flow chamber 204 rotated downward relative to handle 202, about an axis parallel to the pivot axis 232. In another example, the validation sensor 260 indicates the voiding device 200 is pitched with the flow chamber 204 rotated upward relative to handle 202, about an axis parallel to the pivot axis 232. In another example, the validation sensor 260 indicates the voiding device 200 is rolled asymmetrically either direction about an axis perpendicular to the pivot axis 232. The validation sensor 260 may indicate the position of the voiding device 200 in any combination of pitch and/or roll in any direction about any axis. The validation sensor 260 may also indicate the position of the voiding device 200 relative to any three orthogonal axes, or relative to a plane and an axis orthogonal to that plane. The detected positions may be when the voiding device 200 is activated or a short time windows after activation (e.g., 3-5 seconds) that gives time for a user to turn on the voiding device 200 and then begin to void. Alternatively, the initial orientation positions may be pulled from memory corresponding to a typical position of the voiding device 200 during a void and depending on the patient's gender. For example, male patients may have an orientation or pitch and/or roll set to a first value that corresponds to most instances of use. Similarly, female patients may have an orientation or pitch and/or roll value at first release that corresponds to most instances of use. The method 400 may retrieve these values upon activation or may dynamically update the values based on current actual position at activation or first flow.

In operation 404, simultaneously or after the initial float position has been received and one or both of pitch and/or roll are determined, the device processing element 252 or server processing element 152 receives a time stamp corresponding to initial activation or initially detected flow through the voiding device 200. For example, the device processing element 252 can receive time and/or date information from the clock forming a time stamp. In another example, a time stamp is an date and/or time, e.g., "Oct. 8, 2018 6:51:00 PM." The time stamp may be in any format, such as formatted for 12-hours and AM/PM information as above, or formatted for 24 hour information, such as, "Oct. 8, 2018 18:51:00." In another example, the clock accrues elapsed time between flow events. For example, the clock includes a timer that resets to zero once a void event is validated (as discussed below with respect to FIGS. 6 A, 6B), and begins counting the elapsed time until a next validated void event. The clock may account for differences in time zones between a healthcare provider and a patient. For example, the time stamp may be recorded in Greenwich Mean Time ("GMT"). Alternately, the memory 254 may store time zone information of the patient's location and adjust the time stamp accordingly. The clock may account for periodic variances in time, such as the beginning or end of daylight savings time, and leap years. For example, if daylight savings time begins between void events, clock adjusts void event time accordingly. For example, if the voiding device 200 records a void event on Saturday Mar. 9, 2018 at 9 PM, then daylight savings time begins on Sunday Mar. 10, 2018 at 2 AM, and the voiding device 200 detects another void event on Sunday Mar. 10, 2018 at 6 AM, the clock adjusts the time between void events to be eight hours rather than nine hours as the time stamps would indicate absent information about daylight savings time. In other examples, the clock may record a time interval between detected first flow or activation and the end of flow or deactivation e.g., 20 seconds.

The method may proceed to operation 406 and the device processing element 252 or server processing element 152 monitors the fluid level in flow chamber 204 via fluid level sensor 262 over time by periodically receiving output from the fluid level sensor 262 over a series of sampling intervals. The device respective processing element also monitors the orientation of the voiding device 200 over time the by periodically receiving output from the validation sensor 260, such as plurality of orientation values. In one example, the device processing element 252 executes instructions to receive electronic signals with a sampling rate of 1 sample per second, or 1-Hz. In this example, the device processing element 252 reads analog electrical signals from the fluid level sensor 262 and/or the validation sensor 260, and converts those analog signals to digital signals through a digital-to-analog converter (DAC) circuit, thereby generating a plurality of fluid level sensor values and/or a plurality of validation sensor or orientation values. The DAC circuit has a certain digital resolution that it uses to divide the analog signal into discrete digital values of precision. For example, the DAC may have a digital resolution of 12-bits, where the DAC divides the analog signal into $2^{12}$ or 4,096 discrete pieces of digital information. The DAC may have lower or higher resolutions such as 8-bit, 10-bit, 16-bit, 32-bit, or other values, for example. Additionally, the DAC may have lower or higher sampling frequencies defining the number of sampling intervals per over a given time period. For example, the DAC may have sampling frequencies such as 0.1-Hz, 10-Hz, 100-Hz, defining one sampling interval every ten seconds, ten sampling intervals per second, or 100 sampling intervals per second, respectively. The sampling frequency may be varied based on desired sensitivity, expected flow rates, or the like. The device processing element 252 reads these pieces of digital information to monitor the position of the displacement sensor 222, and may further process or refine the digital information, storing and retrieving some or all of it in the memory 254. In another example, the device processing element 252 simply records inputs as received directly or indirectly from the sensors in memory 254.

Continuing operation 406, the device processing element 252 or server processing element 152 monitors a number of parameters about the fluid level in flow chamber 204, to determine a number of different outputs. In one example, the device processing element 252 monitors the float 230 position. In one example, the device processing element 252 monitors the float 230 angular position $\phi$ over time and records that it initially increases, as fluid flow increases. In one example, as illustrated in FIG. 2E, the float 230 begins at a lower position indicated by $\phi_1$, with the float 230 resting on the inner surface of the bottom wall 218 of the flow chamber 204. As fluid flows into the flow chamber 204, the float 230 angular position $\phi$ may move to a higher value, for example, $\phi_2$, as illustrated in FIG. 2F. As illustrated for example, in FIG. 2G, the float 230 angular position may reach a peak value $\phi_3$ as fluid flow reaches a peak value. During a flow event, the angular position $\phi$ of the float 230 may move up or down, as variations in flow rate into or out of the flow chamber 204 occur. The float 230 angular position $\phi$ may decrease over time as fluid flow decreases, eventually returning substantially to its initial position $\phi_1$. These variations are captured by the device processing element 252 at the desired intervals over the flow event timeframe and are optionally stored in memory 254 or transferred to another device, for example to server processing element 152. In another example, the device processing element 252 monitors a capacitance value of a capacitance level sensor corresponding to the fluid level in the flow chamber 204.

Also in operation 406 the device processing element 252 or server processing element 152 monitors the orientation of the voiding device 200 by receiving signals from validation sensor 260. The validation sensor 260 monitors the pitch and/or roll of the voiding device 200 in 3D space. The orientation of the voiding device 200 in 3D space may affect the outflow rate from the outlet 204b. For example, if the voiding device 200 were pitched with the outlet 204b at a position substantially downward relative to the handle 202, the outflow rate of fluid may be increased relative to a position where the voiding device 200 was held in an orientation closer to horizontal. For example, the validation sensor 260 indicates a number of degrees from horizontal that the voiding device 200 is pitched. The validation sensor 260 may also indicate a direction of the pitch, such as downward or upward, where the direction is defined relative to the handle or other predetermined point on the device 200. In another example, the validation sensor 260 indicates a number of degrees of roll from horizontal, and a direction, e.g., 20 degrees left. In another example, the voiding device 200 is symmetric about an axis perpendicular to pivot axis 232 and the validation sensor 260 indicates a roll without a direction. In another example, the validation sensor 260 indicates a number of degrees and a direction that the voiding device 200 is offset relative to each of three orthogonal axes, e.g., 10 degrees from the z-axis, −20 degrees from the y-axis, and 5 degrees from the x-axis.

The method may proceed to operation 408 and the device processing element 252 or server processing element 152 receives information that the fluid level in flow chamber 204 is at a limit position. For example, the fluid level sensor 262 may indicate that the flow chamber 204 is empty. In one example, the device processing element 252 receives information that the float 230 is at a limit position indicating that corresponding fluid level is at a limit position. For example, as illustrated in FIG. 2E, the float 230 may be at rest against the inner surface of the bottom wall 218 of voiding device 200, as measured by angular position $\phi_1$. In other examples as illustrated in FIG. 2F, the float 230 may be at other positions, such as angular position $\phi_2$, as illustrated in FIG. 2F. The movement of the fluid level from a lower limit position $\phi_1$, and then later returning to substantially the same lower limit position $\phi_1$ may be used by device processing element 252 to detect the beginning and end of a flow event. For example, as fluid flow into the flow chamber 204 decreases, the float 230 may move to lower positions as fluid continues to flow out of the outlet 204b. The float 230 may also move to higher positions over the course of a void, due to changes in flow rate, the position of the voiding device 200, shaking, or other vibrations. Over time, the position of the fluid level should trend downward as flow diminishes and ceases. Eventually, as fluid flow stops and the remaining fluid within the flow chamber 204 exits, the fluid level reaches the lower limit position indicating the end of a flow event. For example, the float 230 may reach the end of its travel path, such as a mechanical stop. One example of a mechanical stop is the float 230 contacting the inner surface of the bottom wall 218 of the flow chamber 204. Another example of a mechanical stop may be mechanical limits built into one or both of the axles 236a, 236b. In another example, a lower limit position of the float 230 may be an electrical or sensor limit. For example, displacement sensor 222 senses rotary position within certain limits, beyond which it will sense a maximum or minimum value of rotation, as appropriate. The lower limit may be detectable by the validation sensor 260, and/or separate limit sensors that output a signal when the float 230 hits the limit, e.g., the arms 234a, 234b rest against a mechanical stop including a proximity sensor. At the flow event time, an end time stamp may be recorded, marking the end of the interval. In another example, the capacitance value of a of a capacitance level sensor indicates a fluid level limit position in the flow chamber 204.

Once the fluid level reaches the lower limit position, the flow event is presumed to be over, i.e., there is no fluid remaining in the compartment. There may be a wait time after the fluid level reaches its lower limit to capture any secondary flows that may occur. Once the flow events are assumed to be over, the method may proceed to operation 410 and a processing element determines flow data corresponding to the flow event. In one example, the device processing element 252 of the voiding device 200 transmits un-analyzed fluid level and voiding device 200 position data to the server 112 via a cellular network. The server processing element 152 analyzes the fluid level in the flow chamber 204 over the flow interval time. In one example, the device processing element 252 or a server processing element 152 analyzes the angular position $\phi$ of the float 230 (e.g., $\phi_1$, $\phi_2$, $\phi_3$, illustrated, for example, in FIGS. 2E-2G and positions in-between) and the orientation (e.g., pitch and/or roll) of the voiding device 200 using validation sensor 260 over the flow event time interval. The server processing element 152 uses the time data, angular position data, and position data in 3D space to determine input flow rates and/or accumulated flow volumes. For example using predetermined characteristics of the voiding device 200 relative to float angular position $\phi$ and voiding device 200 orientation and the detected data, the flow rates can be determined. The predetermined characteristics may be stored either within memory 254 of the voiding device 200, or in memory on a server 112 or other device.

In one example, the device processing element 252 or the server processing element 152 uses fluid level data, such as fluid sensor positions, and/or orientation values to interpolate or translate input flow rates from predetermined characteristics in the form of a lookup table or other relational structure. In one example, the device processing element 252 or the server processing element 152 uses float angular position $\phi$ and voiding device 200 orientation (e.g., pitch and/or roll) to interpolate input flow rates from predetermined characteristics in the form of a lookup table. The voiding device 200 has an outlet 204b that may be shaped to have lower outlet flows at lower corresponding inlet flows, to increase the sensitivity of the flow measurements. The outlet 204b may also have higher outlet flows at corresponding higher inlet flows to prevent urine from overflowing the flow chamber 204. The voiding device flow chamber 204 and outlet 204b shapes may also be different between the male and female devices to increase sensitivity in target urine flow ranges. That is, the flow chamber and outlet may be configured to optimize collection precision, orientation, and/or comfort for the user depending on the user's anatomy and common void positions. This helps to ensure that the user can comfortably handle the voiding device during void events, while also ensuring that the fluid is properly captured and accurately measured during the voiding events.

The voiding device 200 may have an outlet 204b that has different outlet flow characteristics at different voiding device 200 orientations, e.g., at different pitch, roll, and/or fluid level sensor 262 positions, which allow determination of flow properties, (e.g., rate, volume, time, duration, peak, onset and/or end of flow) by detecting changes of these characteristics. Tables 1A, 1B, and 1C below illustrate exemplary relationships between these values.

TABLE 1A

| Predetermined Float Angular Position φ: 10° | | Predetermined Roll deg. 10 | Actual roll deg. 12 | Predetermined Roll deg. 20 |
|---|---|---|---|---|
| Predetermined Pitch deg. | 20 | 12 | | 17 |
| Actual Pitch deg. | 30 | 18.5 | 19.7 | 24.5 |
| Predetermined Pitch deg. | 40 | 25 | | 32 |
| | | Outlet flows mL/sec | | |

TABLE 1B

| Predetermined Float Angular Position φ: 20° | | Predetermined Roll deg. 10 | Actual roll deg. 12 | Predetermined Roll deg. 20 |
|---|---|---|---|---|
| Predetermined Pitch deg. | 20 | 17 | | 23 |
| Actual Pitch deg. | 30 | 26 | 27.6 | 34 |
| Predetermined Pitch deg. | 40 | 35 | | 45 |
| | | Outlet flows mL/sec | | |

TABLE 1C

| Predetermined Float Angular Position φ | Outlet flows mL/sec |
|---|---|
| Predetermined Float Angular Position φ | 10 | 19.7 |
| Actual Float Angular Position φ | 18 | 23.65 |
| Predetermined Float Angular Position φ | 20 | 27.6 |

With reference to Tables 1A, 1B, and 1C above, in one example, at a particular moment or snapshot in time (such as a particular sampling interval) during a flow event, the voiding device 200 has a pitch of 30 degrees from horizontal on an axis parallel to pivot axis 232, with the flow chamber 204 angled down relative to the handle 202, has a roll of 12 degrees from horizontal on an axis perpendicular to pivot axis 232, and the float 230 angular position $\phi$ is 18°. Continuing the example, the server 112 memory 154 contains the following predetermined output flow rate characteristics at a float 230 angular position of 10 degrees. See Table 1A. The memory contains an outlet flow rate of 12 mL/sec corresponding to a pitch of 20 degrees, and a roll of 10 degrees. The memory 154 contains predetermined output flow rate of 25 mL/sec at a pitch of 40 degrees, a roll of 10 degrees, a predetermined output flow rate of 17 mL/sec at a pitch of 20 degrees and a roll of 20 degrees, and a predetermined output flow rate of 32 mL/sec at a pitch of 40 degrees and a roll of 20 degrees. As illustrated, the memory contains the following predetermined output flow rate characteristics at a float 230 angular position of 20 degrees, an outlet flow rate of 17 mL/sec corresponding to a pitch of 20 degrees, and a roll of 10 degrees, and memory 154 contains predetermined output flow rate of 35 mL/sec at a pitch of 40 degrees, a roll of 10 degrees. Further, the memory 154 contains a predetermined output flow rate of 23 mL/sec at a pitch of 20 degrees and a roll of 20 degrees and contains a predetermined output flow rate of 45 mL/sec at a pitch of 40 degrees and a roll of 20 degrees.

The server processing element 152 or the device processing element 252 uses interpolation, for example bi-linear interpolation, to determine the outlet flow rate of 19.7 at the conditions in Table 1A, and 27.6 mL/sec at the conditions of Table 1B. The respective processing element then interpolates between the outlet flow values at predetermined float angular positions φ of 10 and 20 degrees from tables 1A and 1B, respectively, for an actual float position φ of 18 degrees. The respective processing element determines the outlet flow rate of 23.65 mL/sec. See Table 1C. The respective processing element may use other types of interpolation, e.g., linear, cubic, bi-cubic, one dimension nearest neighbor or two dimension nearest neighbor. In various examples, the server processing element 152 determines outlet flows using one of the pitch, roll or fluid level sensor 262 position inputs; or any two of the preceding inputs in any combination.

The server processing element 152, or the device processing element 252 then uses the float 230 angular position φ and the interpolated outlet flow rate to determine the inlet flow rate. For example, the inlet flow rate is determined as the output flow rate plus any change in retained volume in the flow chamber 204 since the last sampling interval. If the fluid level sensor 262 rises from one sampling interval to the next, then there is more fluid volume retained in the flow chamber 204 in the current sampling relative to the previous sample, and the input flow rate is correspondingly higher than the outlet flow rate. Likewise, if the fluid level sensor 262 falls in the current sampling interval relative to the previous sampling interval, then the outlet flow rate is higher than the inlet flow rate. This retained volume is determined from lookup tables, using similar methods and inputs (e.g., pitch, roll, and fluid level sensor 262 position) as with the outlet flow rates as illustrated e.g., in Tables 1A, 1B, and 1C.

In another example, the predetermined characteristics take the form of a mathematical relationship with float 230 angular position φ, pitch, and optionally roll, as inputs and input flow rate as an output. In one example, the server processing element 152 determines urine flow rate by analyzing the outflow rate with float 230 angular position φ data, and/or voiding device 200 orientation data. In particular, the server processing element 152 (or device processing element 252) uses the float 230 position over the detected time period in light of the known exit rate of the flow chamber 204 to determine the rate of flow into the flow chamber 204, e.g., from the user. The above is meant as illustrative only and the flow rate input into the voiding device 200 can be determined in other manners.

The method may proceed to operation 412 and the server processing element 152 or the device processing element 252 determines a total fluid flow volume for the event. For example, the server processing element 152 may numerically integrate a fluid input signal over time as determined from the fluid level data and voiding device 200 position data, such as determined in operation 410. In one example of a method of numerically integrating urine flow rate, the server processing element 152 uses a left end-point rectangular approximation to obtain an estimate of accumulated fluid flow over time. The respective processing element may use flow rate data, such as data determined in operation 410, to estimate an accumulated amount of fluid over a time step, and store the result in the memory 254. For example, if the device processing element 252, or the server processing element 152, samples fluid flow rate at 0.1 second sampling intervals, the accumulated volume in any particular sampling interval may be determined by multiplying the sampled value of flow rate by the time step (e.g., 0.1 s). Then for instance, if the device processing element 252, or the server processing element 152, samples fluid flow rate at 5.0 seconds since the onset of fluid flow, and the value of the fluid flow rate may be 7 milliliters per sec (mL/s). The respective processing element would multiply 7 mL/s by 0.1 seconds to arrive at an accumulated amount of fluid over the time step from 5.0 seconds to 5.1 seconds of 0.7 mL. The respective processing element would then add 0.7 mL to accumulated volumes of fluid from previous time steps, and store the result in the memory 254. In other examples, the respective processing element may use left end, right end, trapezoidal, midpoint, Simpson's, parabolic, or other approximations to determine an accumulated urine volume. Operation 412 may result in a vector of data points of accumulated fluid volume, and may also result in a corresponding vector of associated times. The device processing element 252 may store these vectors in the memory 254, or the server processing element 152 may store these vectors in the memory 154. Other types of calculations can be done as well that intake characteristics of the voiding device 200 and flow rate data to determine accumulated flow volume.

The method may proceed to operation 414 and the server processing element 152 or the device processing element 252 stores the flow event data in memory storage, either on the device itself in memory 254, on the server 112 in memory 154, or the like. In various examples, the flow event data are raw data or filtered data. In one example, the device processing element 252 transmits flow event data to the server 112 via the network 102, such as a cellular network and the server 112 stores the flow event data in memory on the server 112. Alternately, the device processing element 252 transmits flow event data to the healthcare provider device 109, the report device 110, the third party device 103, or any combination of the above. Alternately, the device processing element 252 of the voiding device 200 transmits the flow event data to the server 112 via network 102, which may be a private network such as a cellular network, a public network such as the internet, or a combination.

Figure 5:
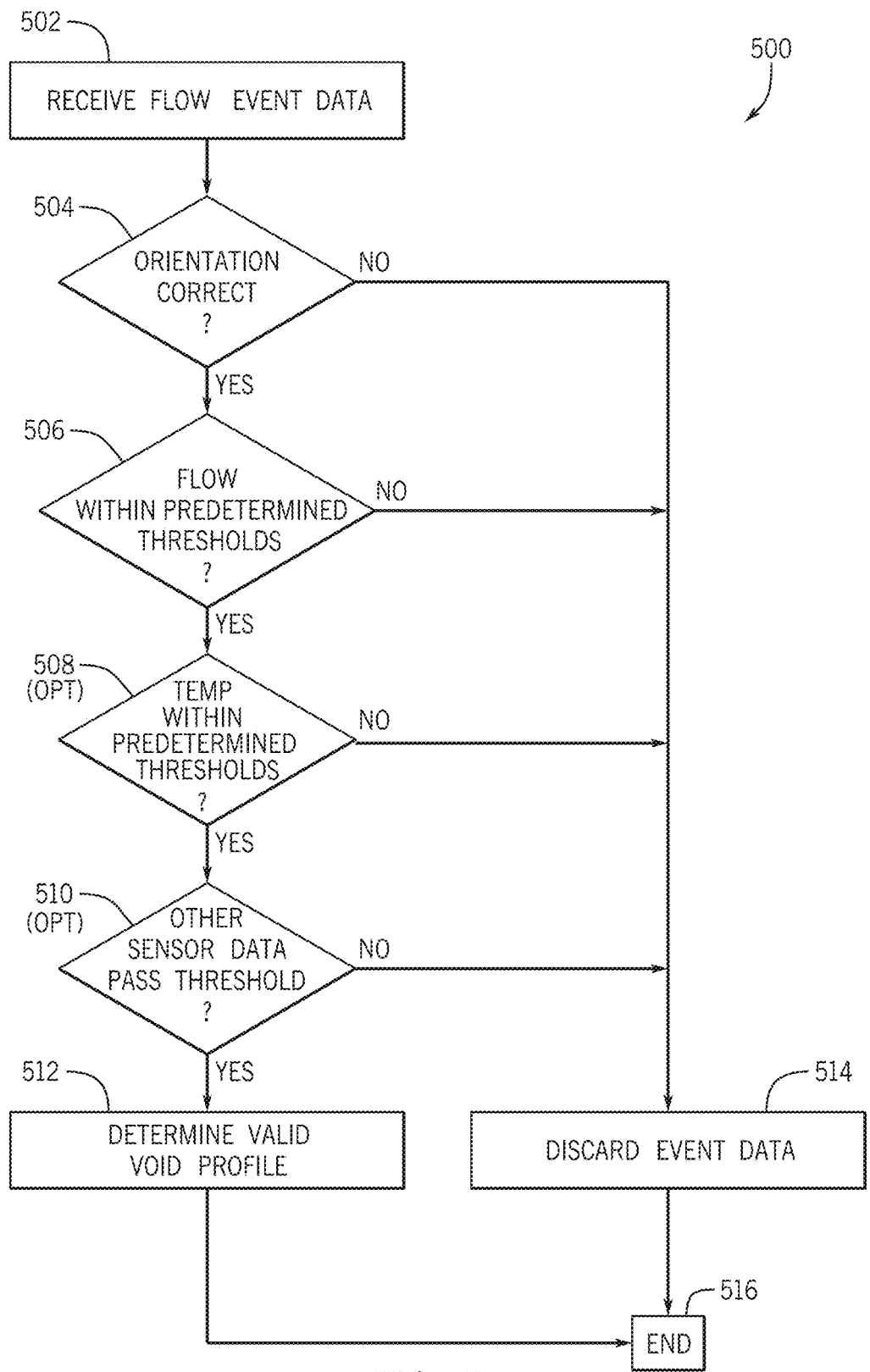
FIG. 5 is a flow chart illustrating a method for validating captured flow event data as corresponding to a void.

In many instances, the voiding device 200 may detect flow events that do not correspond to actual voids, but instead to the user rinsing or washing the voiding device 200. FIG. 5 is a flow chart illustrating a method 500 for validating flow event data as being associated with a void event. By validating data as being connected to an actual void event, rather than another event (e.g., user washing the voiding device 200, inadvertent sensor detection, etc.), the system can avoid analyzing and transferring irrelevant data, helping to increase accuracy, as well as efficiency of the device. For example, the device processing element 252 may analyze one or more validation characteristics detected by the various validation sensors 260 within the voiding devices 200. In particular, the server processing element 152 or the device processing element 252 may analyze validation characteristics such as acceleration of the voiding device during the flow event; the orientation of the voiding device during the flow event; the orientation of a user hand on the voiding device during the flow event; the temperature of the fluid flowing through the voiding device during the flow event; or the total volume of the fluid flowing through the voiding device during the flow event. In particular the device processing element 252 can validate detected flow event data to determine whether flow event data are associated with a void event, or some other type of event, such as for instance washing the voiding device 200, or accidentally dropping it in a toilet.

The device processing element 252 may execute method 500 to determine that flow event data are potentially valid void data. The server processing element 152, with its greater processing power, may receive validated void data and execute method 500 again on the data with different thresholds, or analyses to double check, or more accurately determine, the validity of the data. Alternately, operations or parts of operations of method 500 may be performed on the device processing element 252 and others performed on the server processing element 152, or other processing elements associated with the healthcare provider device 109, third party device 103, user mobile device 108, or report device 110. The method 500 may be executed while a flow event is occurring or after the voiding device 200 has detected that a flow event has occurred and transmits the data to an on-board processor for analysis and/or filtering or to a server 112 or other device via the network 102.

The method may begin in operation 502 and the server processing element 152 or device processing element 252 receives flow event data, such as the data detected in method 400 and/or from a storage location, (e.g., memory 154 on the server, the healthcare provider device 109, the report device 110, the user mobile device 108, or the third party device 103) from a memory 254 location on the voiding device 200 or via the network 102. In another example, the server processing element 152 receives un-analyzed flow event data from the voiding device 200 via the network 102. In another example, the processing element corresponds to the healthcare provider device 109 and receives flow event data either directly from the voiding device 200 or indirectly via network 102. In another example, the processing element is within a report device 110 and receives flow event data directly from a voiding device 200 or indirectly via network 102. In yet another example, the processing element is within a third party device 103 and receives flow event data from the voiding device 200 directly or indirectly via network 102.

After receiving flow event data, the server processing element 152 or device processing element 252 may then analyze the data with respect to various sensors, validation characteristics, and characteristic thresholds to determine if the data is valid. The method may proceed to operation 504 and the respective processing element determines whether the float 230 orientation and/or the orientation of the voiding device 200 itself are correct for a detected flow event. The orientation may be detected based on a position of the displacement sensor 222, as well as a 3D position/orientation of the voiding device 200. For example, if the float 230 was at an abnormal position, such as at its full upper limit, when flow through outlet 204b was detected, the respective processing element may determine a rinsing event has occurred. As another example, if the validation sensor 260 detects high acceleration values over the event time, the respective processing element may determine that a user was tapping the voiding device 200, such as during a rinse event. For example, the respective processing element may determine that the float 230 reached an upper limit position during a flow event, thereby clipping flow event data. This condition could be indicative of a high volume flow, as from a faucet, while a user rinses the voiding device 200.

In another example, the float 230 may be detected at an intermediate position after the flow event was over, indicating that the flow chamber 204 contains some fluid, or possibly that the float 230 was stuck. In one example, the respective processing element receives the float 230 position over time to determine if the float 230 was steady, e.g., stable, or not shaking or moving erratically. For example, if the float 230 was at a lower limit position or some other initial starting position, and was steadily at or near that position for a pre-determined period of time, the respective processing element may determine that the voiding device 200 was stable enough to take accurate measurements. In another example, if the initial position of the float 230 varies erratically over time, the respective processing element may determine that the voiding device 200 was not stable enough to take accurate readings. In one example, the respective processing element monitors the float 230 position to determine whether the float 230 position contains signal noise, or other variations not associated with a void event. In one example, the device processing element 252 (or the server processing element 152, or another device) detects the orientation of the voiding device 200 via input from the validation sensor 260 and/or the fluid level sensor 262 and compares the voiding device 200 position to a urinary event position to determine that the detected orientation is valid. The urinary event position may be predetermined and may be stored in memory 254 on the voiding device 200, or in the memory of another device.

Figure 12:
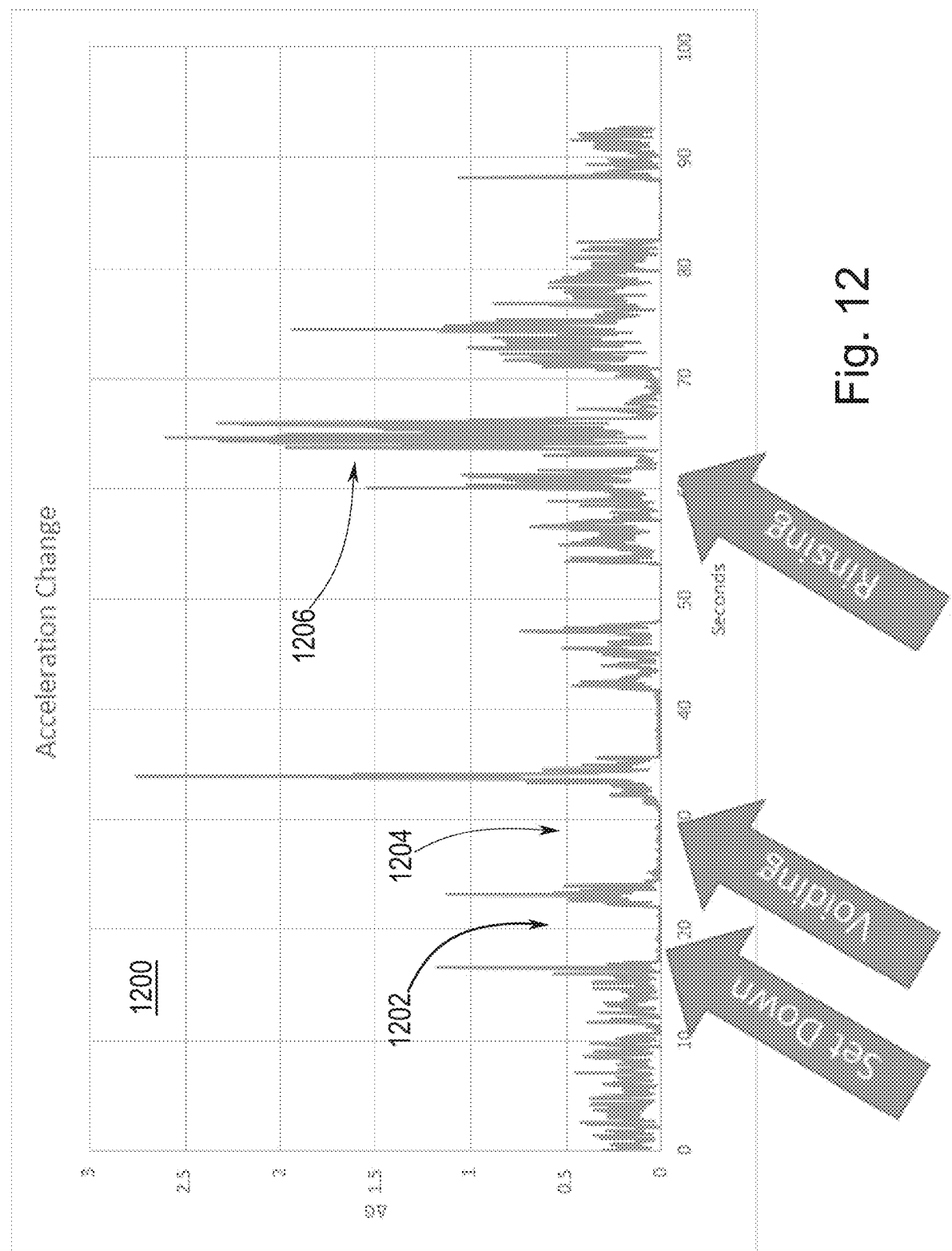
FIG. 12 illustrates variations of acceleration detected by the voiding device during use.

The urinary event position may be different for various patients depending on various factors. For example the urinary event position may depend on the patient's gender (e.g., the urinary event position corresponds to a sitting position for a female patient, or a standing or sitting position for a male patient). In another example, the urinary event position corresponds to different patient positions if the patient is not ambulatory, uses a wheel chair or other assistive device. FIG. 12 illustrates output from a validation sensor 260, showing changes in acceleration of the voiding device 200, along with different events, such as setting the voiding device 200 down, voiding, and rinsing. Large changes in acceleration may be indicative of unsteady conditions where the voiding device 200 will be unable to take accurate readings. The various sensors and/or thresholds may be analyzed simultaneously, independently, or serially depending on the desired processing speed, robustness of the voiding device 200. As such, the discussion of the below operations should be understood to be executed in any order or timing, and various operations may be omitted or skipped as desired.

Additionally the server processing element 152 or device processing element 252 may analyze an orientation output to determine whether the voiding device 200 was in a proper position to collect urinary event data. For example, if the validation sensor 260 indicates the voiding device 200 was in a position other than substantially right side up (e.g., upside down with flow chamber 204 opening oriented toward the ground, sideways, tilted too far vertically up or down on an axis parallel to the pivot axis 232, and/or tilted too far to the left or right with respect to an axis perpendicular to the pivot axis 232), the respective processing element determines that the voiding device 200 was not in a proper position to collect urinary event data. If however, the validation sensor 260 values over time indicate the voiding device 200 was in a proper position to receive urinary event data, method 500 may proceed to operation 506. An example of output from the validation sensor 260 is illustrated in FIG. 12. FIG. 12 shows acceleration change data 1200, such as the number of degrees the voiding device 200 was from upright, for different activities, such as setting down 1202, voiding 1204, and rinsing 1206. FIG. 14 illustrates a superposition of acceleration change, as in FIG. 12, positioning error as in FIG. 13, and different events, showing for example how voiding and rinsing can be differentiated from one another.

Figure 13:
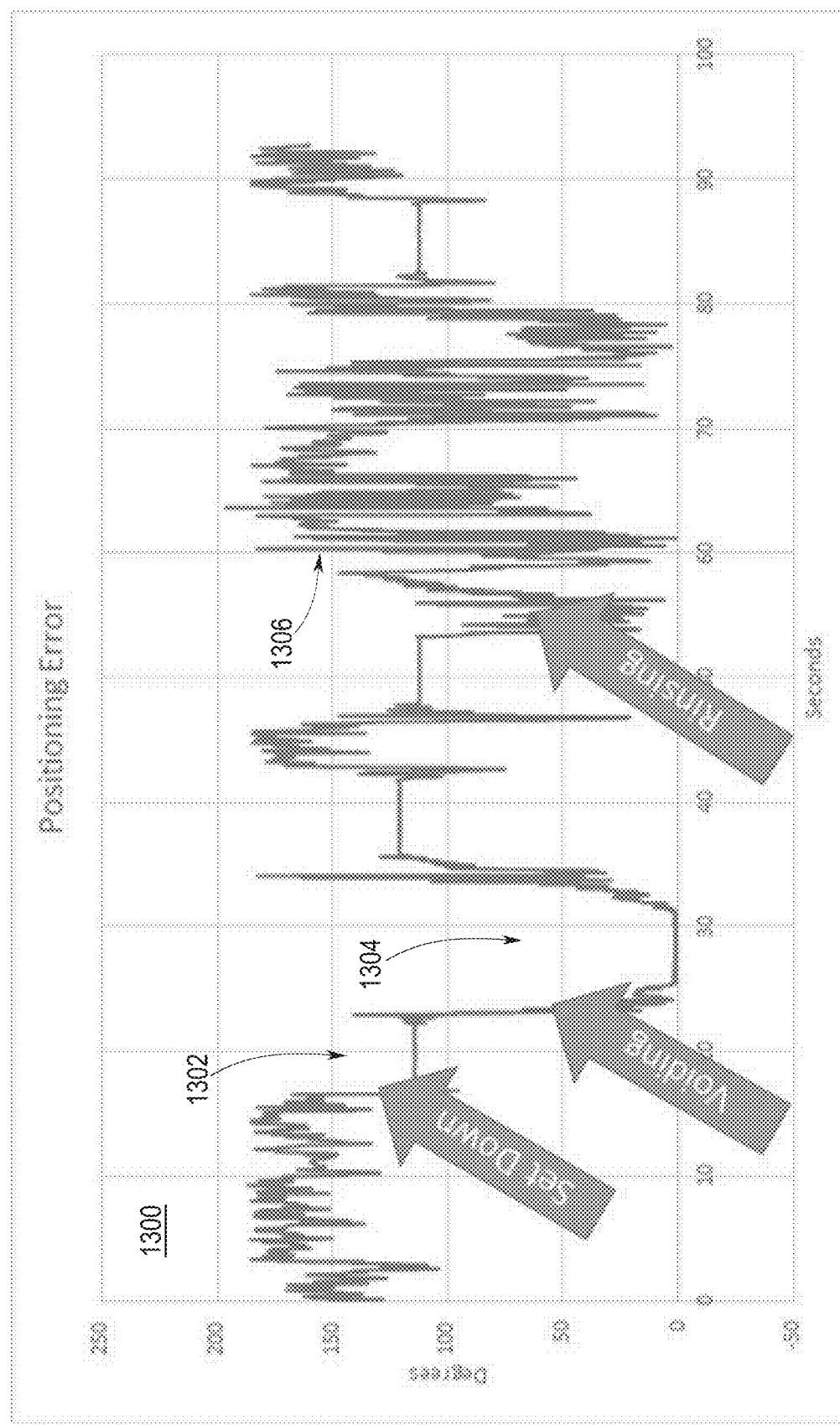
FIG. 13 illustrates positioning error detected by the voiding device during use.
Figure 14:
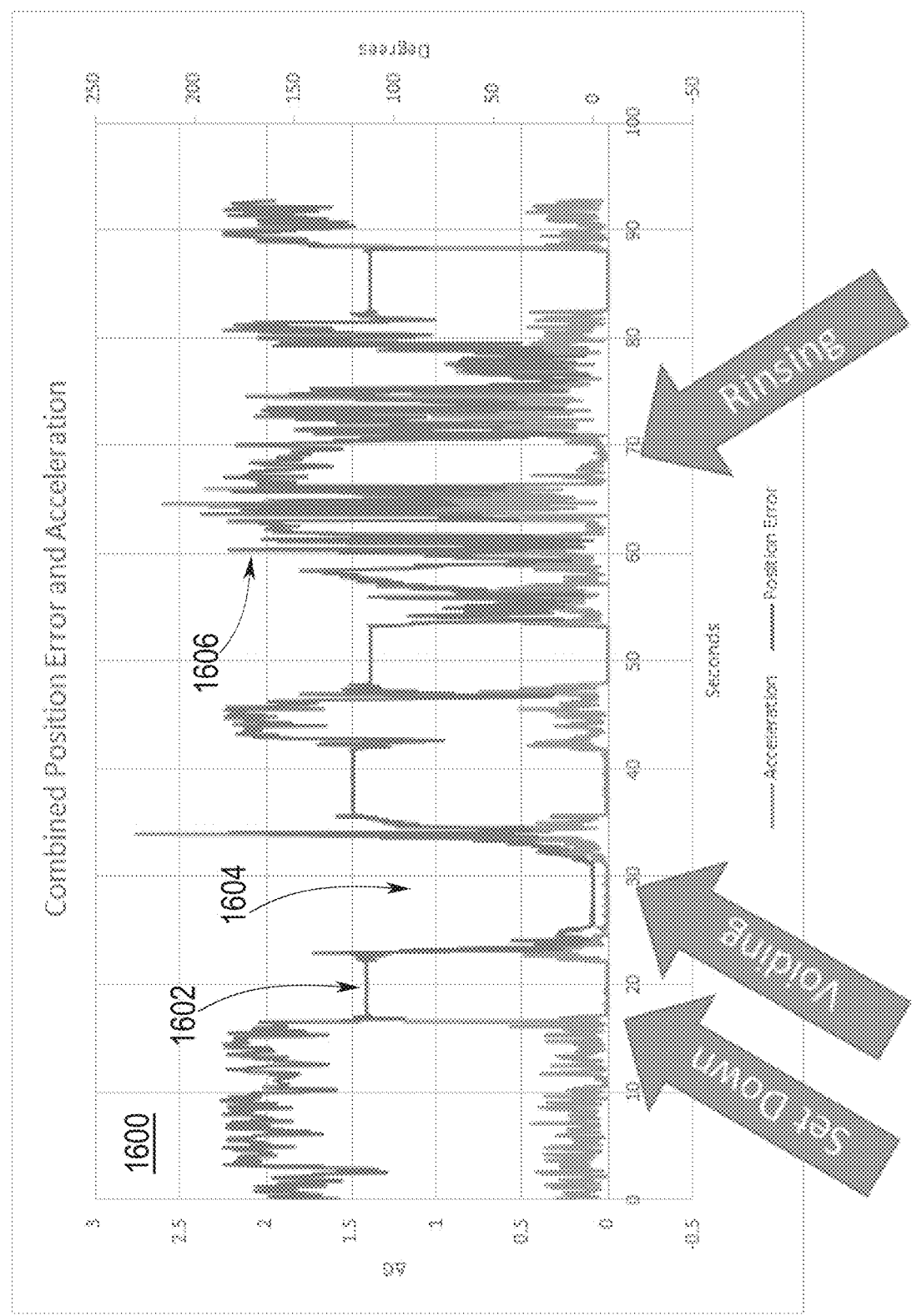
FIG. 14 illustrates using a relationship between acceleration changes and positioning error of a voiding device during use to validate detected voids.

FIGS. 12-14 illustrate various threshold values for different events. For example, FIG. 12 indicates low changes in acceleration when the voiding device 200 was set down, region 1202 or during a void, region 1204, and high values of acceleration change when rinsing 1206. FIG. 13 shows positioning error data 1300. Like FIG. 12, FIG. 13 shows unchanging positioning error data 1300 at about 120 degrees when the voiding device 200 was set down 1302, and a positioning error of about 0 degrees while voiding 1304, and erratic swings in positioning error while rinsing 1306. FIG. 14 shows the combination 1600 of positioning error data 1300 and acceleration change data 1200, as used to differentiate between setting the voiding device 200 down 1602, void events 1604 and rinsing 1606. For example, the respective processing element may determine that a void is happening when both the motion of the device is below a threshold, as in region 1204 FIG. 12, and when the positioning error is within some threshold as in region 1304, FIG. 13. The device processing element 252 and the server processing element 152 may use different thresholds or criteria for determining the validity of a void event. The respective processing element may use acceleration change data 1200, positioning error data 1300, alone or in any combination to discriminate between different types of events. However, by combining acceleration change data 1200 and positioning error data 1300 into combined data 1600, the respective processing element may be able to more accurately discriminate between different types of events than with a single data set.

In operation 506, the server processing element 152 or device processing element 252 determines whether fluid flow data associated with a flow event are within certain boundaries for urine flow by comparing the flow data to a variety of thresholds. The thresholds may either be predetermined; may be learned by the respective processing element from past history of a given patient; learned from typical data of patients with similar age, gender, ethnicity, height weight, and medical condition or history; or may be a combination of such thresholds. For example, the respective processing element may compare the detected fluid flow rate to a characteristic urinary event flow rate. The characteristic urinary event flow rate may be determined based on values typical for patients of similar demographics (e.g., gender, age, or ethnicity) as the current patient, or may be learned for a particular patient over time. For example, fluid flow rates may be too high or too low relative to characteristic, typical, or even possible urine flow thresholds for human beings. In another example, total accumulated fluid flow volumes may be too high or too low relative to characteristic, typical or even possible urine volume thresholds for human beings. For example, a total accumulated fluid volume of 3 gallons of urine was too high for any single void event for any human. In another example, peak flow rates may be too high or too low relative to typical or even possible values for human beings. For example, a peak fluid flow rate of 100 gallons of urine per minute was too high of a peak flow rate for any human. In another example, the duration of a flow event may be too long, e.g., 5 minutes. In other examples, any of these preceding thresholds may be compared to typical values for populations of which the patient was a member. For example, if the patient was a 65 year old male of Asian descent with a history of hypertension and smoking, the respective processing element compares flow values to typical urine flow values for persons of similar characteristics.

In operation 508 the server processing element 152 or device processing element 252 determines whether the detected fluid temperature in the flow chamber 204 associated with a flow event was too high or too low relative to threshold temperature values for urine. Operation 508 may be optional. For example, the respective processing element may compare the detected temperature to a characteristic urinary temperature or a temperature corresponding to a void, such as a gradual increase over time that stabilizes to body temperature. The detected fluid temperature may be determined by a sensor in contact with the fluid in the flow chamber 204, or it may be inferred from a temperature sensor elsewhere in the voiding device 200 not in contact with the fluid directly, e.g., a temperature sensor within the handle 202. For example, if either processing element determines, from a temperature sensor, that the fluid in the flow chamber 204 was above 50° C., the respective processing element will determine that this temperature was too high for human fluid output and the fluid was not urine from a patient, but due to rinsing the voiding device 200. In another example, either processing element compares fluid temperature in flow chamber 204 to typical body temperatures of about 37° C., and for deviations far above or below that typical temperature will determine that the fluid was not urine. The temperature value may be between a small window, validating the temperature only if not too cold and not too warm. The range may be within 10-15 degrees C., as human urine typically falls within expected temperature ranges. In another example, fluid temperature data are recorded from a from a temperature sensor in proximity to the urine stream, but not in fluid contact with the urine stream. For example, the magnetic float sensor 262 may have temperature sensor within it. Such temperature data may trend toward body temperature (from ambient) over the course of a flow event. A processing element may use that data as a signal that the event is truly a urinary or void event.

In operation 510 the server processing element 152 or device processing element 252 determines whether fluid flow data associated with a flow event are within certain boundaries for urine, by comparing flow data to other thresholds. Operation 510 may be optional. In one example, the respective processing element compares the electrical conductivity of fluid in the flow chamber 204 to threshold values for urine. For example, if the fluid has a low electrical conductivity, it may be distilled or de-ionized water. In another example, if the fluid has a very high electrical conductivity, it may be salt water. In another example, the respective processing element compares the opacity of fluid within the flow chamber 204 to threshold values for urine.

If the server processing element 152 or device processing element 252 determines in one or more of operations 504, 506, 508, or 510 that the flow data associated with a flow event are not void data, the method may proceed to operation 514 where the respective processing element discards the flow event data.

If however, the server processing element 152 or device processing element 252 determines in one or more of operations 504, 506, 508, or 510 that the flow data are void data, (i.e., corresponding to a human void event) the method may proceed to operation 512 where the respective processing element determines that flow event data are valid void data and determines a valid void profile 600. The method may end in operation 616

Figure 6A:
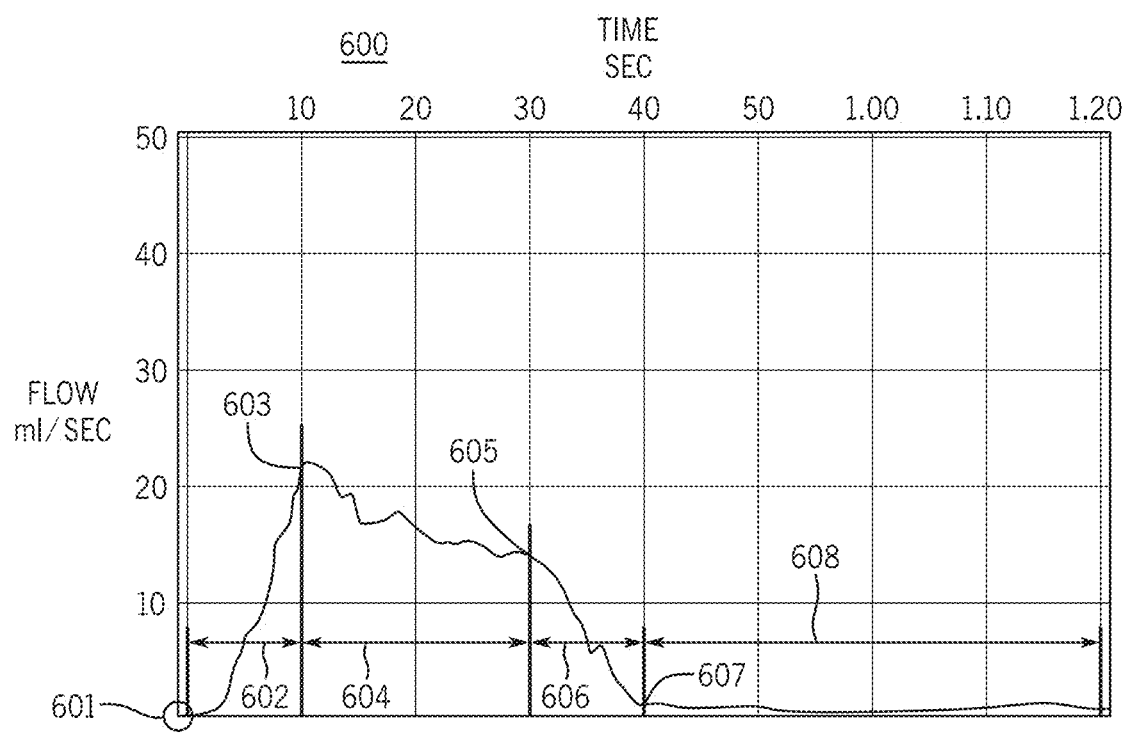
FIG. 6A is an example of a void flow rate profile validated using the method of FIG. 5.
Figure 6B:
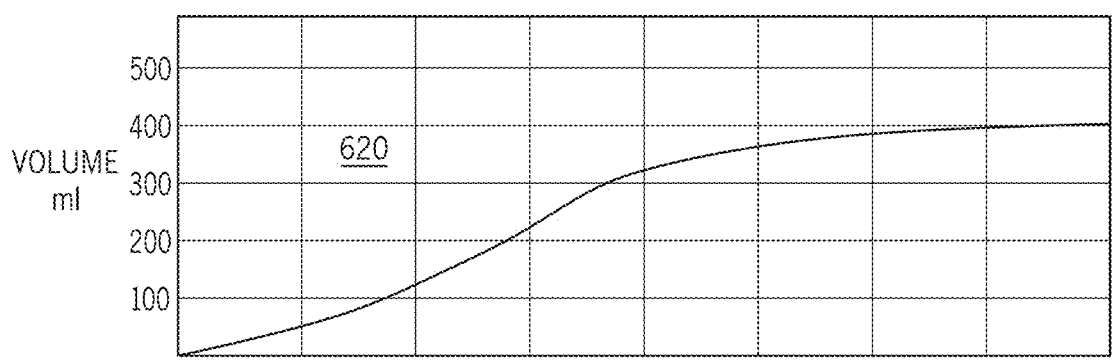
FIG. 6B is an example of an accumulated void volume profile validated using the method of FIG. 5.

Once flow event data has been validated, the processing element (either in the voiding device 200, server 112, user mobile device 108, healthcare provider device 109, report device 110, or third party device 103) generates a void profile. For example, the method 400 of FIG. 4 may be applied to generate the void profile and determine the associated characteristics. FIGS. 6A-6B illustrate an example of a void profile 600. The respective processing element may use the inlet flow of urine over time, and total urine volume accumulated over time, to develop a void profile. An example of a void profile may be seen in FIGS. 6A and 6B. FIG. 6A illustrates an example of urine flow over time. FIG. 6B illustrates an example of accumulated urine flow over time. As illustrated in FIG. 6A, the void profile 600 may have points and regions that may be detected by the respective processing element. For example a point may be a single point in time. A region may span between two or more points. The void profile is generated by the respective processing element by plotting the determined flow rate over the flow event time frame. Additionally, determined volume vs. time relationships may be plotted. The time stamps detected in method 400 along with the determined value can be used.

For example, the server processing element 152 or device processing element 252 may detect an onset of urination 601, for instance by detecting a change in a signal from a sensor. In one example, the device processing element 252 detects in increase of an output of the fluid level sensor 262, such as the float 230 displacement by way of the Hall effect sensor 222. In another example, the device processing element 252 detects a change in a conductivity sensor, for instance detecting an increase in conductivity between a pair of electrodes, consistent with the presence of an electrically conductive fluid such as urine. In another example, the device processing element 252 detects a change in an opacity sensor, for instance detecting an increase in opacity or decrease in transmitted light between an optical transmitter and an optical receiver, consistent with the presence of a liquid. In another example, the device processing element 252 detects a change in the location of an incident light beam on an optical detector caused by a difference between the index of refraction between air and water, urine or some other liquid. For example, an optical transmitter may be a light source, such as a light emitting diode, and an optical receiver may be a light sensor such as a phototransistor or cadmium-sulfide photodetector or other photo detector.

Generally, void profile 600 may further have a region of increasing urine flow. For example, the void profile 600 may have a region 602 where urine flow rate increases from the point of onset 601 to a maximum value at point 603. At point 603, urine flow may decrease, but is variable depending on the particular patient.

The void profile 600 may further have a region of slowly decreasing urine flow. For example, void profile 600 may have a region 604 where urine flow rate decreases slightly over time from the maximum point 603 or where urine flow rate remains substantially uniform over time. Urine flow rate may continue in region 604 to point 605, the beginning of the terminal region of urination. At point 605, the time rate of change of the flow rate of urine may begin to decrease in region 606, relative to region 604. In region 606, the flow rate of urine may decrease to a point 607 where urine flow rate substantially ceases. Following the point of cessation of urination, e.g., at point 607, the void profile 600 may include an additional region 608. Region 608 may represent a delay while the voiding device 200 waits to determine if urination may begin again. Some urinary health problems involve halting urination, where urine flow starts and stops multiple times with in a single void event. Region 608 in void profile 600 will help the voiding device 200 capture urination data consistent with such problems. As described with respect to operation 412 of method 400, the server processing element 152 or the device processing element 252 may numerically integrate the flow rate of urine over time to develop an accumulated urine profile, for example profile 620.

Figure 7:
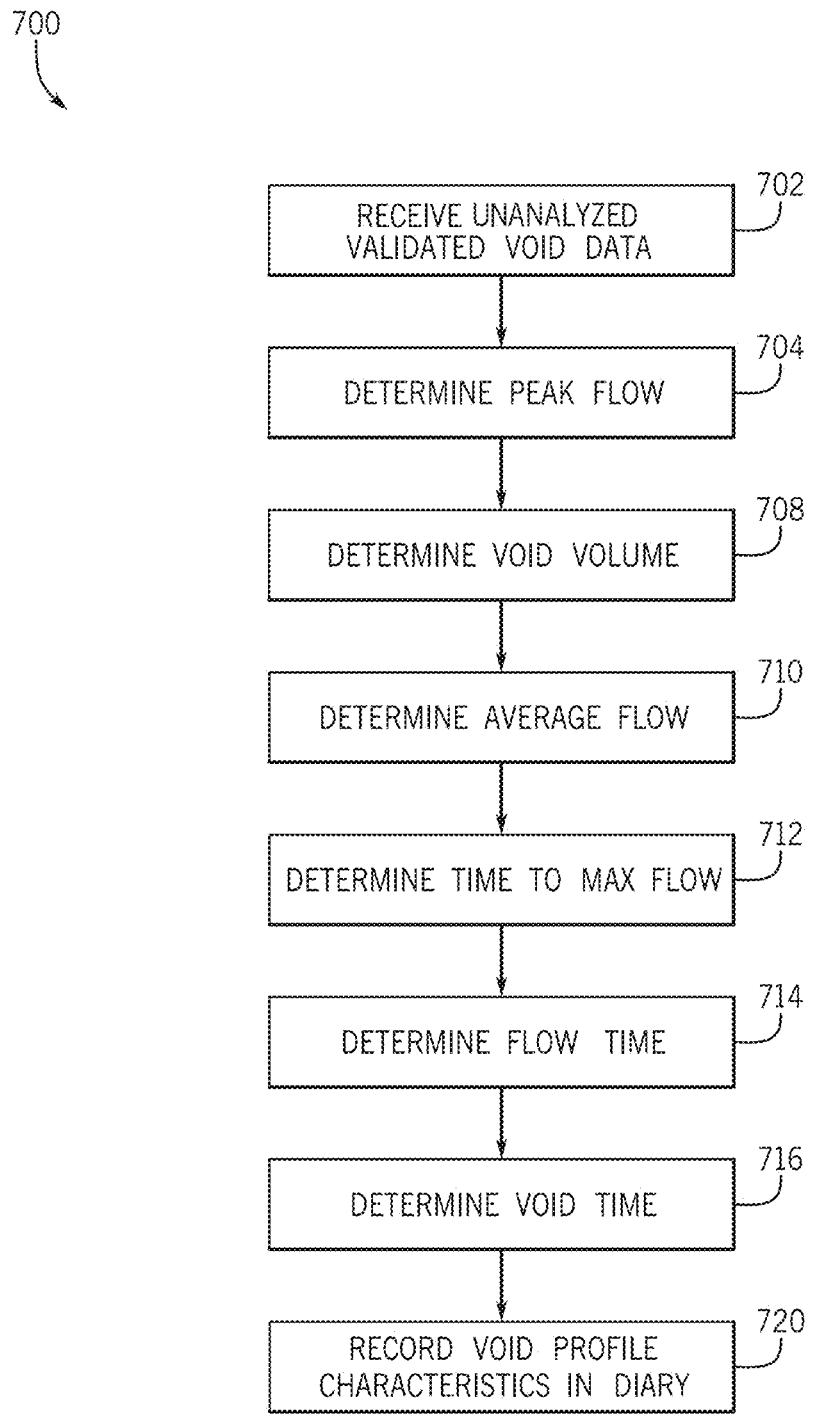
FIG. 7 is a flow chart illustrating a method for determining void characteristics of a detected void.

FIG. 7 is a flowchart illustrating a method 700 that determines parameters associated with a void profile 600. The method may be executed after a flow event has been validated as a valid void event by the processing element, on either the server 112, the voiding device 200, the user mobile device 108, or the like. In one example, the device processing element 252 sends valid or filtered void data, such as validated by method 500, to the server 112 via the network 102. The server processing element 152 then executes method 700 to determine parameters associated with a void profile 600. Alternately, in another example, the device processing element 252 of the voiding device 200 executes portions of method 700, and the server processing element 152 executes others. Various operations of method 700 may be executed by processing elements on any combination of devices, any order, including the voiding device 200, the healthcare provider device 109, the server 112, the report device 110, the user mobile device 108, and/or the third party device 103.

The method may begin with operation 702 when the server processing element 152 or device processing element 252 receives validated void data. The validated void data correspond to data collected by the voiding device 200 (e.g., fluid level data, pitch and/or roll) that has been validated via method 500 and corresponding to a void event, rather than another type of flow event. The validated void data may be received from any of the voiding device 200, the sever 112, healthcare provider device 109, the third party device 103, the user mobile device 108, the report device 110, or even another device. Validated void data may be received by the server processing element 152 either directly from one or more of the other devices, or it may be received via network 102. In one example, validated void data are a vector of data points of urine flow rates, and a corresponding vector of associated times stored by the server processing element 152 in the memory 154. The server processing element 152 may repetitively retrieve and store whole sets of void data or individual data points at various addresses within the memory 154. In another example, void data also include a vector of data points of accumulated urine volume, also associated with the corresponding vector of associated times. A truncated example of void data for a particular void event are represented by Table 2. Table 2 is not an example of an entire void profile, and is included as a tool to illustrate the operations of method 700. Data points occupy a position within the data vector. A data vector has a beginning at position 1 and an end.

TABLE 2

| Position | Time (s) | Urine Flow Rate (mL/sec) | Accumulated Urine Volume (mL) |
|---|---|---|---|
| 1 | 1 | 0 | 0 |
| 2 | 2 | 1 | 2 |
| 3 | 3 | 1 | 5 |
| 4 | 4 | 2 | 13 |
| 5 | 5 | 1.5 | 20.5 |
| 6 | 6 | 1 | 26.5 |
| 7 | 7 | 0 | 26.5 |
| 8 | 8 | 0.002 | 26.516 |

It should be noted that although the operations of method 700 are shown in a particular order they can be executed in parallel, separately, and in any order as desired. In operation 704 the server processing element 152 or device processing element 252 determines peak urine flow rate. For example, a peak urine flow rate such as point 603 of FIG. 5. In one example, the respective processing element determines peak urine flow rate by stepping through data points of the validated void data vector from beginning to end, two at a time and comparing them to determine which is larger. If the larger value is first in the vector, the positions of the two data points are left undisturbed. If, however, the smaller value is first, the positions of the two data points are swapped. This process continues through the vector and is then repeated until the vector of data points is in descending order, with the largest value first. In another example, the positions of the times associated with the data points are swapped whenever the data points themselves are swapped. This example results in a vector of data points sorted in descending order, and time vector containing associated times sorted according to the corresponding data points.

In another example, the server processing element 152 steps through data points of a validated void data vector one at a time. The server processing element 152 copies the first data point to a buffer location in the memory 154. The value in the buffer location may be called a buffered flow rate value. The server processing element 152 may also store the time value associated with the buffered value in a second buffer location in the memory 154. The value in the second buffer location may be called a buffered time value. The server processing element 152 may then proceed to step through the second and subsequent values in the validated void data vector. The server processing element 152 compares the second value in the validated void data vector to the buffered flow rate value. If the second value in the validated void data vector is larger than buffered flow rate value, the server processing element 152 copies the second value to the buffer in the memory 154, overwriting the buffered flow rate value. The server processing element 152 may also store the time value associated with the new buffered flow rate value in the second buffer location. If, however the second value is equal to or smaller than the buffered value, the buffered flow rate value and/or buffered time value are left unchanged. The server processing element 152 repeats this process through the validated void data vector of flow rate data. The operation then concludes with the server processing element 152 taking the current buffered value and determining it to be the peak urine flow rate. In the example of Table 2, the server processing element 152 would determine the peak value of urine flow rate as 2 mL/sec, at point 4. Other magnitude comparisons can be done as well, using various methodologies, the server processing element 152 analyzes the data to determine the peak.

In operation 708 the server processing element 152 or device processing element 252 determines accumulated void volume. In one example, the validated void data contains a vector of accumulated urine flow volumes (e.g., such as determined in operation 412 of method 400 and validated by method 500), and the server processing element 152 performs the steps of operation 704 on the vector of accumulated urine volume, rather than on urine flow rate data as in operation 704. For example, the server processing element 152 sorts the accumulated urine volume data in descending order, and determines the first value in the sorted vector to be the accumulated urine volume. In another example, the server processing element 152 steps through the accumulated urine volume data using the buffered value approach as detailed in another example of operation 704, and determines that the buffered value at the end of the operation is the total accumulated volume of urine. In the example of Table 2, the server processing element 152 would determine the accumulated void volume as 26.516 mL, occurring at 8 sec.

In operation 710 the server processing element 152 or device processing element 252 determines average urine flow rate. In one example, the server processing element 152 removes or ignores data points of validated void data vector that are close or equal to zero. In the example of Table 2, the server processing element 152 would ignore data points 1, 7, and 8. The server processing element 152 then adds a sum of all the remaining data points of urine flow rate in a validated void data vector. The server processing element 152 then counts the number of remaining data points in the validated void data vector. The server processing element 152 then divides the sum of the urine flow rate data by the number of data points. For example, in Table 2, the server processing element 152 may determine the sum of the remaining data points of urine flow rate to be 1+1+2+1.5+1=6.5 mL/sec. The number of data points in the urine flow rate vector is five, (e.g., data points 2-6, inclusive). The server processing element 152 then determines the average flow rate to be 6.5 mL/sec/5=1.3 mL/sec.

In another example, of operation 710 the server processing element 152 does not ignore or discard data points of validated void data vector that are close or equal to zero, determining an overall average urine flow rate. In the example of Table 2, the sum of all urine flow rate values is 6.602 mL/sec. The number of points is eight. The average then is 6.602 mL/sec/8=0.825 mL/sec.

In operation 712 the server processing element 152 or device processing element 252 determines the time to maximum urine flow. In one example, the server processing element 152 determines the peak urine flow rate according to operation 704. While performing method 700, the server processing element 152 sorts time values associated with urine flow rate values while finding the peak urine flow rate. In this example, the server processing element 152 takes the first value of the sorted time vector and determines it to be the time to peak urine flow rate. In another example, the server processing element 152 retrieves the buffered time value of operation 704 and determines it to be the time to peak urine flow rate. In the example of Table 2, the server processing element 152 may determine the time to the peak urine flow rate as 4 sec, associated with peak urine flow rate of 2 mL/sec.

In operation 714 the server processing element 152 or device processing element 252 determines flow time or duration data of the flow event. In one example, the server processing element 152 determines a first non-zero point in the validated void data flow rate vector (e.g., this is point 2 in Table 2). The server processing element 152 then records the time value associated with the first non-zero flow rate at a first location in memory 154. The server processing element 152 then steps through the data points in the validated void data flow rate vector one at a time looking for a first zero-valued data point following the first non-zero data point. For example, the server processing element 152 compares the data points to determine if they have dropped back to zero, or close to zero. If the server processing element 152 determines that a data point is zero or close to zero, the server processing element 152 may determine that this data point is the first zero-valued data point. The server processing element 152 then writes the time value associated with the first zero-valued data point to a second location in the memory 154. Completing the operation, the server processing element 152 subtracts the time value in the second memory location from the time value in the first memory location to determine a flow time. In another example, the server processing element 152 may apply filtering or other algorithms to avoid false positive determinations of either the first non-zero flow rate data point, and/or the first zero-valued data point following the first non-zero flow rate data point. In the example of Table 2, the first non-zero flow rate data point is point 2, and the associated time is 2 seconds. The first zero-valued data point following the first non-zero flow rate data point is point 7 with an associated time of 7 sec. The difference between these associated times, and thus the flow time, is 7 sec−2 sec=5 sec.

In operation 716 the server processing element 152 or device processing element 252 determines void time. In one example, the server processing element 152 reads the last value of time from a validated void data time vector in the memory 254 and determines it to be the void time. In the example of Table 2, the void time would be 8 sec. In another example, the server processing element 152 reads the value of flow time from the memory 254, such as resulting from operation 714, and adds a predetermined or variable time to the flow time to determine void time. For example, if the flow time resulting from operation 714 is 7 sec, as in Table 2, the server processing element 152 may append a fixed time, e.g., one second to the flow time to determine the void time as 8 sec, or the server processing element 152 determines the last outflow value time stamp and determines that to be the end time.

Figure 11:
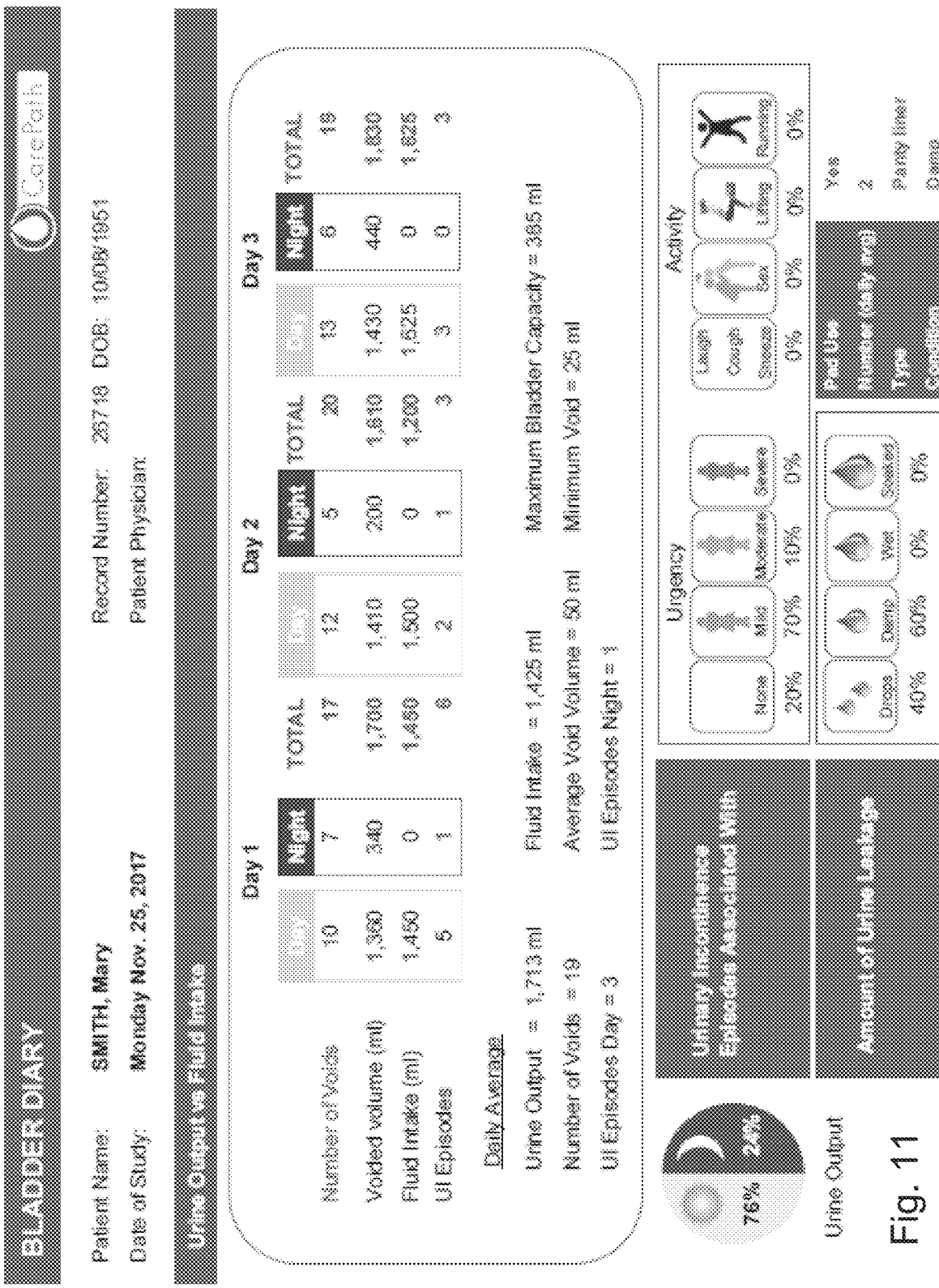
FIG. 11 illustrates an example of a report generated with the method of FIG. 8.
Figure 19:
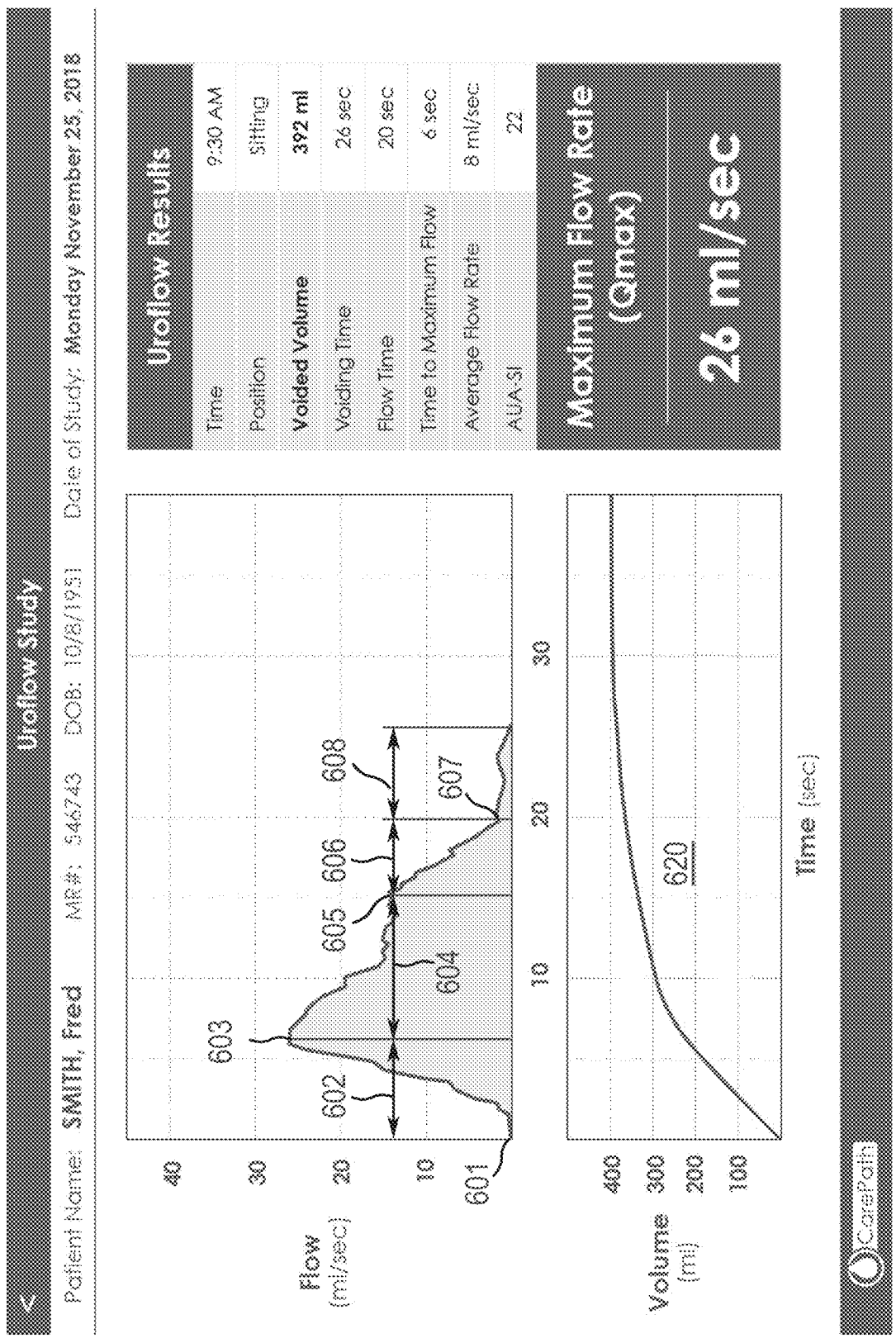
FIG. 19 is an example of a uroflow study report of void event of a patient
Figure 20:
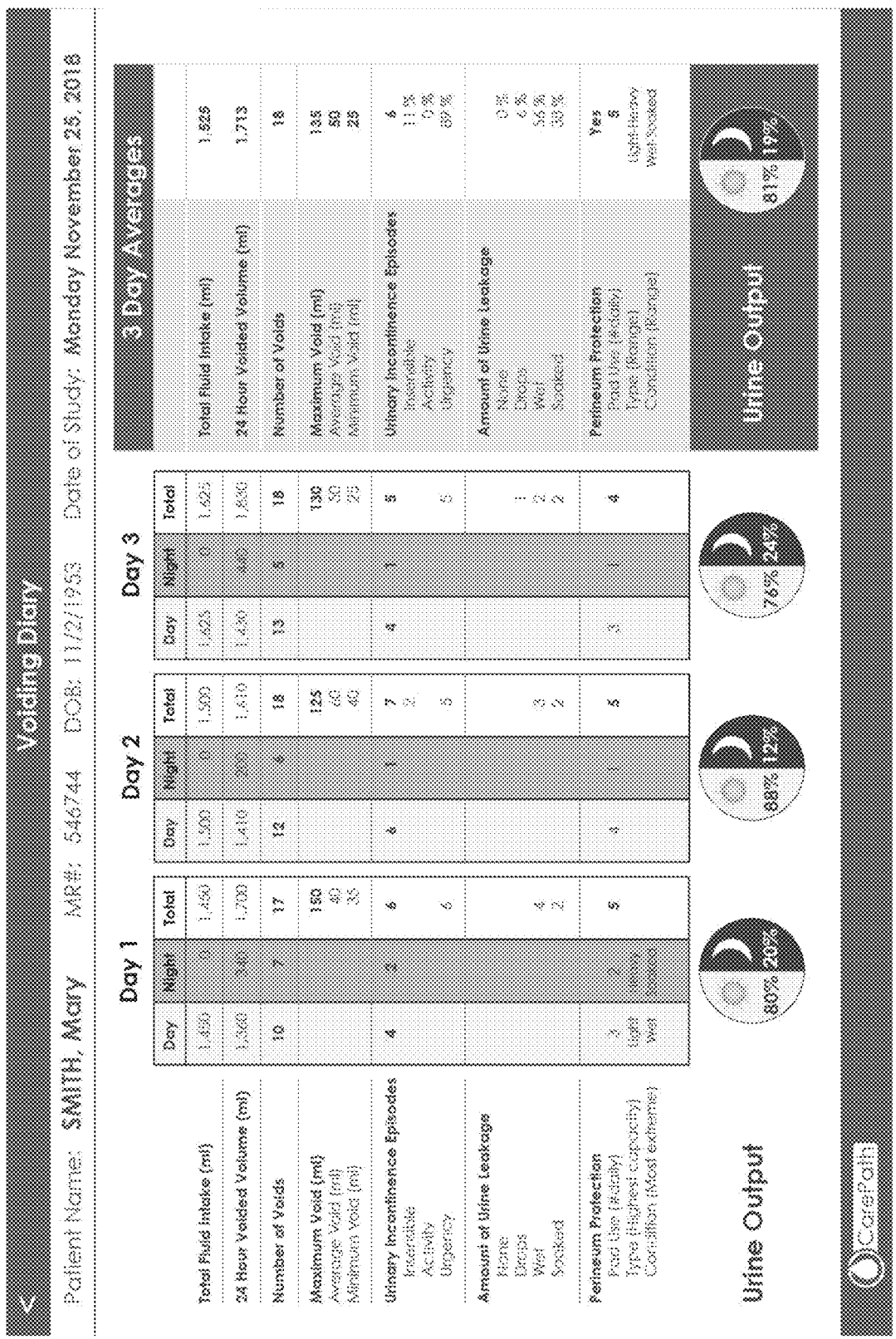
FIG. 20 is an example of a voiding diary report of a patient illustrating void data over a period of consecutive days.

The method may conclude with operation 720, and the server processing element 152 or device processing element 252 records void profile characteristics in a void diary. A void diary may contain information collected by the voiding device 200 as well as information collected and recorded manually by the patient, healthcare providers, insurance providers and/or third parties. The void diary may exist in memory storage on any of the voiding device 200, the user mobile device 108, the server 112, the healthcare provider device 109, the report device 110, the third party device 103, or another device. In one example, the void diary takes the form of a database, e.g., a relational database where void data as determined by method 700 are stored as fields in a variety of tables. As illustrated in FIG. 11, in another example, the void diary shows a summary of data collected about the patient's urinary health, including information collected by the voiding device 200 (e.g., the number of voids, including a classification by whether they happened during the day or night, total and average voided volume, maximum bladder capacity, the size of the smallest void, and a percentage of urine output during the day and night). Also as illustrated in FIG. 11, the void diary contains information collected by the patient. For example, the void diary contains information about the patient's: fluid intake; number of episodes of urinary incontinence ("UI"); sense of urgency to urinate; activities that preceded or were associated with UI (e.g., laughing, coughing, sneezing, sex, lifting, or running); amount of urine leakage; and absorbent pad use. In another example, the void diary provides the ability of a healthcare provider to input data to provide additional diagnostic and treatment response or performance information to be considered and used in analysis of the diagnosis or efficacy of the treatment. Data input into a voiding device may be transmitted back to the server 112, e.g., from a healthcare provider device 109, to the server 112 for recordation, analysis, and reporting. FIG. 20 shows another example of a voiding diary over the course of three consecutive days. In the example of a voiding diary illustrated in FIG. 20, the diary includes information such as: total fluid intake; volume voided over a 24 hour period; maximum, average, and minimum void volumes; incontinence episodes; leakage; and pad usage split up by day and night. Alternately, in operation 720, a respective processing element may create a uroflow study of a single void event, an example of which is illustrated in FIG. 19. The study may include information representative of the data in FIGS. 6A and 6B, and may include the time of the void, the patient position (e.g., sitting, standing), the voided volume, the voiding time, the flow time, the time to maximum flow, the average flow rate, and an overall score for the void event. In one example, the study shows an American Urological Association Symptom Index ("AUA-SI") score that measures the severity of a patient's overall urological symptoms.

Figure 8:
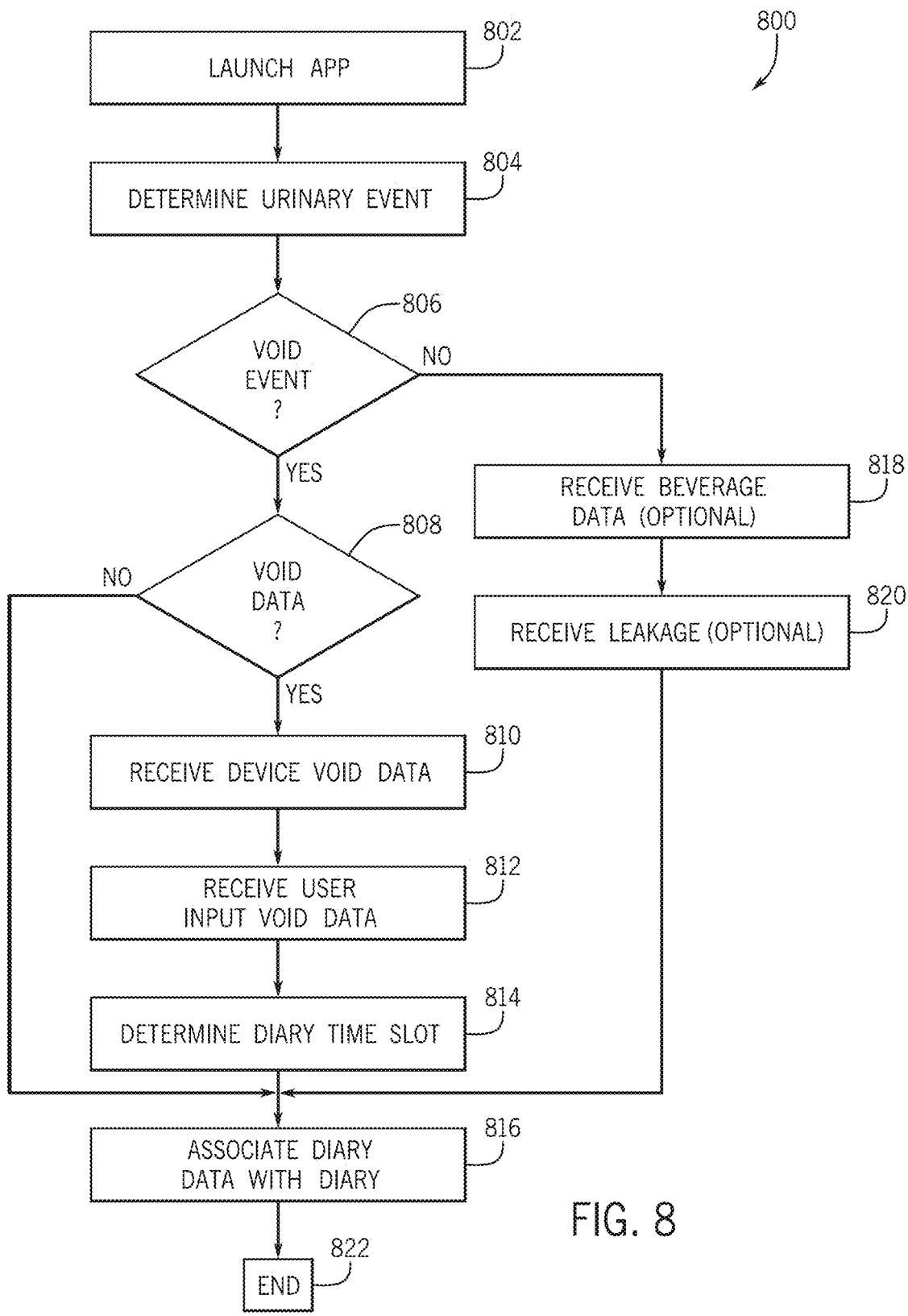
FIG. 8 is a flow chart illustrating a method for capturing void diary information corresponding to detected voids.

FIG. 8 discloses a method 800 where the processing element on the user mobile device 108 collects void diary data from the server 112 and/or from a patient. The method may begin in operation 802 when the patient launches an application on user mobile device 108. The application may be any form of structured computer-executable or interpreted code that can be executed by the processing element.

The method may proceed to operation 804 and the processing element, through the application, determines a type of urinary event that has occurred such as through an input from the user via an input/output interface of the user mobile device 108. A urinary event may be any type of event relevant to the production or elimination urine. In one example, the application asks the patient to choose from among two types of urinary events: a void or drinking a beverage. In another example, the application asks the patient to choose from among three types of urinary events: a void, drinking a beverage, or having a leak associated with an episode of UI.

The method may then proceed to operation 806 where the processing element determines if the user has indicated that the urinary event was a void. In one example, the user mobile device 108 presents a user interface to the user who then selects an event corresponding to a void event. A void is a urinary event in which the user intentionally eliminates urine from his or her bladder. On the other hand, a leak associated with UI is where urine is eliminated from the user's bladder in an unintentional, uncontrolled, or unconscious fashion. If the user has indicated that the event was a void, the method may proceed to operation 808. If the event was not a void, but rather was an episode of UI, or fluid intake, the method may proceed to operation 818 or 820 in any order.

In instances where the event is a void, the method may proceed to operation 808, and the processing element scans the server 112 for void data, or requests or retrieves void data from the server 112. In another example, the user mobile device 108 sends a data request to the server 112, which then transmits the requested data to the user mobile device 108. Alternately, the processing element requests or retrieves relevant void data from the voiding device 200. For example, the server 112, or the user mobile device 108 may connect either directly through wireless or wired technologies to the voiding device 200, and send a query to the voiding device 200 to determine if it contains void data. In some examples, the processing element of the user mobile device 108 communicates with the voiding device 200 via Bluetooth®, Wi-Fi®, near field communications. In other examples, the processing element communicates with the voiding device 200 on USB or other wired communications methods. In other examples still, the processing element communicates with the voiding device 200 via network 102 using any combination of wired and wireless technologies.

If the flow event data are available, the method may proceed to operation 810 and the processing element receives void profile characteristics or other void data. In one example, the processing element receives void profile characteristics from the server 112. In one example, the processing element receives void profile characteristics from the voiding device 200 itself. The processing element may identify the void profile characteristics to determine if it is the correct data from a recent void, as opposed to old data remaining in memory 254 of the voiding device 200. For example, the processing element may compare one or more time stamps of the void data to the current time, and determine whether the void data are recent. The processing element may use other methods to identify void data, such as a void data serial number, that may be unique. Processing element may receive void profile characteristics by any of the methods or technologies previously described with respect to the voiding device 200. Concurrently with, or after receiving void data, the processing element may store the void data in a memory storage 254. The method may then proceed to operation 812 or 814 in any order.

In operation 812 the application receives user input void data from the user, e.g., via the user mobile device 108, related to the void event. For example, the application may display a screen to ask about the reasons the patient chose to urinate and provide options or a textual input which the user can use to input information. In one example, the application asks if the patient urinated because of convenience or a feeling of urgency to urinate. If the patient indicates that the void was made because of urgency, the operation may proceed and the application may ask the patient about the severity of the urgency. In one example, the application asks the patient to rate the urgency as mild, moderate or severe. The operation may proceed and the application asks the patient about any leakage associated with the void event. In one example, the application asks the patient to rate the amount of UI leakage as: none, drips, wet or soaking. The operation may proceed and the application asks the patient whether he or she changed leakage protection as a result of the void. In one example, the application asks the patient if he or she made no change, changed a panty liner, light pad, heavy pad, or briefs.

The method may then proceed to operation 814 and the application determines the diary time slot for the void event. In one example, the application asks the patient if he or she is just waking up for the day and associates void data with awake time if the user answers in the affirmative. In another example, the application asks the user if he or she is going to bed for the night, and associates void data with bed time if the user answers in the affirmative. In another example, the application asks the user if he or she got up during the night due to a sense of urgency to urinate.

The method may then proceed to operation 816 where the processing element associates diary data with a user's void diary. The processing element may upload diary data to a void diary stored in memory on any of the voiding device 200, the user mobile device 108, the sever 112, the healthcare provider device 109, the third party device 103, or even another device. The processing element may perform this upload using any combination of the communications methods and technologies previously disclosed for connecting these devices. Further, the processing element associates the collected diary data from both the user and the voiding device 200 with a specific diary associated with that user. The processing element may display a void diary or void data on any of the voiding device 200, the user mobile device 108, the sever 112, the healthcare provider device 109, the third party device 103, or even another device.

If in operation 806, the event was determined not to be a void event, the method may proceed to operation 818, if in operation 806 the user indicated that the urinary event was not a void, but rather was an episode of UI, or fluid intake.

The method may proceed to operation 818 and the processing element via the application receives information regarding the user's fluid intake. In one example, the application presents the user with a series of graphical representations of beverages of various sizes (e.g., a cup (small), a can (medium), or a bottle (large)). The application may ask the user to input the volume of fluid he or she drank. In one example, the application asks the user to input the number of fluid ounces he or she drank.

The method may optionally proceed to operation 820, and the processing element via the application asks the user about UI leakage. In various examples, the application asks the user about his or her: number of episodes of UI; sense of urgency to urinate; activities that preceded or were associated with UI (e.g., laughing, coughing, sneezing, sex, lifting, or running); amount of urine leakage; and absorbent pad use or changes.

Figure 16A:
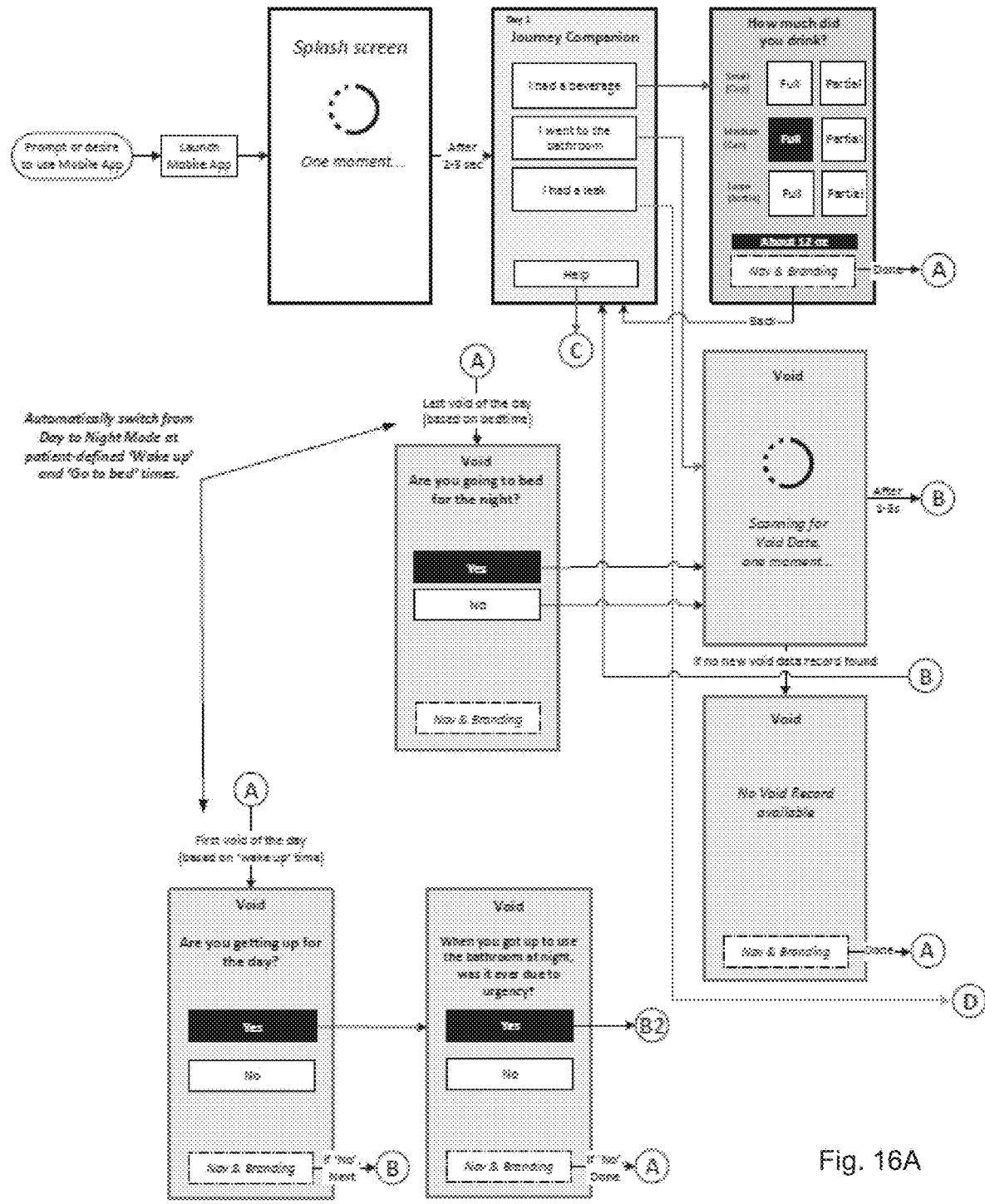
FIG. 16A is a flow diagram illustrating an implementation of portions of the method of FIG. 8.
Figure 16B:
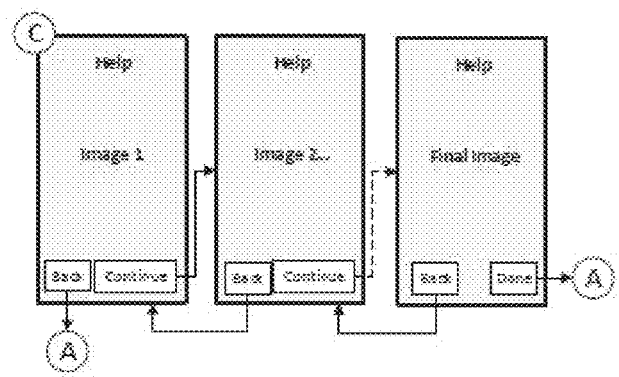
FIG. 16B is a flow diagram illustrating an implementation of portions of the method of FIG. 8.
Figure 16C:
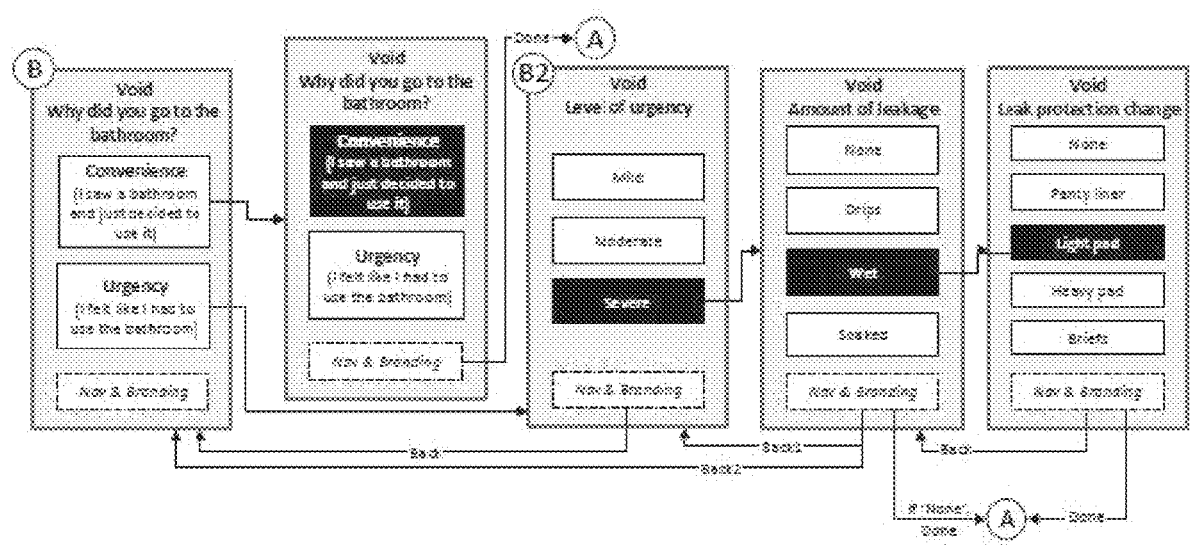
FIG. 16C is a flow diagram illustrating an implementation of portions of the method of FIG. 8.
Figure 16D:
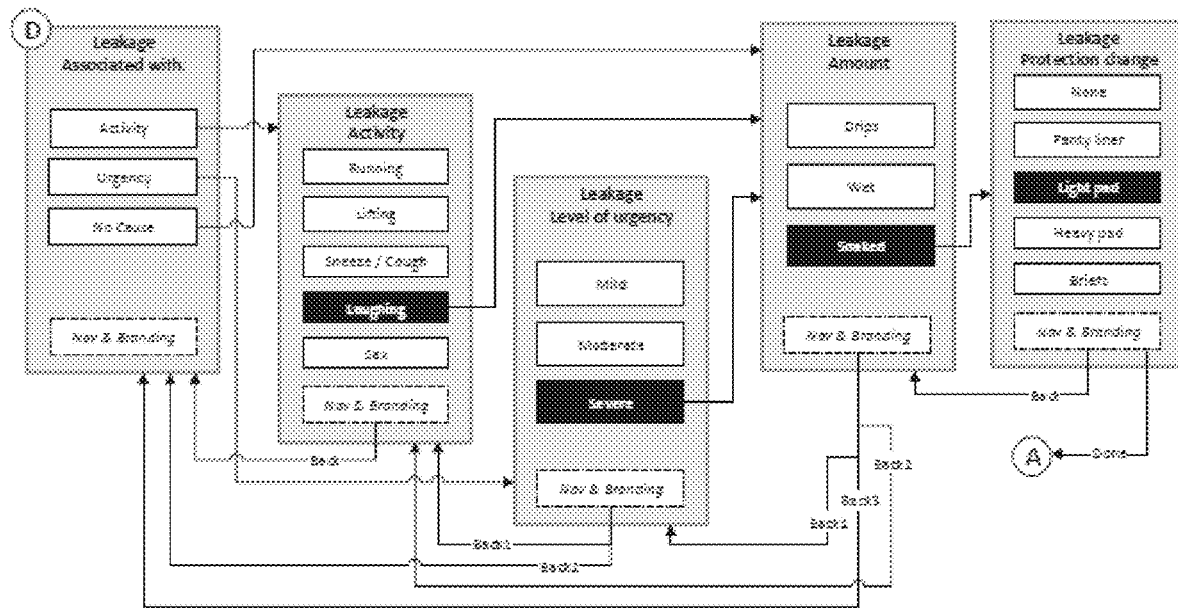
FIG. 16D is a flow diagram illustrating an implementation of portions of the method of FIG. 8.
Figure 16E:
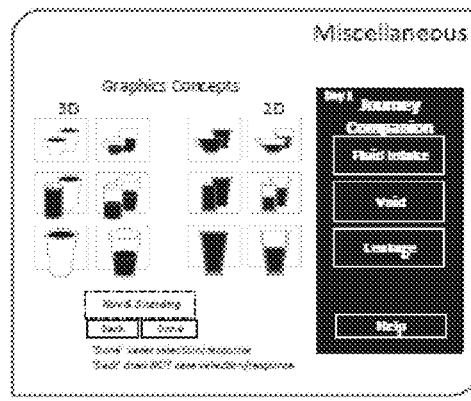
FIG. 16E is a flow diagram illustrating an implementation of portions of the method of FIG. 8.

FIGS. 16A-16E are flow diagrams illustrating a specific implementation of the method of FIG. 8. FIGS. 16A-16E are examples of a specific implementation, and are not intended to limit method 800 in any way. As illustrated in FIG. 16A, the user mobile device 108 executes an application that starts with a splash screen welcoming the user. The application then proceeds to a screen to ask the user about certain urinary events, such as beverage consumption, controlled void events, and UI events, or leaks. If the user selects "I had a beverage" the application proceeds to ask about the size of the beverage. FIG. 16E illustrates sample graphics of the user interface related to beverage consumption. If the user selects, "I went to the bathroom", the application attempts to scan the server 112 for validated void data. If validated void data are found, the application proceeds to node B in as illustrated in FIG. 16C and the application asks the user about the reasons he or she urinated, e.g., the level of urgency, convenience, the level of UI leakage, and any change in leakage protection. The application also asks the user about whether he or she is getting up for the day, or went to the bathroom during the night due to urgency, as illustrated in node A in FIG. 16A. If the user selects, "I had a leak", the application proceeds to node D, FIG. 16D where the user is asked about activity associated with the leak; e.g., running, lifting, laughing, sex, etc.; the size of the leak; and leakage protection changes. The application may also show help screens as illustrated in FIG. 16B.

Figure 9:
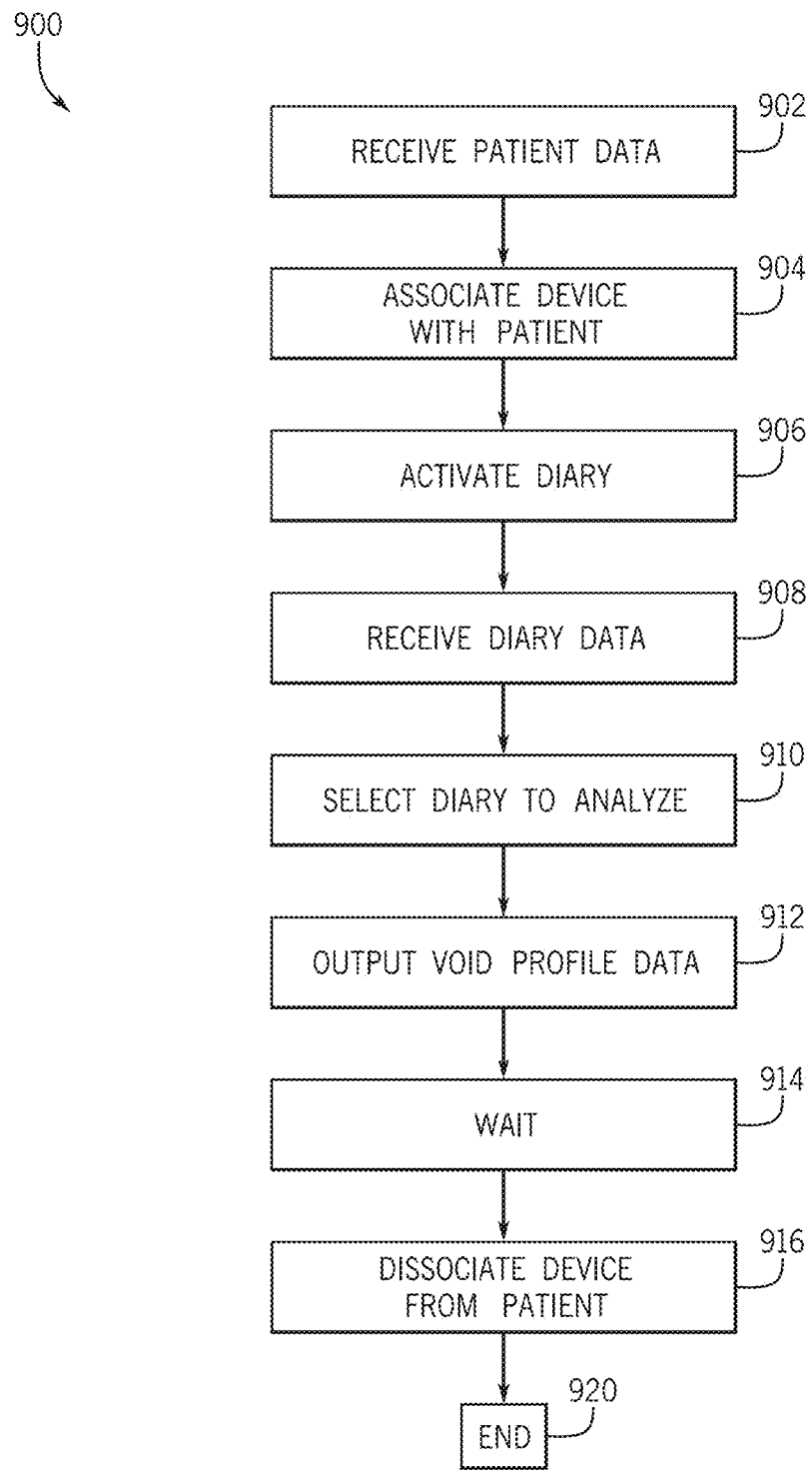
FIG. 9 is a flow chart illustrating a method for associating a void information with a select patient.

As mentioned, the voiding device 200 and void data can be used to collect and analyze urinary data for treatment. FIG. 9 discloses a method 900 to analyze data regarding the patient's urinary health utilizing the voiding device 200. The method may be executed in one or more of the healthcare provider device 109, the report device 110, the server 112, the third party device 103, the user mobile device 108, or even another suitable device.

The method may begin with operation 902 and a processing element receives patient data from one or more of the voiding device 200, the server 112, the healthcare provider device 109, the report device 110, or a third party device 103. The processing element may in the voiding device 200, the report device 110, the healthcare provider device 109, the third party device 103, the server 112, or another device. The respective processing element may receive patient data via network 102 from another device, or it may receive patient data from manual input during or following an examination or interview of the patient. In one example, a doctor or other healthcare provider manually inputs patient information into the healthcare provider device 109 such as a computer, tablet, mobile phone or other computing device. The patient data can include height, weight, age, name, or other patient identifier, or the like data corresponding to the patient. The type of patient data may vary as desired but generally is to identify a patient out of a plurality of patients.

The method may proceed to operation 904 and a healthcare provider assigns a voiding device 200 for patient use, and associates, or creates a linkage between, a particular voiding device 200 and a particular patient. The voiding device 200 may have a device identifier that may be unique. Optionally, different portions of the voiding devices 200 may have different device identifiers, e.g., the handle 202 may have one device identifier and the flow chamber 204 may have another device identifier. The device identifiers may associate a handle 202 with a flow chamber 204, and with a patient. In one example, a unique device identifier is a serial number, bar code, image, etc., such that the voiding device 200 can be tracked as to which patient it is associated with, and may be dissociated from one patient and associated with another patient. In one example, the device identifier may be associated with a disposable flow chamber 204 that is removable attached to the handle 202. A new disposable flow chamber 204 may be associated with the handle 202 for each patient using the voiding device 200. The flow chamber 204 may contain an RFID element that stores the device identifier. The device identifier stored in the RFID element may be read to ensure the flow chamber 204 is used with only one patient.

Patients may also have patient identifiers that may be unique. In one example, a unique patient identifier is a patient number, or patient name plus birthdate. In one example, to associate the voiding device 200 with a patient, the healthcare provider causes the processing element within the healthcare provider device 109 to create a record in memory linking a patient unique identifier with the voiding device 200 unique identifier. This record may be transmitted to the server 112, or other devices within the information management system 100. In another example, the respective processing element causes a confirmation display confirming a linkage between the patient identifier and the device identifier.

The method may proceed to operation 906 and a void diary is activated or associated with a particular patient. In one example, the healthcare provider device 109 associates a voiding devices 200 with a patient. In one example, the void diary is a database stored in memory on the healthcare provider device 109, the user mobile device 108, and/or on the server 112 and contains records regarding the patient's urinary health. The void diary contains a record of the association between the patient and the voiding device 200, such as that resulting from operation 904.

The method may proceed to operation 908 and the respective processing element receives void diary data corresponding to the user's voiding or urinary events, such as the inputs from the method 800 in FIG. 8. The respective processing element may receive diary data via the network 102 from one or more of the voiding device 200, the report device 110, the healthcare provider device 109, the third party device 103, the server 112, or another device. Alternately, the respective processing element may receive void diary data directly from one of the preceding devices. In one example, the healthcare provider device 109 is a tablet, or other portable computer in communication with the user mobile device 108 over the network 102. The user mobile device 108, such as a smart phone, may be in communication with both the healthcare provider device 109 and the voiding device 200. In one example, the user mobile device 108 transmits void diary data to the healthcare provider device 109 over a Wi-Fi® network connection. In another example, the voiding device 200 transmits void diary data over a private cellular network. In one example, the user mobile device 108 sends void diary data to the server 112 that is in communication with the healthcare provider device 109, which receives void diary data from the server 112.

As illustrated in FIG. 8, the void diary data corresponds to the urinary and void events as well as patient input information such as patient feelings, consumption, etc. The method may proceed to operation 910 and the respective processing element may select a particular void diary to access. In one example, the respective processing element displays a user interface on a tablet computer and a doctor, after providing security authentication, selects a diary from among various void diaries available to access. In one example, the respective processing element sends an alert to the doctor telling him/her that new void diary information is available, and provides a link, such as a hyperlink, for the doctor to follow, allowing access to the void diary.

The method may proceed to operation 912 and the respective processing element outputs void diary data or urinary health report containing information gathered by the voiding device 200 and/or information gathered by the patient, that relate to the patient's urinary health. FIG. 11 illustrates one example of a void diary report. The void diary report may be displayable on a user mobile device 108, healthcare provider device 109, or other device. In this example, void data are seen for three days and nights, for a patient. Void data presented in the example include: daily data for the number of voids; void volume; fluid intake; a count of UI episodes; daily averages for urine output, fluid intake, maximum bladder capacity, number of voids, average void volume, minimum void volume, daily and nightly UI episode count. The example also shows data on UI episodes such as urgency of urination, activities leading to UI episodes, the amount of urine leakage, and absorbent pad use. The void diary includes user input such as received by a user from the input/output of a user mobile device 108, input received from the healthcare provider device 109, as well as void data collected from a voiding device 200. For example, the diary in FIG. 11 contains user feelings, such as urgency of urination, as well as void data from voiding device 200, such as voided volume, number of voids, and maximum bladder capacity.

The method may proceed to operation 914 and the respective processing element waits for the prescribed time for a patient to use the voiding device 200 and/or to keep a void diary. During this operation, additional void diary data may be accumulated and the method may return to any of operations 902-910, as desired.

The method may proceed to operation 916 and the respective processing element allows a healthcare provider or other person to dissociate the voiding device 200 with a particular patient, breaking, destroying, or deactivating the association made between patient and the voiding device 200 in operation 904. A server 112 may keep a record of the patients who have used a particular voiding device 200, and/or the voiding devices 200 associated with a particular patient after the association is deactivated. The dissociation may also trigger a report to be generated by a processing element in one or more devices. The voiding device 200 may then be returned in whole or in part to the healthcare provider. The healthcare provider, or a medical device service provider, cleans, sanitizes, and recharges the device for further use with another patient. The healthcare provider may separate portions of the device using a custom tool or key, (as illustrated for example in FIGS. 2O and 2P) discard part of the device, saving a durable portion for reuse. In one example, the healthcare provider discards the flow chamber 204, keeping the handle 202 of the voiding device 200 for further use. In one example, the device identifier is read from the RFID element within the flow chamber 204 to ensure that particular device identifier is no longer associated with the patient, and may not be re-assigned to any new patient, ensuring single patient use of the flow chamber 204. The flow chamber 204 is separated from the handle 202, and discarded. A new flow chamber 204 with a new device identifier may be associated with the handle 202. The new device identifier may be stored in an RFID element within the flow chamber 204. The method may end in operation 920.

Figure 17A:
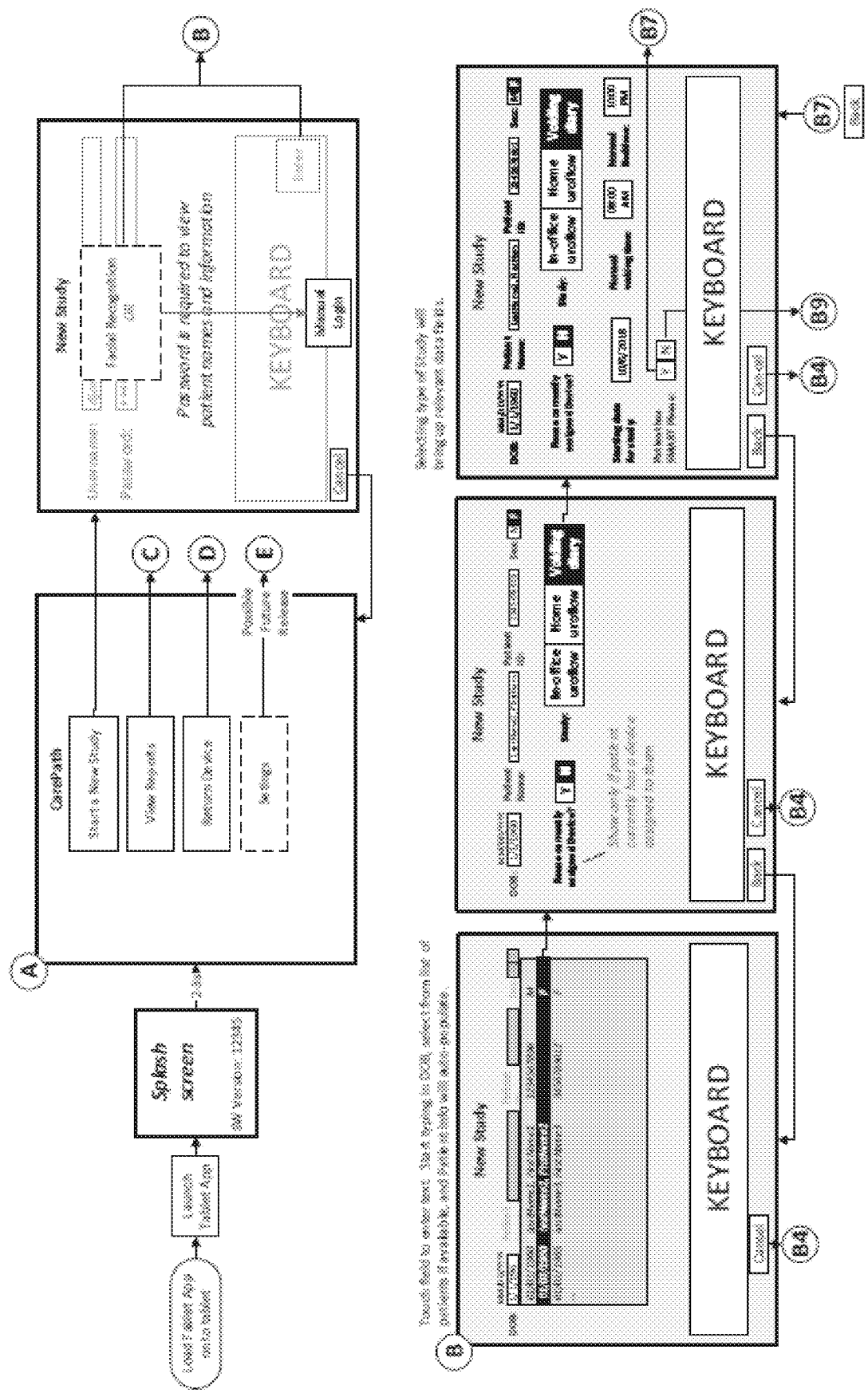
FIG. 17A is a flow diagram illustrating an implementation of portions of the method of FIG. 9.
Figure 17B:
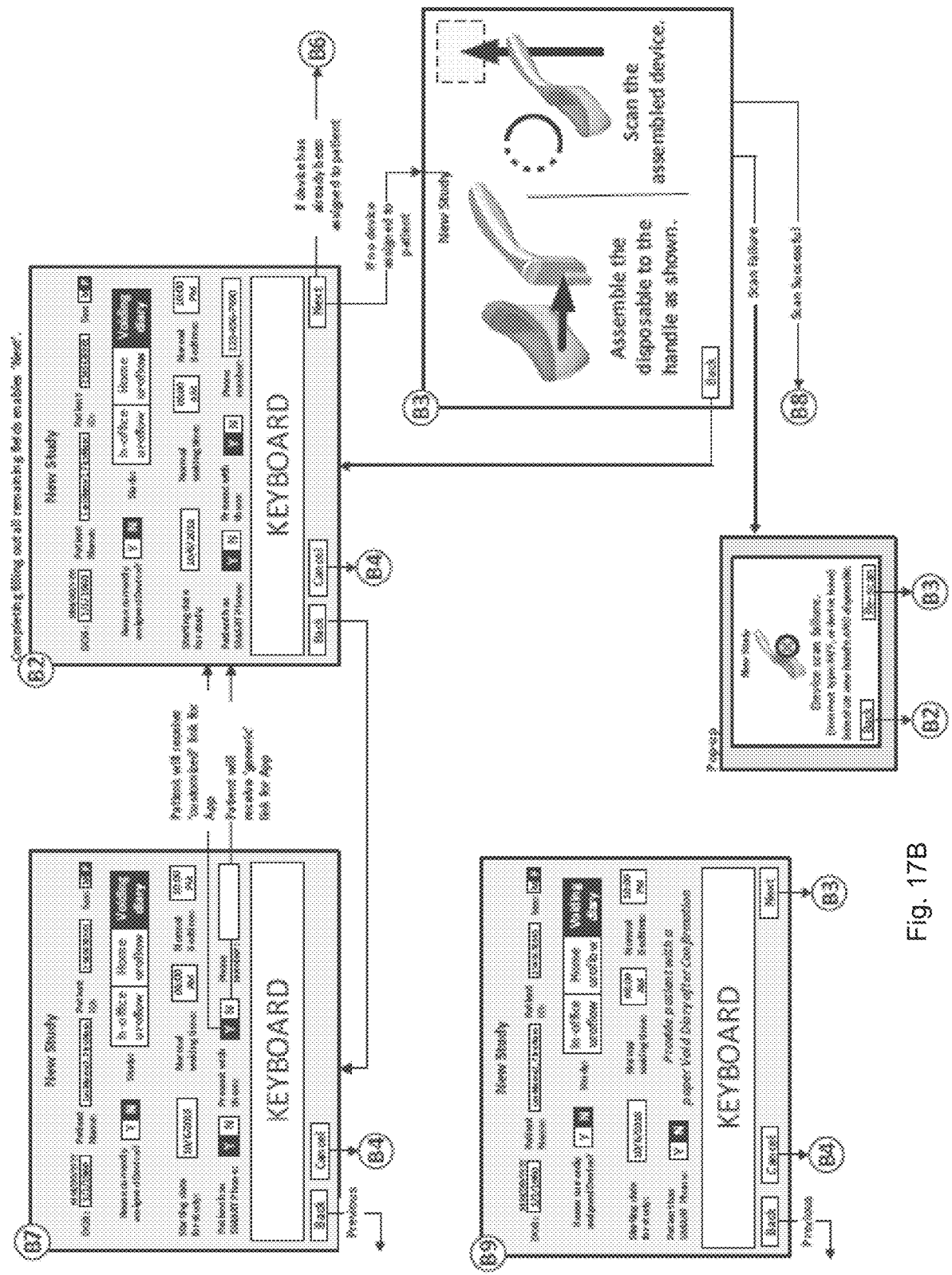
FIG. 17B is a flow diagram illustrating an implementation of portions of the method of FIG. 9.
Figure 17C:
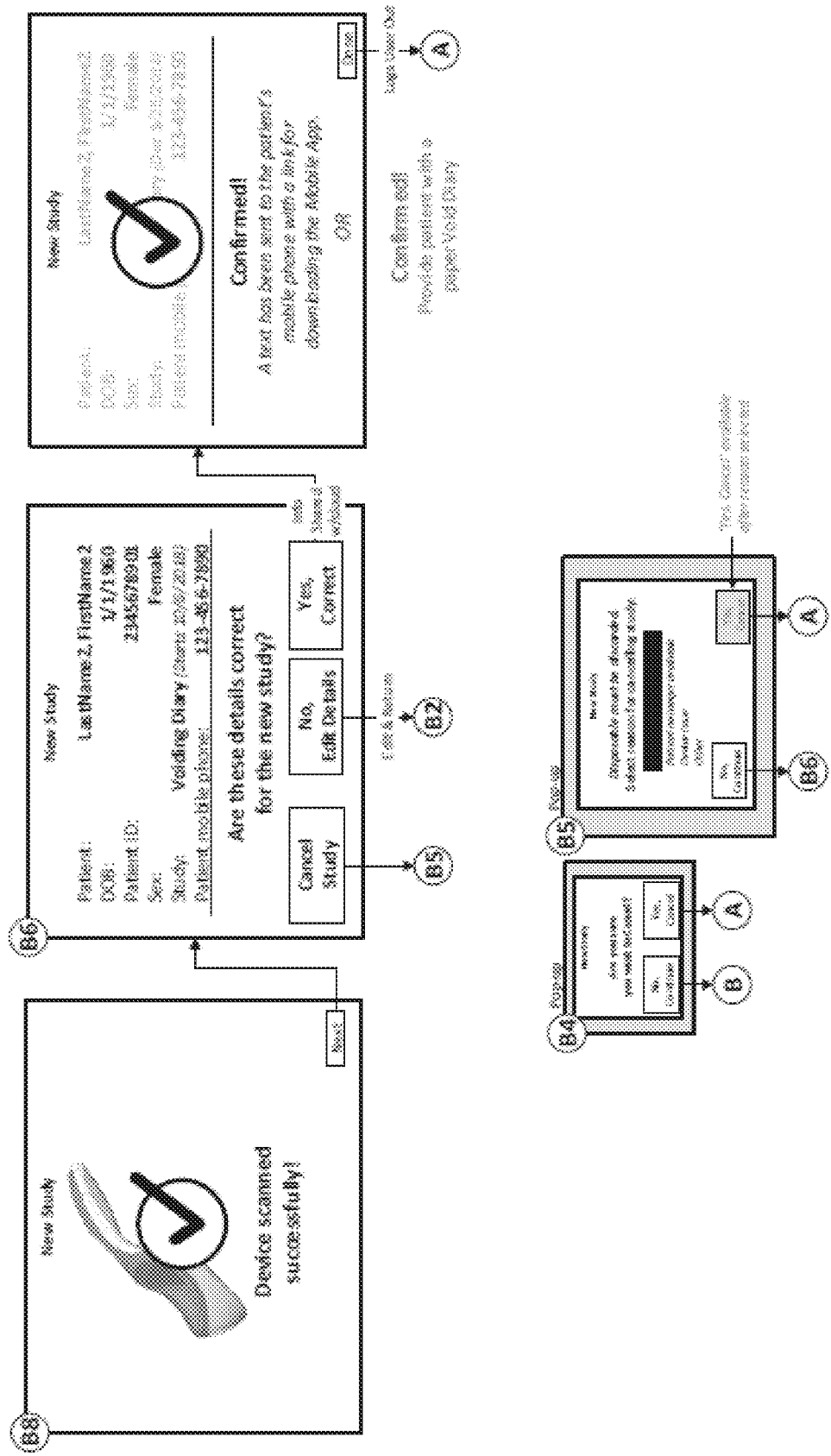
FIG. 17C is a flow diagram illustrating an implementation of portions of the method of FIG. 9.
Figure 17D:
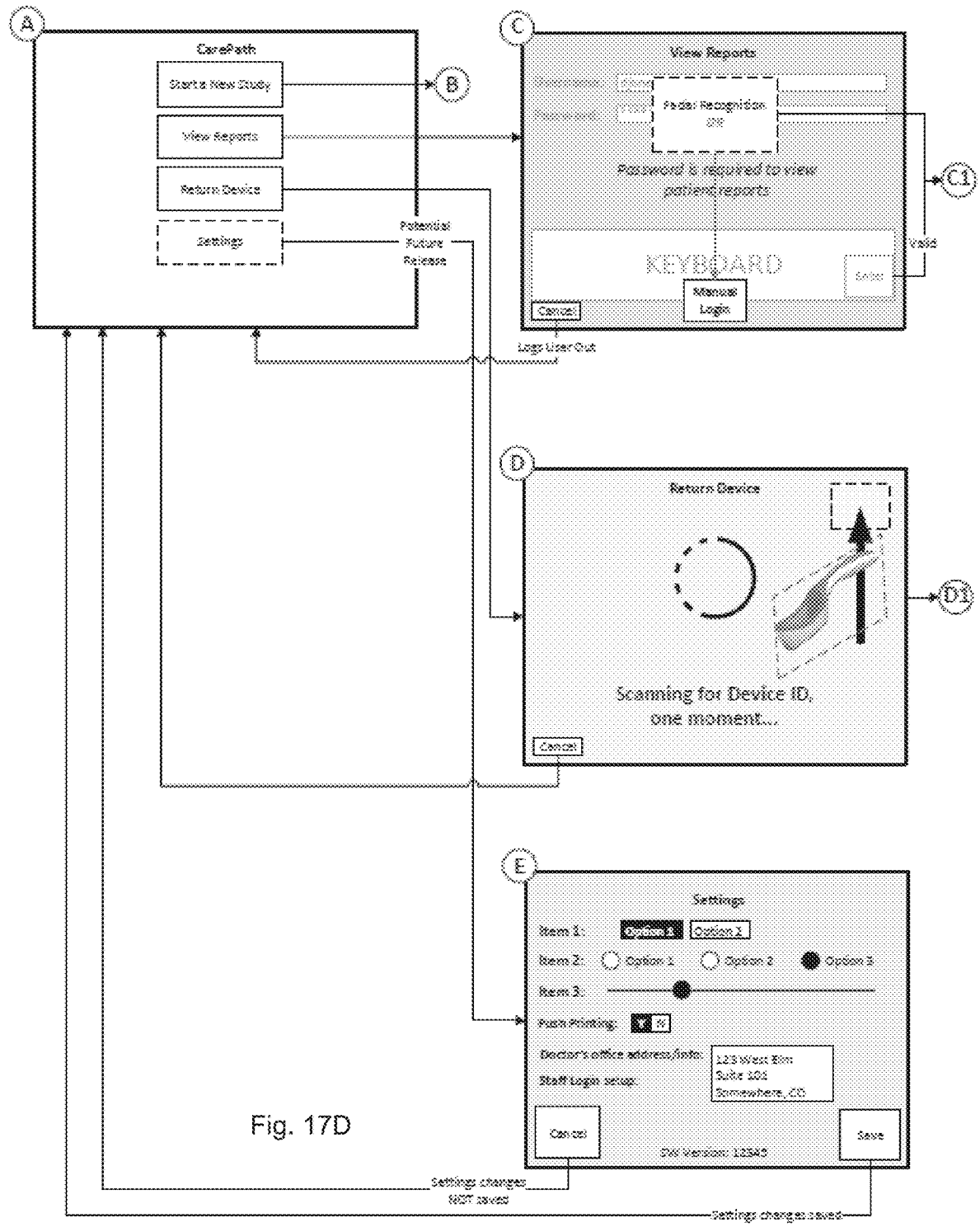
FIG. 17D is a flow diagram illustrating an implementation of portions of the method of FIG. 9.

FIGS. 17A-17E are flow diagrams illustrating a specific implementation of the method of FIG. 9, as may be implemented in an application on a tablet or other computer. FIGS. 17A-17E are examples of a specific implementation, and are not intended to limit method 900 in any way. As illustrated in FIG. 17A, the application begins with a splash screen then proceeds to node A where it offers the user the options to start a new study of a patient, view reports of an existing study, return a device and dissociate it with a patient, or access a settings menu. The application contains provisions for a user to authenticate himself or herself. Node B of FIG. 17A illustrates various screens in the application allowing the user to input information related to a new study, including patient information, the type of study to be completed, whether the patient has a smart phone. As illustrated in FIG. 17B, the screens proceed to allow the user to associate a flow chamber 204 with a handle 202, and scan the assembled device, and associate the assembled voiding device 200 with the patient. If the association of voiding device 200 to patient is successful, the application proceeds to FIG. 17C, node B8 to complete the setup of the new study. If the user chooses to view reports from the opening screen, the application proceeds to FIG. 17D, node C, and then FIG. 17 E, node C1 where the user authenticates him or herself and may then view void diary reports on patients. Is the user chooses to return a device from the opening screen, the application proceeds to FIG. 17D, node D and FIG. 17E, node D1. Here the user is prompted to scan the device to return, and is notified when the scan is successful. If the user chooses to enter the settings screen from the opening screen, he or she may enter a settings screen as illustrated for example in FIG. 17D.

Figure 10:
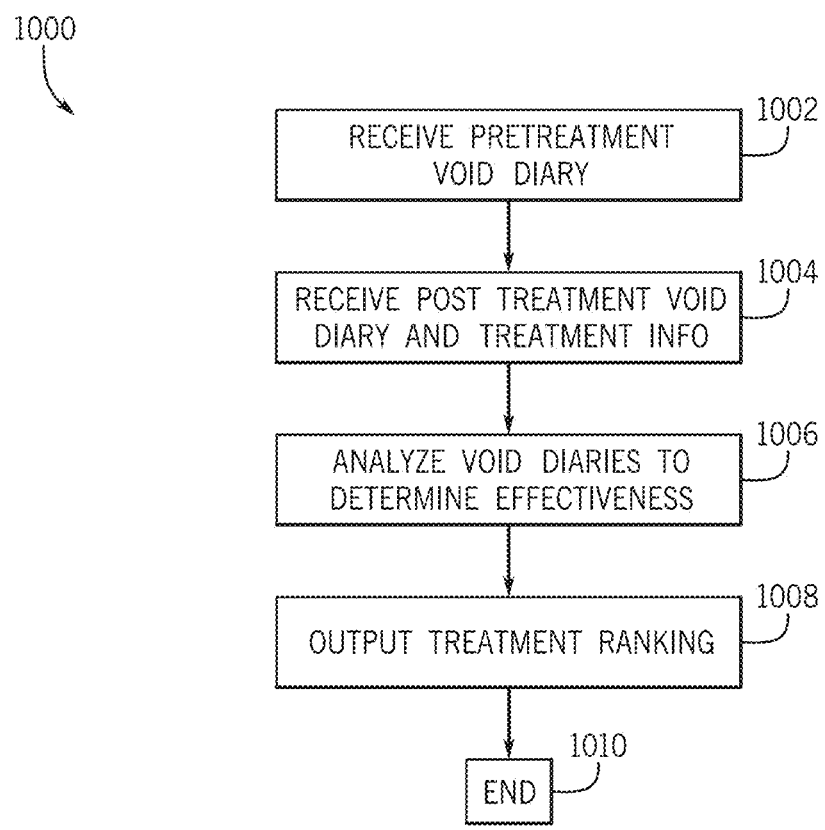
FIG. 10 is a flow chart illustrating a method to determine treatment effectiveness with a voiding device of FIG. 2A.
Figure 21:
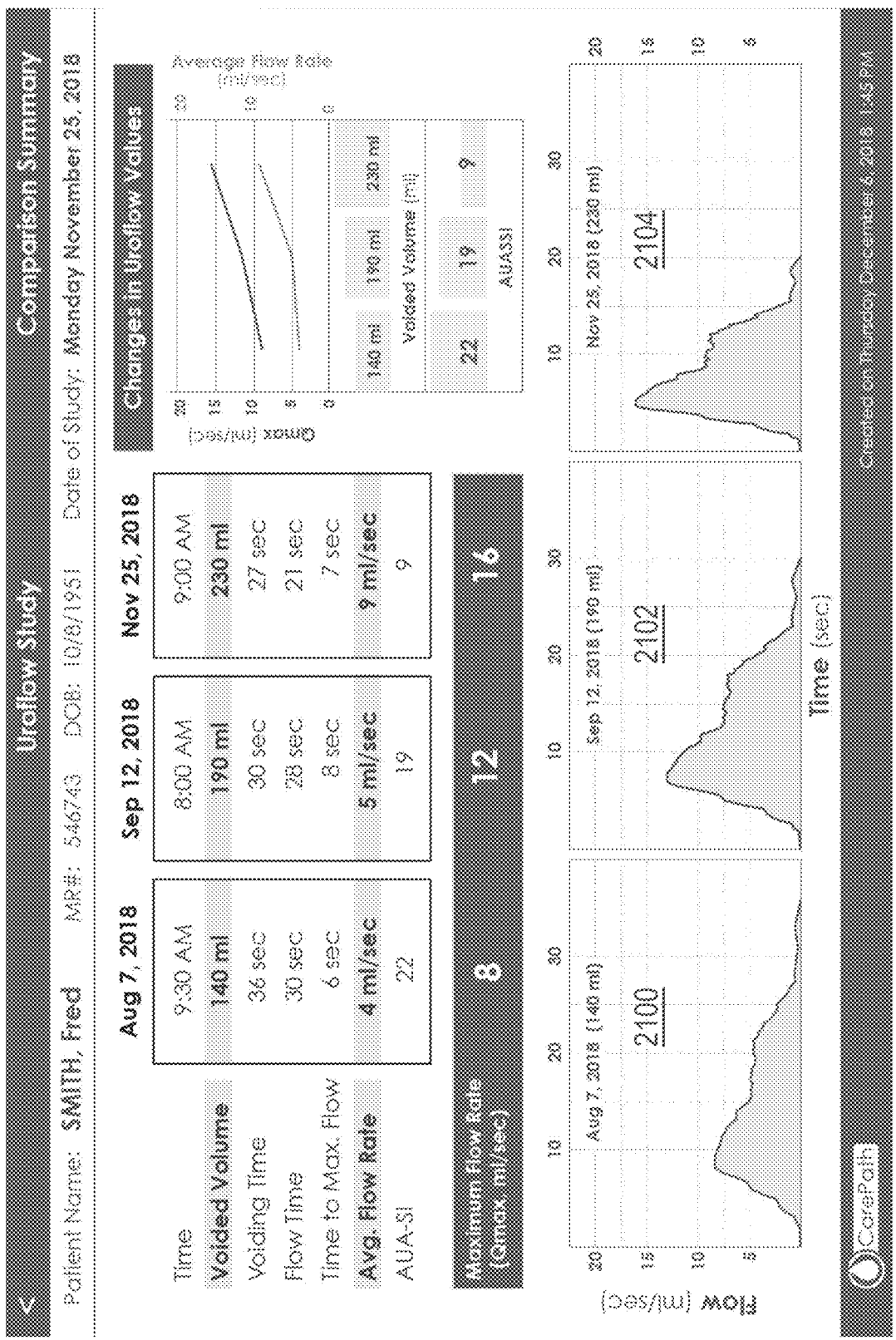
FIG. 21 is an example of a comparison report of uroflow study data of a patient over a span of several months.
Figure 22:
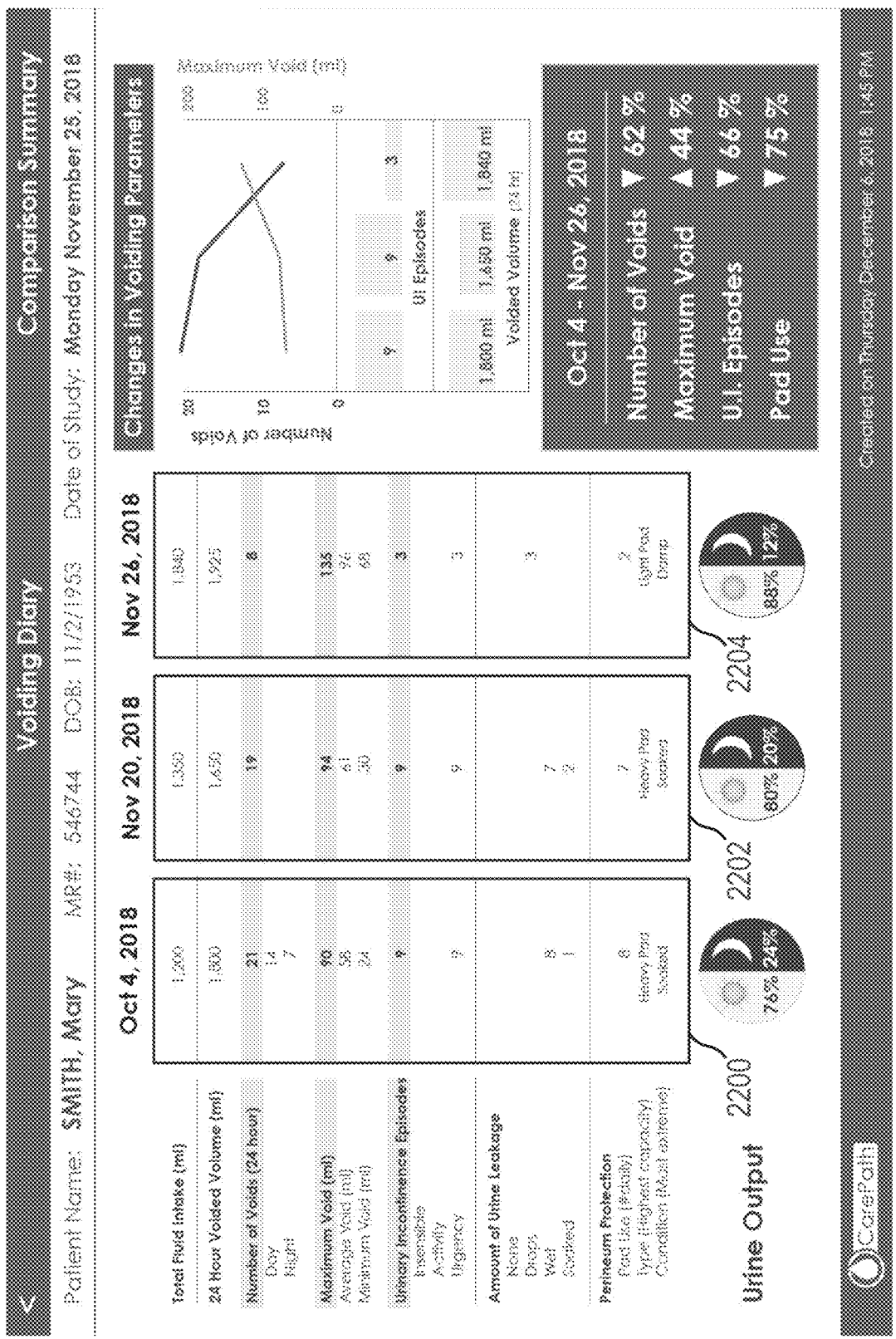
FIG. 22 is an example of a comparison report of voiding diary data of a patient over a span of several months.

FIG. 10 discloses a method 1000 where a processing element receives pre-treatment void diary information and post-treatment void diary information in order to assess efficacy of and payments for the treatment. The processing element may in the voiding device 200, the report device 110, the healthcare provider device 109, the third party device 103, the server 112, or another device. The ability to compare information may help the healthcare provider choose the best course of treatment, and may also establish a baseline of symptoms that an insurer and/healthcare provider can use to assess the efficacy of the treatment. Examples of reports generated by the disclosed systems are illustrated in FIGS. 21 and 22, showing a patient's uroflow study and void diary information over the span of several months.

The method may begin in operation 1002 where pre-treatment void diary information is be received by the respective processing element on report device 110 or on the healthcare provider device 109. Void diary information may be collected in the manner and with the methods and devices described above. In one example, a healthcare provider prescribes a voiding device 200 to a patient seeking care for UI symptoms and asks the patient to use the voiding device 200 and keep a void diary before any treatment begins. The patient then collects void diary information as disclosed. The server 112 may make reports or the void diary available to the report device 110 and/or the healthcare provider device 109. In one example, the server may provide a link to the reports or void diary. In another example, the server 112 may transmit a copy of the report or void diary. In one example, a pre-treatment void diary 2200 is illustrated in FIG. 22. Alternately, a pre-treatment uroflow study 2100, illustrated for example, in FIG. 21, may be received.

The method may proceed to operation 1004 and the patient is treated for UI symptoms and/or causes and collects post-treatment void diary information that is received by the respective processing element. In one example, the patient collects void diary information using the voiding device 200 and the user mobile device 108. The patient transmits the post-treatment void diary information to the server 112, the healthcare provider device 109, the report device 110 or other devices according to the methods disclosed. For example, the patient may use the voiding device 200 as disclosed, and the voiding device 200 may transmit void diary information to the server 112, the healthcare provider device 109, the report device 110 or other devices. In various examples, as illustrated in FIGS. 21 and 22, post treatment uroflow studies 2102, 2104 and post-treatment void diaries, 2202, 2204 may be generated.

The method may proceed to operation 1006 and the respective processing element analyzes the pre-treatment and post-treatment void diaries and/or uroflow studies to provide comparison information to determine treatment effectiveness. In one example, the respective processing element produces a report, for example, FIG. 21 or 22 showing the change in the number of UI episodes, a change in leakage volumes, urgency, urine volume, urine flow rates, and other data for the post-treatment condition, allowing healthcare providers and insurers to make decisions on treatment effectiveness.

The method may proceed to operation 1008 and the respective processing element ranks effectiveness for different treatments based on improvements in post-treatment UI symptoms. In one example, the respective processing element aggregates anonymized patient data including post-treatment outcomes. The respective processing element further categorizes outcomes according to patient demographic data, such as weight, age, gender, ethnicity, and further categorizes data according to the treatments employed. The respective processing element may then rank the most effective treatments for the whole population of patient records, or may a provide rankings for subsets of the population. For example, the respective processing element may determine that treatment with drug "A" is the most effective for females over the age of 50, whereas it may determine that treatment with drug "B" is most effective for males over the age of 50. The method ends in operation 1010

Figure 15:
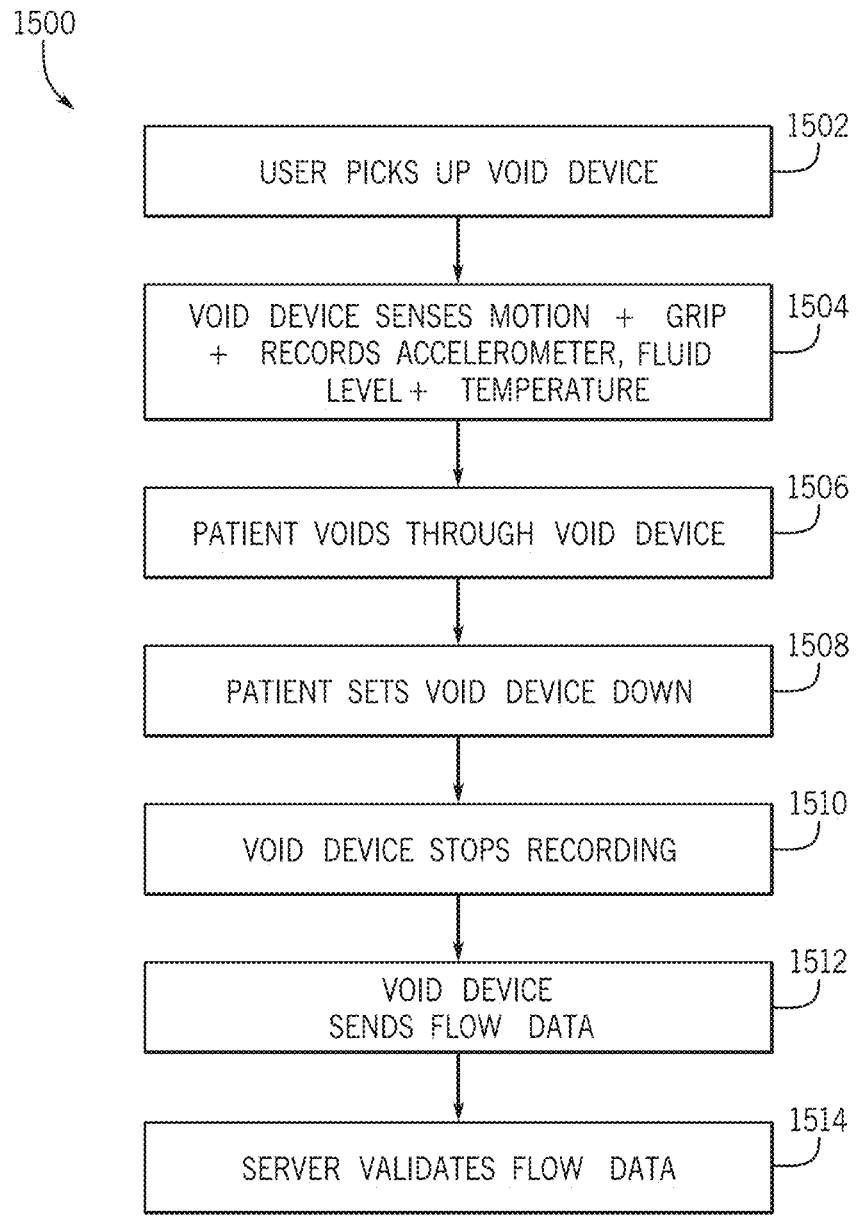
FIG. 15 is a flow chart of a method for activating, using, and transferring data using the voiding device of FIG. 2A.

FIG. 15 illustrates an example of a typical usage method 1500 for the voiding device 200. The method may begin in operation 1502 when a patient picks up the voiding device 200. In operation 1504 the voiding device 200 senses motion for instance by way of the validation sensor 260, or the patient's grip by way of the power button 279 and/or a touch sensor. In operation 1504, the voiding device 200 begins recording sensor data, such as validation sensor 260 data, fluid level data, and/or temperature, conductivity, opacity, or other data. In operation 1506, the patient voids through the voiding device 200. In operation 1508, the patient sets the voiding device 200 down. In operation 1510 the voiding device 200 stops recording sensor data. In operation 1512, the voiding device 200 communicates with, and sends flow event data to, the server 112. In operation 1514, the server 112 validates the flow data as either being validated void data, or discards it as not being validated void data.

The above specifications, examples, and data provide a complete description of the structure and use of exemplary examples of the invention as defined in the claims. Although various examples of the disclosure have been described above with a certain degree of particularity, or with reference to one or more individual examples, those skilled in the art could make numerous alterations to the disclosed examples without departing from the spirit or scope of the claimed invention. Other examples are therefore contemplated. It is intended that all matter contained in the above description and shown in the accompanying drawings shall be interpreted as only illustrative of particular examples and not limiting. Changes in detail or structure may be made without departing from the basic elements of the invention as defined in the following claims.

All relative and directional references (including: upper, lower, upward, downward, left, right, leftward, rightward, top, bottom, side, above, below, front, middle, back, vertical, horizontal, right side up, upside down, sideways, and so forth) are given by way of example to aid the reader's understanding of the particular examples described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

We claim:

1. A method for generating a urine flow void profile for a user flow event, comprising:
   receiving by a processing element a plurality of outputs from a fluid level sensor adjacent a magnet and configured to detect a movement of a position of the magnet, the plurality of outputs corresponding to a plurality of levels of fluid flowing through a handheld voiding device held by a user during a flow event, wherein:
      the magnet is rotationally coupled with a float via an arm;
      the float is positionable according to the plurality of levels of fluid;
      the float and the arm rotate around a pivot axis in response to the plurality of levels of fluid;
      the magnet connected to the arm rotates around the pivot axis;
   determining by the processing element a beginning and an end time of the fluid flow into the handheld voiding device during the flow event;
   analyzing the plurality of outputs of the fluid level sensor over a time interval defined by the beginning and end time of the fluid flow to determine at least one of a fluid flow rate data and an accumulated volume data for the fluid flowing through the handheld voiding device; and
   storing the fluid flow rate data and the accumulated flow volume data in a memory.

2. The method of claim 1, wherein the plurality of outputs of the fluid level sensor correspond to two or more positions of the fluid level sensor during the time interval.

3. The method of claim 2, wherein the fluid level sensor comprises:
   the float;
   the magnet; and
   a displacement sensor in communication with the magnet to detect variations in position of the magnet.

4. The method of claim 3, wherein the displacement sensor is a Hall effect sensor.

5. The method of claim 1, further comprising:
   analyzing by the processing element one or more validation characteristics detected by the handheld voiding device during the flow event to validate the flow event as a void event.

6. The method of claim 5, wherein the one or more validation characteristics comprise one or more:
   acceleration of the handheld voiding device during the flow event;
   orientation of the handheld voiding device during the flow event;
   presence of a user hand on the handheld voiding device during the flow event;
   temperature of the fluid flowing through the handheld voiding device during the flow event; or
   total volume of the fluid flowing through the handheld voiding device during the flow event.

7. The method of claim 1, wherein the accumulated flow volume data are determined by numerical integration of the fluid flow rate data and wherein the fluid flow rate data are determined based on a predetermined characteristic of the handheld voiding device represented by a lookup table.

8. The method of claim 1, wherein the determining of the fluid flow rate further comprises:
   receiving from an validation sensor a plurality of orientation values for the handheld voiding device over the time interval, the orientation values including a pitch value;
   translating the orientation values and the plurality of outputs of the fluid level sensor during the time interval to a fluid flow rate based on a predetermined characteristic of the handheld voiding device.

9. The method of claim 8, wherein the predetermined characteristic of the handheld voiding device is represented by a lookup table.

10. The method of claim 9, wherein the determining of the fluid flow rate further comprises:
    receiving from the validation sensor a plurality of orientation values for the handheld voiding device over the time interval, the orientation values including a roll value;
    determining the fluid flow rate by comparing two or more of the plurality of pitch values, plurality of the roll values, or plurality of outputs of the fluid level sensor, to a lookup table.

11. The method of claim 1, further comprising:
    receiving by the processing element an initial position of the fluid level sensor; and
    receiving by the processing element a time stamp.

12. The method of claim 1, further comprising:
    receiving by the processing element an initial orientation of the handheld voiding device in space; and
    receiving by the processing element a time stamp.

13. The method of claim 1, wherein the handheld voiding device further comprises a handle detachably coupled to the voiding device and configured to selectively position the voiding device relative to the user to receive the flow of urine during the user flow event.

\* \* \* \* \*